(12) United States Patent
Leen et al.

(10) Patent No.: US 11,931,408 B2
(45) Date of Patent: Mar. 19, 2024

(54) IMMUNOGENIC ANTIGEN IDENTIFICATION FROM A PATHOGEN AND CORRELATION TO CLINICAL EFFICACY

(71) Applicant: Baylor College of Medicine, Houston, TX (US)

(72) Inventors: Ann Marie Leen, Houston, TX (US); Pailbel Aguayo-Hiraldo, Houston, TX (US); Ifigeneia Tzannou, Houston, TX (US); Juan F. Vera Valdes, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 17/480,741

(22) Filed: Sep. 21, 2021

(65) Prior Publication Data

US 2022/0001005 A1 Jan. 6, 2022

Related U.S. Application Data

(63) Continuation of application No. 15/759,501, filed as application No. PCT/US2016/052487 on Sep. 19, 2016, now Pat. No. 11,167,024.

(60) Provisional application No. 62/220,884, filed on Sep. 18, 2015.

(51) Int. Cl.
| | |
|---|---|
| *A61K 31/7088* | (2006.01) |
| *A61K 39/00* | (2006.01) |
| *A61K 39/155* | (2006.01) |
| *A61K 39/395* | (2006.01) |
| *G01N 33/50* | (2006.01) |
| *G01N 33/569* | (2006.01) |
| *G01N 33/574* | (2006.01) |
| *G01N 33/68* | (2006.01) |

(52) U.S. Cl.
CPC ............ *A61K 39/155* (2013.01); *A61K 39/00* (2013.01); *A61K 39/395* (2013.01); *G01N 33/505* (2013.01); *G01N 33/569* (2013.01); *G01N 33/574* (2013.01); *G01N 33/68* (2013.01); *A61K 2039/5154* (2013.01); *A61K 2039/5158* (2013.01); *A61K 2300/00* (2013.01); *G01N 2800/26* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,641,628 A | 6/1997 | Bianchi |
| 5,843,405 A | 12/1998 | Middeldorp |
| 5,869,453 A | 2/1999 | Moss et al. |
| 5,962,318 A | 10/1999 | Rooney et al. |
| 6,040,177 A | 3/2000 | Riddell et al. |
| 6,143,865 A | 11/2000 | Middeldorp |
| 6,274,378 B1 | 8/2001 | Steinman et al. |
| 6,451,305 B1 | 9/2002 | Boussiotis et al. |
| 6,455,299 B1 | 9/2002 | Steinman et al. |
| 6,528,307 B1 | 3/2003 | Herlyn |
| 6,699,477 B2 | 3/2004 | Khanna et al. |
| 6,713,053 B1 | 3/2004 | Bach et al. |
| 6,723,695 B1 | 4/2004 | Burrows et al. |
| 6,821,778 B1 | 11/2004 | Engleman et al. |
| 6,828,147 B1 | 12/2004 | Santoli et al. |
| 7,005,131 B1 | 2/2006 | Steinman et al. |
| 7,638,325 B2 | 12/2009 | June et al. |
| 7,723,107 B2 | 5/2010 | Kirkin et al. |
| 7,745,140 B2 | 6/2010 | June et al. |
| 7,785,806 B2 | 8/2010 | Warren et al. |
| 7,785,875 B2 | 8/2010 | Hwang et al. |
| 7,811,581 B2 | 10/2010 | Middeldorp |
| 7,846,446 B2 | 12/2010 | Cannon et al. |
| 7,951,383 B2 * | 5/2011 | Murphy ............... C12N 7/00 424/211.1 |
| 7,994,096 B2 | 8/2011 | Kem et al. |
| 8,138,314 B2 | 3/2012 | Exley et al. |
| 8,481,051 B2 | 7/2013 | Kuzushima et al. |
| 8,546,137 B2 | 10/2013 | Cannon et al. |
| 8,722,401 B2 | 5/2014 | Groux et al. |
| 8,741,642 B2 | 6/2014 | Manjili et al. |
| 9,115,402 B2 | 8/2015 | Hacohen et al. |
| 9,255,243 B2 | 2/2016 | Wilson et al. |
| 9,963,677 B2 * | 5/2018 | Leen ................ C12N 5/0638 |
| 10,351,824 B2 | 7/2019 | Rooney et al. |

(Continued)

FOREIGN PATENT DOCUMENTS

| | | |
|---|---|---|
| CN | 101427135 A | 5/2009 |
| JP | 2013502235 A | 1/2013 |

(Continued)

OTHER PUBLICATIONS

Leen et al Differential Immunogenicity of Epstein-Barr Virus Latent-Cycle Proteins for Human CD41 T-Helper 1 Responses Journal of Virology, Sep. 2001, p. 8649-8659.*

Tedcastle et al., The Characterization of Monoclonal Antibodies to Human Metapneumovirus and the Detection of Multiple Forms of the Virus Nucleoprotein and Phosphoprotein Journal of Medical Virology 84:1061-1070 (2012).*

Leen et al., Multicenter study of banked third-party virus-specific T cells to treat severe viral infections after hematopoietic stem cell transplantation Blood, Jun. 27, 2013 x vol. 121, No. 26; pp. 5113-5123.*

Jenkins et al In Vivo Activation of Antigen-Specific CD4 T Cells Annu. Rev. Immunol. 2001. 19:23-45.*

(Continued)

*Primary Examiner* — Maria G Leavitt
(74) *Attorney, Agent, or Firm* — Norton Rose Fulbright US LLP

(57) ABSTRACT

Embodiments of the disclosure concern methods of identifying whether or not antigens from a particular pathogen are immunogenic, including the order of their immunogenicity. Other embodiments concern correlations between attributes of T cells and their clinical efficacy, such as mathematical representations thereof.

6 Claims, 47 Drawing Sheets

(56) References Cited

U.S. PATENT DOCUMENTS

| | | | |
|---|---|---|---|
| 10,385,316 B2 | 8/2019 | Leen et al. | |
| 10,556,943 B2 | 2/2020 | Knutson et al. | |
| 11,111,816 B2 | 9/2021 | Lad | |
| 11,118,164 B2 | 9/2021 | Leen et al. | |
| 11,155,784 B2 | 10/2021 | Rooney et al. | |
| 11,167,024 B2 | 11/2021 | Leen et al. | |
| 2002/0051784 A1 | 5/2002 | Boussiotis et al. | |
| 2002/0119121 A1 | 8/2002 | Vitiello et al. | |
| 2002/0155108 A1 | 10/2002 | Barbera-Guillem | |
| 2003/0148982 A1 | 8/2003 | Brenner et al. | |
| 2003/0153073 A1 | 8/2003 | Rogers et al. | |
| 2003/0219458 A1 | 11/2003 | Wang | |
| 2004/0022761 A1 | 2/2004 | Banchereau et al. | |
| 2004/0096457 A1 | 5/2004 | Huber et al. | |
| 2004/0106159 A1 | 6/2004 | Kern et al. | |
| 2005/0028505 A1 | 2/2005 | Schumacher | |
| 2005/0106717 A1 | 5/2005 | Wilson et al. | |
| 2005/0221481 A1 | 10/2005 | Migliaccio et al. | |
| 2006/0045883 A1 | 3/2006 | Molldrem et al. | |
| 2006/0073126 A1 | 4/2006 | Shiku et al. | |
| 2006/0204509 A1 | 9/2006 | Harty et al. | |
| 2006/0251664 A1 | 11/2006 | Kropshofer et al. | |
| 2007/0003531 A1 | 1/2007 | Mukherji et al. | |
| 2007/0048329 A1 | 3/2007 | Khanna et al. | |
| 2007/0098734 A1 | 5/2007 | Cai et al. | |
| 2008/0260701 A1 | 10/2008 | Hope | |
| 2009/0098090 A1 | 4/2009 | Hart et al. | |
| 2009/0305324 A1 | 12/2009 | Kuzushima et al. | |
| 2009/0305408 A1 | 12/2009 | Chang | |
| 2010/0035282 A1 | 2/2010 | Bonini et al. | |
| 2010/0254958 A1 | 10/2010 | Letsch et al. | |
| 2011/0059133 A1 | 3/2011 | Adhikary et al. | |
| 2011/0136228 A1 | 6/2011 | Vera et al. | |
| 2011/0182870 A1* | 7/2011 | Leen | C12N 5/0638 435/375 |
| 2011/0236363 A1 | 9/2011 | Chang et al. | |
| 2011/0262467 A1 | 10/2011 | Riley et al. | |
| 2012/0100180 A1 | 4/2012 | Gao et al. | |
| 2012/0244132 A1 | 9/2012 | Stauss et al. | |
| 2013/0045491 A1 | 2/2013 | Unutmaz | |
| 2013/0058909 A1 | 3/2013 | Szabolcs | |
| 2013/0102075 A1 | 4/2013 | Vera et al. | |
| 2013/0115617 A1 | 5/2013 | Wilson | |
| 2013/0129713 A1 | 5/2013 | Rescigno et al. | |
| 2013/0217122 A1 | 8/2013 | Kaplan | |
| 2014/0212398 A1 | 7/2014 | Reisner et al. | |
| 2015/0010519 A1 | 1/2015 | Leen et al. | |
| 2015/0037297 A1 | 2/2015 | Terman | |
| 2015/0044258 A1 | 2/2015 | Knaus et al. | |
| 2015/0175966 A1 | 6/2015 | Vera et al. | |
| 2015/0337262 A1 | 11/2015 | Ethell | |
| 2016/0208216 A1 | 7/2016 | Vera et al. | |
| 2016/0215351 A1 | 7/2016 | Sahin et al. | |
| 2016/0296563 A1 | 10/2016 | Sourdive et al. | |
| 2016/0362658 A1 | 12/2016 | Leen et al. | |
| 2017/0128565 A1 | 5/2017 | O'Reilly et al. | |
| 2018/0187152 A1 | 7/2018 | Leen et al. | |
| 2018/0250384 A1 | 9/2018 | Leen et al. | |
| 2019/0134092 A1 | 5/2019 | Knaus et al. | |
| 2019/0144826 A1* | 5/2019 | Leen | A61K 39/155 424/93.1 |
| 2019/0264176 A1 | 8/2019 | Leen et al. | |
| 2019/0270966 A1 | 9/2019 | Rooney et al. | |
| 2020/0172864 A1 | 6/2020 | Chiang et al. | |
| 2021/0348127 A1 | 11/2021 | Leen et al. | |
| 2022/0001005 A1 | 1/2022 | Leen et al. | |
| 2022/0152111 A1 | 5/2022 | Knaus et al. | |
| 2022/0169986 A1 | 6/2022 | Leen et al. | |
| 2022/0251508 A1 | 8/2022 | Leen et al. | |
| 2022/0257654 A1 | 8/2022 | Vera Valdes et al. | |
| 2022/0282218 A1 | 9/2022 | Leen et al. | |
| 2022/0288119 A1 | 9/2022 | Vera Valdes et al. | |
| 2023/0028788 A1 | 1/2023 | Leung et al. | |

FOREIGN PATENT DOCUMENTS

| | | |
|---|---|---|
| WO | 1994002156 A1 | 2/1994 |
| WO | 9524217 A1 | 9/1995 |
| WO | 1995027722 A1 | 10/1995 |
| WO | 1995/031208 A1 | 11/1995 |
| WO | 1998033888 A1 | 8/1998 |
| WO | 00/50569 A1 | 8/2000 |
| WO | 2002077030 A2 | 10/2002 |
| WO | 2005028505 A2 | 3/2005 |
| WO | 2005035728 A2 | 4/2005 |
| WO | 2007/097820 A2 | 8/2007 |
| WO | 2007099341 A1 | 9/2007 |
| WO | 2007121276 A2 | 10/2007 |
| WO | 2008025992 A2 | 3/2008 |
| WO | 2008073312 A2 | 6/2008 |
| WO | 2008073313 A2 | 6/2008 |
| WO | 2009053109 A1 | 4/2009 |
| WO | 2011/028531 A1 | 3/2011 |
| WO | 2011024482 A1 | 3/2011 |
| WO | 2011146473 A1 | 11/2011 |
| WO | 2012/062831 A1 | 5/2012 |
| WO | 2013088114 A1 | 6/2013 |
| WO | 2013088147 A1 | 6/2013 |
| WO | 2013088148 A2 | 6/2013 |
| WO | 2013/119947 A1 | 8/2013 |
| WO | 2015/110397 A2 | 7/2015 |
| WO | 2016073550 A1 | 4/2016 |
| WO | 2016073595 A1 | 5/2016 |
| WO | 2016/073595 A8 | 6/2016 |
| WO | 2016/154112 A1 | 9/2016 |
| WO | 2017/049291 A1 | 3/2017 |
| WO | 2017/203368 A1 | 11/2017 |
| WO | 2018/052947 A1 | 3/2018 |
| WO | 2018/055191 A1 | 3/2018 |
| WO | 2018/232467 A1 | 12/2018 |
| WO | 2019/050958 A2 | 3/2019 |
| WO | 2020198366 A1 | 10/2020 |
| WO | 2020227546 A1 | 11/2020 |
| WO | 2020255063 A1 | 12/2020 |
| WO | 2021021937 A1 | 2/2021 |
| WO | 2021034674 A1 | 2/2021 |
| WO | 2021133667 A1 | 7/2021 |
| WO | 2021189084 A1 | 9/2021 |
| WO | 2022025984 A1 | 2/2022 |
| WO | 2022064042 A1 | 3/2022 |

OTHER PUBLICATIONS

Paul et al., Development and validation of a broad scheme for prediction of HLA class II restricted T cell epitopes BCB '14: Proceedings of the 5th ACM Conference on Bioinformatics, Computational Biology, and Health Informatics Sep. 2014, pp. 733-738.*

Adamowicz et al., 2019, Interferon-Gamma Elispot Assay: Unique Challenges of Validating Immune Monitoring Assays in a Regulated Environment celerion Translating Science to Medicine pp. 1-4.

Carpenter et al., "A side-by-side comparison of T cell reactivity to fifty-nine Mycobacterium tuberculosis antigens in diverse populations from five continents", Tuberculosis (2015) 1-9.

Chinese Office Action dated Feb. 24, 2021 (English Translation) pertaining to related Chinese Application No. 101427135.

Gerdemann et al., "Immunotherapeutic strategies to prevent and treat human herpesvirus 6 reactivation after allogeneic stem cell transplantation", Blood, Jan. 3, 2013, vol. 121, No. 1, p. 207-218.

Goon et al., "Human T Cell Lymphotropic Virus (HTLV) Type-1—Specific CD8+ Cells: Frequency and Immunodominance Hierarchy", The Journal ol Infectious Diseases, Jun. 15, 2004; 189: 2294-2298.

Goon et al., "Human T Cell Lymphotropic Virus Type I (HTLV-I)-Specific CD4+ T Cells: fmmunodominance Hierarchy and Preferential Infection with HTLV-11", The Journal of Immunology, 2004, 172: 1735-1743.

Halawi et al., "Identification of novel CD8+ T cell epitopes in human herpesvirus 6B U11 and U90", Immunity, Inflammation and Disease 2015; 3(2): 118-131.

(56) References Cited

OTHER PUBLICATIONS

Herd et al., "Major Histocompatibility Complex Class I Cytotoxic T Lymphocyte Immunity to Human Metapneumovirus (hMPV) in ndividuals with Previous hMPV Infection and Respiratory Disease", The Journal ol Inlectious Diseases, Feb. 15, 2008; 197:584-92.

Janetzki et al., Guidelines for the automated evaluation of Elispot assays 1098-114 | vol. 10 No. 7 | 2015 | Nature Protocols.

Khan et al., "T Cell Recognition Patterns of Immunodominant Cytomegalovirus Antigens in Primary and Persistent Infection", The Journal of Immunology, 2007, 178: 4455-4465.

Leen, A. et al., "Differential Immunogenicity of Epstein-Barr Virus Latent-Cycle Proteins for Human CD4+ T-Helper 1 Responses," Journal of Virology, The American Society for Microbiology, vol. 75, No. 18, p. 8649-8659, Sep. 1, 2001.

Paul et al Development and validation of a broad scheme for prediction of HLA class II restricted T cell epitopes Journal of Immunological Methods 422 (2015) 28-34. Available online Apr. 7, 2015.

PepMix™ Peptide Pools; pp. 1-13 downloaded Feb. 13, 2021.

Peripheral blood mononuclear cell—Wikipedia; pp. 1-3; downloaded Sep. 3, 2020.

Ray et al., "Role of Individual Glycoproteins of Human Parainfluenza Virus Type 3 in the Induction of a Protective Immune Response", Journal of Virologoy, Mar. 1988, vol. 62, No. 3, pp. 783-787.

Seig et al., "Inforection and Immunoregulation of T Lymphocytes by Parainfluenza Virus Type 2", Proceedings of the National Academy of Sciences of the U.S. A., Jul. 1994, vol. 91, No. 14, pp. 6293-6297.

Tzannou et al., "Preventing Stem Cell Transplantation-associated Viral Infections using T-cell Therapy Immunotherapy", Immunotherapy, Aug. 7, 2015, vol. 7, No. 7, pp. 793-810.

Maecker et al., Journal of Immunological Methods, 2001, vol. 55, pp. 27-40.

Meij et al., Int J_ Cancer, 2002, vol. 99, pp. 93-99.

Merlo et al., "The interplay between Epstein-Barr virus and the immune system: a rationale for adoptive cell therapy of EBV-related disorders," Haematologica 95, 1769-77, 2010.

Merrick et al., "Autologous versus allogeneic peptide-pulsed dendritic cells for anti-tumour vaccination: expression of allogeneic MHC supports activation of antigen specific T cells but impairs early naive cytotoxic priming and anti-tumou therapy," Cancer Immunol. Immunother. 57, 897-906, 2008.

Mitchell Monica L et al: "Determination of Optimal Target Antigen and Immune Modulatory Approaches to Improve and Standardize Epstein-Barr Virus-Specific Adoptive T Cell Therapy", Blood, American Society of Hematology, US, vol. 124, No. 21, Nov. 14, 2014 (Nov. 14, 2014), p. 5817.

Montes et al., Optimum in vitro expansion of human antigen-specific CD8+ T cells for adoptive transfer therapy, Clinical and Experimental Immunology Jul. 12, 2005, 142: 292-302.

Morandi et al., "Tumor mRNA-Transfected Dendritic Cells Stimulate the Generation of CTL that Recognize Neuroblastoma-Associated Antigens, Kill Tumor Cells: Immunotherapeutic Implications", Neoplasia, Oct. 1, 2006, vol. 8, No. 10, pp. 833-842.

Muftuoglu et al., "Use of Expanded Allogeneic Third Party BK Vims Specific Cytotoxic C6. T Cells to Target Progressive Multifocal Leukoencephalopathy", Am. Soc. Hematol., abstract #98495, 128(22):3365, 2016.

Na et al., "Human Bone Marrow as a Source of Multifunctional CMV-Specific CD4+ T Cells for Adoptive Cell Therapy" Blood, 2007, vol. 110, p. 2973.

Nair et al., "Induction of tumor-specific cyototoxic T lymphocytes in cancer patients by autologous tumor RNA-transfected dendritic cells", Annals of Surgery, Apr. 1, 2002, vol. 235, No. 4, pp. 540-549.

Ngo, "Towards Phase 2/3 Trials for Epstein-Barr Virus (EBV)-Associated Malignancies," 2011 Graduate Student Symposium of the Graduate School of Biomedical Sciences at Baylor College of Medicine, p. 231, 2011.

Olson et al., "Efficacy of Third Party BK Vims (BKV) Specific Cytotoxic T-Lymphocytes Generated by Ex Vivo Expansion for the Treatment of BKV Infection in Stem Cell Transplant Recipients, a Phase 2 Trial", Am. Soc. Hematol., abstract, 128(22):504, 2016.

Papadopoulou et al. "Activity of broad-spectrum T-cells as treatment for AdV, EBV, CMV, BKV, and HHV6 infections after HSCT" Sci Transl Med. 2014: 6(242).

Quintarelli et al., "Cytotoxic T lymphocytes directed to the preferentially expressed antigen of melanoma (PRAME) target chronic myeloid leukemia", Blood, 112(5), pp. 1876-1885, Sep. 1, 2008 (Sep. 1, 2008).

R.J. Arasaratnam et al. "Dynamics of virus-specific T cell immunity in pediatric liver transplant recipients" Am J Transplant; Sep. 2018. 18(9): 2238-2249.

Ramaswami et al., Clin Vaccine Immunol, Published on line Mar. 2, 2011, vol. 18, No. 5 815-824.

Redchenko & Rickinson, "Accessing Epstein-Barr Virus-Specific T-Cell Memory with Peptide-Loaded Dendritic Cells," J. Virol. 73, 334-42, 1999.

Rudolf et al., "Potent costimulation of human CD8 T cells by anti-4-1BB and anti-CD28 on synthetic artificial antigen presenting cells," Cancer Immunol. Immunother. 57, 175-83, Epub 2007.

Suhoski et al., "Engineering artificial antigen-presenting cells to express a diverse array of co-stimulatory molecules," Mol. Ther. 15, 981-88, 2007.

Suneetha et al., Journal of Immunological Methods, 2009, vol. 342, No. 1-2, pp. 33-48.

Tan et al., A re-evaluation of the frequency of CD8+ T cells specific for EBV in healthy virus carriers, Journal of Immunology 1999; 162: 1827-1835.

Taylor et al., "Mechanisms of immune suppression by interleukin-10 and transforming growth factor-.beta.: the role of T regulatory cells," Immunology 117, 433-42, 2006.

Tekkatte, Chandana, et al.;" "Humanized" Stem Cell Culture Techniques: The Animal Serum Controversy"; Stem Cells Int'l, vol. 2011; Article ID 504723; 14 pgs; Nov. 9, 2010.

Testa et al: "MHC Class I-Presented T Cell Epitopes Identified by Immunoproteomics Analysis are Targets for a Cross Reactive Influenza-Specific T Cell Response", PLOS One, vol. 7, No. 11, Nov. 7, 2012 (Nov. 7, 2012), p. e48484.

The 23rd Annual Graduate Student Research Symposium of the Graduate School of Biomedical Sciences at Baylor College of Medicine, 2011, p. 231.

Trivedi et al., "Generation of CMV-specific T lymphocytes using protein-spanning pools of pp65-derived overlapping pentadecapeptides for adoptive immunotherapy", Blood, Apr. 1, 2005, vol. 105, No. 7, pp. 2793-2794.

Turtle & Riddell, "Artificial antigen presenting cells for use in adoptive immunotherapy," Cancer J. 16, 374-81, 2010.

Tzannou et al. ""Mini" bank of only 8 donors supplies CMV-directed T cells to diverse recipients," Blood Advances, Sep. 3, 2019 (Sep. 3, 2019), vol. 3, No. 17, pp. 2571-2580.

Tzannou et al. "Immunologic Profiling of Human Metapneumovirus for the Development of Targeted Immunotherapy" The Joural of Infectious Diseases; Sep. 2017, 216(6):678-687.

Tzannou et al. "Off-the-Shelf Virus-Specific T cells to Treat BK virus, human herpes virus 6, Cytomegalovirus, Epstein-Barr Virus, and Adenovirus Infections After Allogeneic Hematopoietic Stem-Cell Transplantation" Journal of Clinical Oncology; Nov. 2017, 35(31):3547-3557.

Van Montfoort et al., "Antigen storage compartments in mature dendritic cells facilitate prolonged cytotoxic T lymphocyte cross-priming capacity", PNAS, Apr. 21, 2009, vol. 106, No. 16, pp. 6730-6735.

Vasileiuou et al. "Rapid Generation of multivirus-specific T lymphocytes for the prevention and treatment of respiratory viral infections", Haematologica; 2020, vol. 105(1):235-243.

Vella et al., "Cytokine-induced survival of activated T cells in vitro and in vivo", Proc. Natl. Acad. Sci. USA 95, Immunology, Mar. 1998, vol. 95, pp. 3810-3815.

Vera, Juan F., et al; "Accelerated Production of Antigen-Specific T-cells for Pre-Clinical and Clinical Applications using Gas-

(56) References Cited

OTHER PUBLICATIONS

Permeable Rapid Expansion Cultureware (G-Rex)"; Journal of Immunotherapy, Apr. 2010, vol. 33, No. 3, pp. 305-315.
Withers et al. "Establishment and Operation of a Third-Party Virus-Specific T Cell Bank within an Allogeneic Stem Cell Transplant Program," Biology of Blood and Marrow Transplantation, Aug. 29, 2018 (Aug. 29, 2018), vol. 24, pp. 2433-2442.
Y E Z, et al; In Vitro expansion and Charcterization of Dendritic Cells Derived from Human Bon Marroe CD34+ Cells; Bone Marrow Transpaln, 1996, v 18. 997-1008.
Zhu et al. J. Gene. Virology, 2010, vol. 91, pp. 1577-1589.
Zirlik et al., Blood, Dec. 1, 2006, v.108 pp. 3865-3870.
Aguayo-Hiraldo et al. Characterizing the Cellular Immune Response to Parainfluenza Virus 3. The Joural of Infectious Diseases; Jul. 2017, 216(2):153-161.
Ando Jun et al "Towards Phase 2/3 Trials for Epstein-Barr Virus (EBV)-Associated Malignancies", Blood, vol. 118, No. 21, Nov. 2011, p. 1727.
Baugh et al. "Infusion of cytotoxic T lymphocytes for the treatment of viral infections in hematopoietic stem cell transplant patients" Curr Opin Infect Dis. Aug. 2018; 31(4): 292-300.
Bensussan et al. "Detection of membrane-bound HLA-G translated products with a specific monoclonal antibody", Proc. Natl. Acad. Sci. USA, 92:10292-10296, 1995.
Binggeli et al., American Journal of Transplantation, 2007, vol. 7, pp. 1131-1139.
Blyth et al., "Bk Vims Specific T Cells Expanded Ex Vivo for Use in Cellular Therapy Show Multiple Antigen Specificity and Polyfunctional THI Responses", abstract #164, S215.
Blyth et al., "BK Vims-Specific T Cells for Use in Cellular Therapy Show Specificity to Multiple Antigens and Polyfunctional Cytokine Responses", Transplantation, 92(10):1077-1084, 2011.
Blyth et al., in Blood, (Nov. 20, 2009) vol. 114, No. 22, pp. 962, Meeting Info.: 51st Annual Meeting of the American-Society-of-Hematology, New Orleans, LA, USA. Dec. 5-8, 2009, Amer Soc Hematol.
Britten et al., "The use of HLA-A*0201-transfected K562 as standard antigen-presenting cells for CD8+ T lymphocytes in IFN-? ELISPOT assays," J. Immunol. Methods 259, 95-110, 2002.
Burkett et al., IL-15R expression on CD8+ T cells is dispensable for T cell memory, PNAS Apr. 15, 2003, vol. 100, No. 8.
Calarota et al. "Detection of Epstein-Barr vires-specific memory CD4+T cells using a peptide-based cultured enzyme- linked immunospot assay", Immunology, 2013: 139: 533-544.
Can and Karahuseyinoglu, "Concise review: human umbilical cord stroma with regard to the source of fetus-derived stem cells", Stem Cells, 25:2886-2895, 2007.
Chakera et al., Clin Exp. Immunol2011, Sep. 156 (3): 401-409.
Chia, Whay-Kuang, et al; Adoptive T-Cell Transfer and Chemotherapy in the First-Line Treatement of Metastic and/or Locally Recurrent Nasopharyngeal Carcinoma; The Am. Society of Gene & Cell Therapy,; Molecular Therapy; pp. 1-8; Jul. 29, 2013.
Cornish et al., Differential regulation of T-cell growth by IL-2 and IL-15, Blood, Jul. 15, 2006, vol. 108, No. 2.
Dasari et al., "Prophylactic and therapeutic adenoviral vector-based multivims-specific Tcell immunotherapy for transplant patients", Mal. Ther., 3: 16058, 2016.
Decaussin et al., "Expression of BARF1 Gene encoded by Epstein-Barr Virus in Nasopharyngeal Carcinoma Biopsies," cancer Res. 60, 5584-88, 2000.
Dunne et al., "Selective Expansion and Partial Activation of Human NK Cells and NK Receptor-Positive T Cells by IL-2 and IL-15", Journal of Immunology, 2001, pp. 3129-3138.
Foster et al., "Autologous Designer Antigen-presenting Cells by Gene Modification of T Lymphocytes Blasts With IL-7 and IL-12," J. Immunother. 30, 506-16, 2007.
Fujita et al., "Exploiting cytokine secretion to rapidly produce multivirus-specific T cells for adoptive Immunotherapy", J Immunother., 2008, v 31, pp. 665-674.

Fujiwara et al., "Identification and in vitro expansion of CD4+ and CD8+ T cells specific for human neutrophil elastase", Blood, 103(8), pp. 3076-3083, Apr. 15, 2004 (Apr. 15, 2004).
Gaundar et al., "The Generation of Clinical Grade Aspergillus Fumigatus (AF) Specific Immune Cells for Adoptive Immunotherapy", abstract #168, S216.
Gerdeman et al., Blood, 2009, v. 114, Abstract 4083.
Gerdemann et al., "Cytotoxic T lymphocytes simultaneously targeting multiple tumor-associates antigens to treat EBV negative lymphoma", Molecular Therapy, Nature Publishing Group, GB, vol. 19, No. 12, Dec. 1, 2011, pp. 2258-2268.
Gerdemann et al., "Generation of Multivirus-specific T Cellls to Prevent/treat Viral Infections aftr Allogeneic Hematopoietic Stem Cell Transplant", Journal of Visualized Experiments, May 2011, vol. 51, e2736, pp. 1-6.
Gerdemann et al., "Multivirus-specific CTL for Adoptive Transfer Using In Vitro Pepmix Stimulation", Biology Blood Marrow Transplant, online Jan. 28, 2011, p. S216.
Gerdemann et al., "Nucleofection of DCs to Generate Multivirus-specific T Cells for Prevention or Treatment of Viral Infections in the Immunocompromised Host", Molecular Therapy, vol. 17, No. 9, Sep. 1, 2009, pp. 1616-1625.
Gerdemann et al., "Rapidly Generated Multivims-specific Cytotoxic T Lymphocytes for the Prophylaxis and Treatment of Viral Infections", Am. Soc. Gene Cell Ther., 20(8):1622-1632, 2012.
Gerdemann et al., "Safety and clinical efficacy of rapidly-generated trivirus-directed T cells as treatment for adenovirus, EBV, and CMV infections after allogeneic hematopoietic stem cell transplant", Molecular Therapy, vol. 2, No. 11, Jun. 20, 2013, pp. 2112-2121.
Geyeregger et al. "Short-Term In-Vitro Expansion Improves Monitoring and Allows Affordable Generation of Virus-Specific T-Cells against Several Viruses for a Broad Clinical Application" PLoS One, 2013, 8(4): e59592.
Heslop and Leen "T-cell therapy for viral infections" American Society of Hematology; 2013; 2013:342-7.
Hobeika et al., "Detailed analysis of cytomegalovirus (CMV)-specific T cells expanded for adoptive immunotherapy of CMV infection following allogeneic stem cell transplantation for malignant disease", Intl. Society for cellular Therapy, Cytotherapy, 2008, vol. 10, No. 3, pp. 289-302.
Huye et al., "Combing mTor Inhibitors With Rapamycin-resistant T Cells: A Two-pronged Approach to Tumor Elimination," Mol. Ther. 19, 2239-48, 2011.
Jeffes Ill et al. "Therapy of recurrent high grade gliomas with surgery, and autologous mitogen activated IL-2 stimulated killer (MAK) Lymphocytes: I. Enchancement of MAK lytic activity and cytokine production by PHA and clinical use of PHA" Journal of Neuro-Oncology, 1993, vol. 15, pp. 141-155.
Jennes et al., "Enhanced ELISPOT detection of antigen-specific T cell responses from cryopreserved specimens with addition of both IL-7 and IL-15 the Amplispot assay" Journal of Immunological Methods, 2002, vol. 270, pp. 99-108.
Jeras et al., "Induction/Engineering, Detection, Selection, and Expansion of Clinical-Grade Human Antigen-Specific CD8+ Cytotoxic T Cell Clones for Adoptive Immunotherapy," Journal of Biomedicine and Biotechnology, vol. 2010, Article ID 705215,2010, 15 pages.
Kedl et al; "T Cells Compete for Antigen-bearing Antigen-presenting Cells"; J.P. Med.—The Rockfeller University Press—vol. 192, No. 8, Oct. 16, 2002.
Kedl et al; "T Cells Down-Modulate Peptide-MHC Complexes on APCs in vivo"; Published online: Dec. 3, 2001, DOI: 10.1 038/ni/ 742; 2002 Nature Publishing Group.
Khanna et al., Blood, Jul. 2011, vol. 118, No. 4, pp. 1121-1131.
Kim et al., "The ABCs of artificial antigen presentation", Nature Biotechnology, 22(4), pp. 403-410, Apr. 2004 (Apr. 2004).
Lapteva and Vera "Optimization Manufacture of Virus- and Tumor-Specific T Cells", Stem Cells International, Apr. 26, 2011, vol. 2011, pp. 1-8.
Lee et al, HLA A2.1-restricted Cytotoxic T cells Recognizing a Range of Epstein-Barr Virus Isolates through a Defined Epitope in Latent Membrane Protein LMP2, Journal of Virology, Dec. 1993, p. 7428-7435.

(56) References Cited

OTHER PUBLICATIONS

Leen et al., "Cytotoxic lymphocyte (CTL) therapy for the treatment of EBV negative tumors", Abstract, International Society for Cell and Gene Therapy of Cancer Annual Meeting held in Cork, Ireland, presented Sep. 4, 2009.
Leen et al., "Identification of hexon-specific CD4 and CDS T-cell epitopes for vaccine and immunotherapy," Journal of Virology, 82(1):546-554, 2008.
Leen et al., "Overcoming antigenic competition to produce multispecific cytotoxic T lymphocyte lines for adoptive transfer," Poster, 6th Annual Dan L. Duncan Cancer Center Symposium, Baylor College of Medicine, Feb. 2009, No. 374, p. 134.
Leen et al., Nature Medicine, 2006, vol. 12, No. 10, pp. 1160-1166.
Leung et al. "Evaluation of cyclin A 1-specific T cells as a potential treatment for acute myeloid leukemia," Blood Adv, Jan. 28, 2020 (Jan. 28, 2020), vol. 4, pp. 387-397.
Liao et al., "Transfection of RNA encoding tumor antigens following maturation of dendritic cells leads to prolonged presentation of antigen and the generation of high-affinity tumor-reactive cytotoxic T lymphocytes", Molecular Therapy, May 1, 2004, vol. 9, No. 5, pp. 757-764.
Lim et al. Journal of Translational Medicine 2009, vol. 7:72, pp. 1-11.
Liu et al., IL-15 mimics T cell receptor crosslinking in the induction of cellular proliferation, gene expression and cytotoxicity in CD8+ memory T cells, PNAS Apr. 30, 2002, vol. 99, No. 9.
Pfeiffer T et al: "Posoleucel, an Allogeneic, Off-the-Shelf Multivirus-Specific T-Cell Therapy, for the Treatment of Refractory Viral Infections in the Post-HCT Setting", Clinical Cancer Research, vol. 29, No. 2, Jan. 17, 2023 (Jan. 17, 2023), pp. 324-330.
Vasileiou S et al: "Rapid Generation of Multivirus-Specific T Lymphocytes for the Prevention and Treatment of Respiratory Viral Infections", Blood, vol. 132, No. Suppl. 1, 3332, Nov. 29, 2018 (Nov. 29, 2018), XP086592710, 60th ASH Annual Meeting; San Diego, CA, USA; Dec. 1-8, 2018.
Vasileiou S et al: "Rapid Generation of Multivirus-Specific T Lymphocytes for the Prevention and Treatment of Respiratory Viral Infections", Biology of Blood and Marrow Transplantation, vol. 25, No. 3, 544, Mar. 2019 (Mar. 2019), p. S363, XP085593154, 2019 TCT Meetings of ASBMT and CIBMTR; Huston, TX, USA; Feb. 20-24, 2019.
Ahmed et al, "Preliminary Identification of Potential Vaccine Targets for the COVID-19 Coronavirus (SARS-CoV-2) Based on SARS-CoV Immunological Studies," Viruses 12(3):254, pp. 1-15 (2020).
AlloVir Announces Positive Final Results in Phase 2 Posoleucel Multi-Virus Prevention Study in Oral Presentation at the 64th ASH Annual Meeting and Exposition, Business Wire, Sonia Choi, AlloVir, Dec. 10, 2022, 3 pages.
Amary et al, "Detection of SS18-SSX fusion transcripts in formalin-fixed paraffin-embedded neoplasms: analysis of conventional RT-PCR, qRT-PCR and dual color FISH as diagnostic tools for synovial sarcoma," Modern Pathology 20:482-496 (2007).
Anonymous: "AlloVir", "2 Posoleucel (Viralym-M, ALVR105): A multi-virus specific T cell Therapy (VST) targeting five devastating viral pathogens," Jan. 18, 2022 (Jan. 18, 2022), XP093010987, Retrieved from the Internet: URL:https://web.archive.org/web/2022011810 ; 2142/https://www.a11ovir.com/products/alvr 105 [retrieved on Jan. 2, 2023], 6 pages.
Anthony et al., "Flow cytometry using annexin V can detect early apoptosis in peripheral blood stem cell harvests from patients with leukemia and lymphoma," Bone Marrow Transplant 21:441-446, 1998.
Arons et al., "Prame Expression in Hair Cell leukemia," Leukemia Research, New York, NY US 32(9):1400-1406 (2008).
Ben-Sasson et al., IL-1 acts directly on CD4 T cells to enhance their; antigen-driven expansion and differentiation, PNAS 106(17)7119-7124 (2009).
DeBoer et al, "Extensive early apoptosis in frozen thawed CD34+ stem cells decreases threshold doses for haematological recovery after autologous peripheral blood progenitor cell transplant," Bone marrow Transplant 29:249-255, 2002.
Bollard et al., "The generation and characterization of LMP2-specific CTL for use as adoptive transfer from patients with relapsed EBV-positive Hodgkin disease," J. Immunother. Jul.-Aug. 2004; 27(4):317-27.
Carrasco et al., "Vaccination of a Melanoma Patient with Mature Dendritic Cells Pulsed with MAGE-3 Peptides Triggers the Activity of Nonvaccine Anti-Tumor Cells," The Journal of Immunology 180(5):3585-3593 (2008).
Carrum et al., "Targeting Lymphomas Using Non-Engineered, Multi-Antigen Specific T Cells", Blood, American Society of Hematology US, vol. 132, Nov. 29, 2018 (Nov. 29, 2018), p. 1685.
Cha et al., "IL-7 + IL-15 are superior to IL-2 for the ex vivo expansion of 4T1 mammary carcinoma-specific T cells with greater efficacy against tumors in vivo ," Breast Cancer Res Treat. Jul. 2010, pp. 1-22.
CMD-003 / Cellular Immunotherapy Treatment Antigen-Directed for EBV Lymphoma (CITADEL), Cell Medica, Sep. 23, 2013, https://clinicaltrials.gov/ct2/show/NCT01948180.
Diao et al., "Reduction and Functional Exhaustion of T Cells in Patients with Coronavirus Disease 2019," Front. Immunol. 11:827, pp. 1-7 (2020).
Dienz and Rincon, "The Effects of IL-6 on CD4 T Cell Responses," Clin Immunol. Jan. 2009; 130(1): 27-33.
Fast et al., "Potential T-cell and B-cell Epitopes of 2019-nCOV," BIOrXIV, pp. 1-20 (2020).
Grifoni et al., "A Sequence Homology and Bioinformatic Approach Can Predict Candidate Targets for Immune Responses to SARS CoV-2," Cell Host & Microbe 27(40):671-680 (2020).
Hemmer et al., "Minimal peptide length requirements for CD4+ T cell clones-implications for molecular mimicry and T cell survival," International Immunology, vol. 12, No. 3, pp. 375-383 (2000).
Herd et al: "Cytotoxic T-Lymphocyte Epitope Vaccination Protects against Human Metapneumovirus Infection and Disease in Mice", Journal of Virology, Feb. 2006, vol. 80, No. 4, p. 2034-2044.
Hunder et al., "Treatment of Metastatic Melanoma with Autologous CD4+ t Cells Against NY-ESO-1," New England Journal of Medicine 358(25):2698-2703 (2008).
Jacobs et al., "Lab. Investigation-Human/Animal Tissue Selective Cancer-Germline Gene Expression in Pediatric Brain Tumors," J Neurooncol, pp. 273-280 (2008).
Keirnan et al., "PepMix™ Peptide Pools for Clinical Applications: T Cell Therapy for Viral Infections after Hematopoietic Stem Cell Transplant," JPT Peptide Technologies (2012), 2 pages.
Kelly-Rogers et al. Activation-Induced Expression of CD56 by T Cells is Associated With a Reprogramming of Cytolytic Activity and Cytokine Secretion Profile In Vitro. Human Immunology 67, 863-873 (2006).
Kikuta, Hideaki, "3. Human Metapneumovirus" Viruses, 2006, vol. 56, No. 2,p. 173-182.
Kindt et al., "Protective Role of the Inhibitor of Apoptosis Protein, Survivin, in Toxin-Induced Acute Renal Failure," The FASEB Journal, Federation of American Societies for Experimental Biology, US 22(2):510-521 (2008).
Koch CP, Perna AM, Pillong M, Todoroff NK, Wrede P, et al. (2013) Scrutinizing MHC-1 Binding Peptides and Their Limits of Variation. PLoS Comput Biol 9(6): e1 003088, 9 pages.
Kumar et al., "Structural, glycosylation and antigenic variation between 2019 novel coronavirus (2019-nCOV) and SARS coronavirus (SARS-COV)," Virusdisease 31(1):13-21 (2020).
Leen et al., "Contact-activated monocytes: efficient antigen presenting cells for the stimulation of antigen-specific T cells," J Immunother. Jan. 2007;30(1): 96-107.
Li et al, "T Cell Responses to Whole SARS Coronavirus in Humans," The Journal of Immunology 181(8):5490-5500 (2008).
Mielcarek et al., "Suppression of Alloantigen-Induced T-Cell Proliferation by CD14+ Cells Derived From Granulocyte Colony-Stimulating Factor-Mobilized Peripheral Blood Mononuclear Cells," Blood, vol. 89, No. 5 Mar. 1, 1997: pp. 1629-1634.
Nawa et al., "G-CSF reduces IFN-g and IL-4 production by T cells after allogeneic stimulation by indirectly modulating monocyte function," Bone Marrow Transplantation (2000) 25, 1035-1040.

(56) References Cited

OTHER PUBLICATIONS

Nelson et al., "Virus-specific T-cell therapy to treat BK polyomavirus infection in bone marrow and solid organ transplant recipients," Blood advances, pp. 5745-5754 (Nov. 20, 2020).
Parks et al., "Flow Cytometry and Fluorescence-Activated Cell Sorting (FACS)," Handbook of Experimental Immunology, Chapter 29, DM Weir (ed), Blackwell Scientific Publications, MA, 1986, xx pages.
PepTivator® CMV pp65—premium grade, MACS and Peptivator, Miltenyi Biotech GmbH 2013, 4 pages.
Professor Kronenberg Declaration filed in EP 12815750 Opposition on May 15, 2019, 75 pages.
Reyes et al., "Granulocyte colony-stimulating factor (G-CSF) transiently suppresses mitogen-stimulated T-cell proliferative response," British Journal of Cancer (1999) 80(1/2):229-235 (1999).
Rooney and Leen, "Moving Successful Virus-specific T-cell Therapy for Hematopoietic Stem Cell Recipients to Late Phase Clinical Trials," Molecular Therapy-Nucleic Acids (2012) I, e55, 4 pages.
Dadwal et al., "Posoleucel (ALVR105), an Off-the-Shelf, Multivirus-Specific T-Cell Therapy, for the Prevention of Viral Infections Post-Allogeneic Hematopoietic Cell Transplantation (allo-HCT): Results from an Open-Label Cohort of a Phase 2 Trial", Transplantation and Cellular Therapy, Elsevier, Amsterdam, NL, vol. 28, No. 3, Nov. 5, 2021 (Nov. 5, 2021), 2 pages.
Schmid et al., "Dead Cell Discrimination with 7-aminoactinomycin Din Combination with Dual Colour Immunofluorescence in Single Laser Flow Cytometry," Cytometry 13:204-208 (1992).
Schnittger et al., in Blood, CBL Mutations are Correlated with CMML, Frequently Associated with RUNX1 but Mutually Exclusive of JAK2V617F Mutations, Blood 114(22):962, 2 pages (Nov. 20, 2009).
Joshi et al., "Decreased immune functions of blood cells following mobilization with granulocyte colony-stimulating factor: association with donor characteristics," Blood 98(6): 1963-1970 (2001).
Sili et al., "Large-scale expansion of dendritic cell-primed polyclonal human cytotoxic T-lymphocyte lines using lymphoblastoid cells for adoptive immunotherapy," J. Immuother. May-Jun. 2003: 26(3): 241-56.
Song et al., "Detection of MAGE and SSX Gene Expressions by RT-nested PCR Using Common Primers in Head and Neck Cancer," Clinical and Experimental Otorhinolaryngology 1(2):97-102 (2008).
Teague et al., "Interleukin-IS rescues tolerant cos+ T cells for use in adoptive immunotherapy of established tumors," Nature Medicine 12(3):335-341 (2006).
Thevarajan et al., "Breadth of concomitant immune responses prior to patient recovery: a case report of non-severe COVID-19," Nature Medicine 26(4):453-455 (2020).
Tung et al., "Modern Flow Cytometry: A Practical Approach," Clin Lab Med 27(3):453 (2007), 15 pages.
Tzannou and Leen; Accelerating immune resconstitution after hematopoietic stem cell transplantation: Clinical & Translational Immunology 3:e11, pp. 1-10 (2014).
Vasileiou et al., "Allogeneic, Off-the-Shelf, Sars-Cov-2-Specific T Cells to Treat High-Risk Patients with COVID-19," Transplantation and Cellular Therapy 27, 3S, S1-S488, 3 pages (2021).
Zhou et al., Either IL-2 or IL-12 Is Sufficient to Direct Thl Differentiation by Nonobese Diabetic T Cells1, The Journal of Immunology, 2003, 170:735-740.
Dadwal, Sanjeet et al., Posoleucel (ALVR105), an Off-the-Shelf, Multivirus-Specific T-Cell Therapy, for the Prevention of Viral Infections Post-Allogeneic Hematopoietic Cell Transplantation (allo-HCT): Results from an Ope••abel Cohort of a Phase 2 Trial, Blood, vol. 138, Supplement 1, Nov. 23, 2021, p. 1760-1762. (Poster Abstracts).
Dadwal, Sanjeet et al., "Posoleucel (ALVR105), an Off-the-Shelf, Multivirus-Specific T-Cell Therapy, for the prevention of Viral Infections Post-Allogeneic Hematopoietic Cell Transplantation (allo-HCT): Results from an Ope••abel Cohort of a Phase 2 Trial," 16 pages. Retrieved from <https://docs.publicnow.com/viewDoc?hash_primary=174944531E2578BE2113C21656B176A3520CC307>, 2022.
Diao et al: "Reduction and Functional Exhaustion of T Cells in Patients with Coronavirus Disease 2019 (COVID-19)", medRxiv, Feb. 20, 2020 (Feb. 20, 2020).
EP Search Report dated Apr. 4, 2023 cited in related EP Appl. No. 20777790.5.
EP Search Report dated dated Oct. 16, 2019 cited in related EP Appl. No. 19178235.8.
EP Search Report dated Feb. 7, 2013 cited in related EP Appl. No. 10814245.6.
EP Search Report dated Jul. 20, 2015 in related EP Appl. No. 13746524.1.
EP Search Report dated Mar. 20, 2019 during examination of in related EP Appl. No. 16847545.7.
EP Search Report dated May 21, 2021 cited in related EP Appl. No. 21160943.
EP Search Report dated Oct. 10, 2022 cited in related EP Appl. No. 22166731.
EP Search Report dated Sep. 27, 2016 in related EP Appl. No. 16180607.0.
Hasskarl et al."Induction of graft versus malignancy effect after unrelated allogeneic PBSCT using donor lymphocyte infusions derived from frozen aliquots of the original graft", Bone Marrow Transplantation, vol. 47, No. 2, Apr. 4, 2011 (Apr. 4, 2011), pp. 277-282.
International Preliminary Report on Patentability and Written Opinion issued for Application No. PCT/GB2012/053113, dated Feb. 10, 2014.
International Preliminary Report on Patentability for Application No. PCT/US2020/044080, dated Feb. 1, 2022.
International Preliminary Report on Patentability issued by the International Searching Authority for Application No. PCT/US2016/052487, dated Mar. 20, 2018.
International Preliminary Report on Patentability issued in International Application No. PCT/GB2012/050896 dated Jun. 17, 2014.
International Preliminary Report on Patentability issued in International Application No. PCT/GB2012/053114, dated Jun. 17, 2014.
International Preliminary Report on Patentability issued in International Application No. PCT/US2010/025209, dated Sep. 9, 2011.
International Preliminary Report on Patentability issued in International Application No. PCT/US2013/025342, dated Aug. 12, 2014.
International Preliminary Report on Patentability issued in International Application No. PCT/US2020/024726, dated Sep. 28, 2021.
International Preliminary Report on Patentability issued in International Application No. PCT/US2020/065968, dated Jun. 28, 2022.
International Preliminary Report on Patentability issued in International Application No. PCT/US2021/016266, dated Jan. 31, 2023.
International Search Report and Written Opinion issued by the International Searching Authority for Application No. PCT/IB2022/061291, dated Mar. 29, 2023.
International Search Report and Written Opinion dated Aug. 10, 2012 in PCT/GB2012/050896.
International Search Report and Written Opinion dated Mar. 23, 2021 issued during examination of International Application No. PCT/US2020/065968.
International Search Report and Written Opinion issued by the International Searching Authority for Application No. PCT/US2020/044080, dated Oct. 28, 2020.
International Search Report and Written Opinion issued in International Application No. PCT/US2010/025209, dated Jul. 14, 2010.
International Search Report and Written Opinion issued in International Application No. PCT/US2016/052487, dated Dec. 19, 2016.
International Search Report and Written Opinion issued in International Application No. PCT/US2020/024726, dated Jun. 19, 2020.
International Search Report and Written Opinion issued in International Application No. PCT/US2021/016266, dated Jun. 4, 2021.
International Search Report by the International Searching Authority for Application No. PCT/GB2012/053113, dated Mar. 26, 2013.
International Search Report issued in International Application No. PCT/GB2012/053114, dated Jul. 15, 2013.
International Search Report issued in International Application No. PCT/US2013/025342, dated Aug. 11, 2013.
International Search Report dated Jun. 29, 2021 during examination of International Application No. PCT/US2021/070291.

(56) References Cited

OTHER PUBLICATIONS

Olson et al., "Third-Party BK Virus-Specific Cytotoxic T Lymphocyte Therapy for Hemorrhagic Cystitis Following Allotransplantation," J Clin Oncol 39:2710-2719 (2021).

Peggs et al "Directly Selected Cytomegalovirus-Reactive Donor T Cells Confer Rapid and Safe Systemic Reconstitution of Virus-Specific Immunity Following Stem Cell Transplantation", Clinical Infectious Diseases, vol. 52, No. 1, Jan. 1, 2011 (Jan. 1, 2011), pp. 49-57.

Samuel et al "CMV-reactive T cells can be isolated from G-CSF mobilised peripheral blood apheresates", Blood, vol. 116, No. 21, Nov. 19, 2010 (Nov. 19, 2010).

Samuel et al "Successful isolation and expansion of CMV-reactive T cells from G-CSF mobilized donors that retain a strong cytotoxic effector function", British Journal of Haematology, vol. 160, No. 1, Oct. 9, 2012 (Oct. 9, 2012), pp. 87-100.

Wing et al., "An Improved Method for the Detection of Cell Surface Antigens in Samples of Low Viability using Flow Cytometry," J Immunol Methods 126: 21-27 1990.

Written Opinion issued in International Application No. PCT/US2013/025342, dated Apr. 11, 2013.

Blyth et al.: "Donor-derived CMV-specific T cells reduce the requirement for CMV-directed pharmacotherapy after allogeneic stem cell transplantation", Blood, May 2, 2013 x vol. 121, No. 18, The American Society of Hematology.

Gottlieb et al: "Prophylactic antigen-specific T-cells targeting seven viral and fungal pathogens after allogeneic haemopoietic stem cell transplant", Clinical & Translational Immunology 2021; e1249.

Itoh et al., Nishinihon J of urology, 1998, v.60 pp. 185-190.

Micklethwaite et al: "Ex Vivo Expansion and Prophylactic Infusion of CMV-pp65 Peptide-Specific Cytotoxic T-Lymphocytes following Allogeneic Hematopoietic Stem Cell Transplantation", Biology of Blood and Marrow Transplantation 13:707-714 (2007), American Society for Blood and Marrow Transplantation.

AlloVir, "Moltiviros-specific T Cells for the Treatment of Virus Infections After Stem Cell Transplant (Charms)" Study Record—ClinicalTrials.gov, May 29, 2019 (May 29, 2019).

European Supplemental Search Report dated Jul. 24, 2023 during examination of EP Appl. No. 20847823.0.

\* cited by examiner

| T cell response to hMPV | | | |
|---|---|---|---|
| Antigen | (+) % | (-) % | Magnitude SFC/2x10⁵ |
| SH | 3.4 | 96.6 | 34 |
| M | 79.3 | 20.7 | 154±24 |
| L | 44.8 | 55.2 | 125±22 |
| G | 31.0 | 69.0 | 62±18 |
| F | 96.5 | 3.5 | 300±52 |
| M2-2 | 0 | 0 | 0 |
| P | 68.9 | 31.1 | 130±24 |
| M2-1 | 79.3 | 20.7 | 167±21 |
| N | 86.2 | 13.8 | 220±33 |

FIG. 17

| Antigen | (+) % | (-) % | Magnitude SFC/2x10⁵ | TC-score | rank |
|---|---|---|---|---|---|
| SH | 3.4 | 96.6 | 34 | 1.53 | 8th |
| M | 79.3 | 20.7 | 154±24 | 569.87 | 4th |
| L | 44.8 | 55.2 | 125±22 | 101.87 | 6th |
| G | 31.0 | 69.0 | 62±18 | 28.34 | 7th |
| F | 96.5 | 3.5 | 300±52 | 6500 | 1st |
| M2-2 | 0 | 0 | 0 | 0 | 9th |
| P | 68.9 | 31.1 | 130±24 | 283.08 | 5th |
| M2-1 | 79.3 | 20.7 | 167±21 | 617.97 | 3rd |
| N | 86.2 | 13.8 | 220±33 | 1178.38 | 2nd |

T cell response to hMPV

FIG. 18

T cell response to PIV-3

| Antigen | (+) % | (−) % | Magnitude SFC/2×10⁵ |
|---|---|---|---|
| HN | 88.2 | 11.8 | 131 ± 18 |
| Protein C | 47 | 53 | 214.6 ± 31 |
| PP | 47 | 53 | 203.7 ± 25 |
| Large | 47 | 53 | 115.8 ± 16 |
| M | 94.1 | 5.9 | 261.2 ± 28 |
| N | 64.7 | 35.3 | 160 ± 19 |
| Fusion | 47 | 53 | 175.7 ± 26 |

FIG. 21

T cell response to PIV-3

| Antigen | (+) % | (-) % | Magnitude SFC/2x10⁶ | TC-score | rank |
|---|---|---|---|---|---|
| HN | 88.2 | 11.8 | 131 ± 18 | 912.91 | 2nd |
| Protein C | 47 | 53 | 214.6 ± 31 | 190.76 | 4th |
| PP | 47 | 53 | 203.7 ± 25 | 181.07 | 5th |
| Large | 47 | 53 | 115.8 ± 16 | 102.93 | 7th |
| M | 94.1 | 5.9 | 261.2 ± 28 | 3600.02 | 1st |
| N | 64.7 | 35.3 | 160 ± 19 | 289.59 | 3rd |
| Fusion | 47 | 53 | 175.7 ± 26 | 156.18 | 6th |

FIG. 22

| Antigen | Granzyme B ||| n=13 |
| | (+) % | (-) % | Magnitude SFC/2x10⁵ | TC-score |
| --- | --- | --- | --- | --- |
| F | 12 | 88 | 103±27 | 1113 |
| M | 12 | 88 | 42±8 | 454 |
| M2-1 | 10 | 90 | 92±18 | 299 |
| P | 8 | 92 | 44±15 | 70 |

FIG. 24

Product use $HLA_P$ vs $HLA_{Pt} \geq 1 = 1_{(Th)}$ $HLA_P$ vs $HLA_{Pt} < 1 = 0_{(Th)}$ $[(_RTB)+(_RTK)] \times Th \geq 1$ → Product is given to patient $[(_RTB)+(_RTK)] \times Th < 1$ → Product is NOT given to patient

IMMUNOGENIC ANTIGEN IDENTIFICATION FROM A PATHOGEN AND CORRELATION TO CLINICAL EFFICACY

CROSS-REFERENCE TO RELATED APPLICATIONS

This application is a continuation of U.S. Non-Provisional patent application Ser. No. 15/759,501 filed Mar. 12, 2018, now U.S. Pat. No. 11,167,024, which is a national phase application under 35 U.S.C. § 371 that claims priority to International Application No. PCT/US2016/052487 filed Sep. 19, 2016, which claims priority to U.S. Provisional Patent Application Ser. No. 62/220,884 filed Sep. 18, 2015, all of which applications are incorporated by reference herein in their entirety.

TECHNICAL FIELD

Embodiments of the disclosure concern at least the fields of cell biology, molecular biology, immunology, and medicine.

BACKGROUND

Hematopoietic stem cell transplant (HSCT) is the treatment of choice for a variety of malignant and non-malignant disorders. Post-transplant, however, graft versus host disease (GVHD), primary disease relapse and viral infections remain major causes of morbidity and mortality. Viral infections are detected in the majority of allograft recipients. Although available for some viruses, antiviral drugs are not always effective, highlighting the need for novel therapies. One strategy to treat these viral infections is with adoptive T cell transfer, including at least infusion of donor-derived virus-specific T cells (VSTs), for example. With a VST approach, one can extract cells from a donor, expand virus-specific populations ex vivo and, finally, infuse the T cell product into the stem cell transplant recipient, for example.

In vitro expanded donor-derived and $3^{rd}$ party VSTs targeting Adv, EBV, CMV, BK, HHV6 have shown to be safe when adoptively transferred to stem cell transplant patients with viral infections. VSTs reconstituted antiviral immunity for Adv, EBV, CMV, BK and HHV6, were effective in clearing disease, and exhibited considerable expansion in vivo. Adoptively transferred in vitro expanded autologous cancer-specific T cells have also been shown to be safe and associated with clinical benefit when adoptively transferred to patients.

Embodiments of the present disclosure satisfy a long-felt need in the art by providing therapies for certain pathogens and cancer antigens, and also for identifying which antigens are immunogenic and clinically efficacious.

BRIEF SUMMARY

Embodiments of the disclosure concern methods, compositions, and/or systems for generating immunotherapies, including for identifying one or more antigen(s) that would be clinically efficacious in one or more immunotherapies for a mammalian individual, such as a human or a dog. Embodiments of the methods concern determining which antigens from a pathogen or cancer cell are suitably immunogenic to be utilized for one or more therapeutic applications in a mammal. In certain embodiments the pathogen is a virus, bacteria, or fungi, for example.

In particular embodiments, methods of the disclosure concern the determination of the immunogenicity for a plurality of antigens from a pathogen and/or cancer cell in question and concern an ordering of the immunogenicity based on a suitable biological determination. The determination of a hierarchy of the antigens based on their immunogenicity can be utilized in considering a suitable immunogenic therapy for an individual that has the pathogen or cancer and that is susceptible or at risk for exposure and/or disease from the pathogen and/or cancer. In specific embodiments, the suitable immunogenic therapy comprises the most suitable immunogenic therapy based on the immunodominance of antigens for a particular pathogen or cancer.

In various embodiments at least two antigens from a pathogen or cancer are identified and their level of immunogenicity is quantitated. The antigens can then be ranked in order based upon their level of immunogenicity so that a determination can be made as to which of the antigens should be used a target for an immunotherapy.

The immunogenic therapy designed based on the determination of the hierarchy of antigens may be of any kind, but in specific embodiments the immunogenic therapy comprises vaccines, adoptive cell therapy, monoclonal antibody, bi-specific antibodies (BITES), oncolytic virus, or a combination thereof. The immunotherapy may comprise adoptive T cell therapy (native T cell receptor (TCR), engineered TCRs, or CAR T cells), although other types of immune cells may be utilized, including NK cells, NK T cells, mesenchymal stromal cells (MSCs), and dendritic cells (DC). The immunotherapy may rely on the production and use of immune cells including those that rely on T cell receptors that are native or engineered and those that rely on NK cells, NKT cells, mesenchymal stromal cells (MSCs), and dendritic cells (DCs). For example, a T cell therapy can be designed that attacks at least two of most immunogenic antigens of a pathogen or cancer with the intent of destroying a respective pathogenic cell or a cancer cell. Such a therapy could include a T cell manufacturing process that generates T cells that are able to recognize at least two of the most immunogenic antigen targets from a pathogen or cancer. In alternative embodiments, the T cell therapy targets only one antigen from a pathogen or cancer.

In certain embodiments, the immunogenicity of more than one antigen from a pathogen or a cancer is determined and is ordered into a hierarchy for use in considering the one or more antigens to be utilized in therapy for an individual that has been exposed to the pathogen (including has contracted a disease caused directly or indirectly by the pathogen), or may be exposed to the pathogen, or who has cancer or is at risk of developing cancer, or as a result of being exposed to the pathogen is at risk of developing cancer.

In specific embodiments, evaluations are undertaken to build an information base that can be used to assign a value to the level of immunogenicity of a given antigen. The information base is established as follows: a) peripheral blood mononuclear cells (PBMCs), obtained from pathogen exposed individuals or cancer patients, undergo an in vitro culture process that exposes the PBMCs to two or more antigens from the pathogen or two or more antigens from the cancer, preferably in the presence of Th-1 polarizing cytokines; b) a period of time is allowed to let T cells that recognize the antigens multiply in quantity; c) the culture is split into as many separate cultures as the number of antigens that were present in step a and only one of the antigens is added into each culture, each culture thereby including one of the original antigens and each culture including an antigen that differs from the other cultures; d)

biological activity is measured (which may be referred to as a biological measurement); e) either in parallel or at a different time, perhaps becoming a historic reference, a threshold for biological activity is established by an in vitro assessment of the biological activity occurring in PBMCs that have not been exposed sequentially or in parallel in vitro to the same agent(s) of step c; f) the biological activity of each of the cultures of step c is compared to the threshold and those that have biological activity that exceeds the threshold are classified as responders and those that do not have biological activity that exceeds the threshold are classified as non-responders and g) as a result of steps a-f the frequency of responders and non-responders relative to the number individuals evaluated is known and the magnitude of the responders biological activity relative to the threshold and relative to zero is known.

Skilled artisans recognize that in specific aspects a threshold is the noise in the process of measuring biological activity. There is more than one way to establish the threshold. For example, as described above, PBMCs can be exposed to each antigen used in the process and the subsequent biological activity can be measured to establish the threshold. Alternatively for example, the cultures of step c can also be challenged with an antigen that is not included in step a. Both approaches will detect noise and thereby establish the threshold that needs to be exceeded for the culture that is exposed to the antigen of interest to be classified as a responder.

In certain embodiments, there is a method of characterizing immunogenic antigens for a pathogen or cancer, comprising the steps of providing or generating multiple pluralities of T cells, wherein each plurality of T cells is specific for one antigen from the pathogen or cancer; assaying for a quantifiable biological response from cells from each plurality upon challenge from their respective antigens, wherein a quantitated output of the biological response is measured against a threshold quantity to determine the efficacy and magnitude of the response from each plurality, wherein the efficacy is the percentage of individuals in a population that have a biological response that exceeds the threshold quantity; and ordering the immunogenicity of each antigen based on a mathematical relationship between the efficacy and magnitude of the response from each plurality.

In other embodiments, a formula is established that uses variables including the percentage of responders and the percentage of non-responders as well as the magnitude of the biological response to assign a value to an antigen, the higher the value the higher the level of immunogenicity assigned to a particular antigen.

In other embodiments, a formula is established that uses variables including the percentage of responders and the percentage of non-responders as well as the magnitude of the biological response to assign a value to an antigen, the higher the value the higher the level of immunogenicity assigned to a particular antigen.

Provided herein are examples of methods of immune profiling of exemplary Virus X, Bacteria Y, Tumor Z and also of specific but exemplary viruses, such as parainfluenza type III (PIV3) and human Metapneumovirus (hMPV). In specific embodiments, the immunogenicity of multiple antigens for PIV3 and hMPV are respectively determined and utilized in therapy.

In particular embodiments, the methods and compositions of the disclosure concern adoptive T-cell therapy to prevent or treat infection. such as following HSCT. In particular cases, the disclosure includes therapy for the prevention or treatment of viral infection, including at least for infection by PIV (including at least PIV3), hMPV, cytomegalovirus, BK virus, human herpesvirus 6, adenovirus, Epstein Barr virus, BK virus, RSV, Influenza, Parainfluenza, Bocavirus, Coronavirus, LCMV, Mumps, Measles, Metapneumovirus, Parvovirus B, Rotavirus, West Nile Virus, JC, or HHV7, for example. Viruses from any viral infection may be treated, including from one of the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, or Togaviridae.

Bacteria that may comprise the pathogen of interest include at least the following: *Bacillus anthracis, Bacillus cereus, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica*, or *Yersinia pseudotuberculosis*, for example.

In particular embodiments, the methods and compositions of the disclosure also concern adoptive T-cell therapy to prevent or treat cancer, including cancer that is selected from the group consisting of Acute Lymphoblastic Leukemia (ALL), acute Myeloid Leukemia (AML), Adrenocortical Carcinoma, Adrenal Cortex Cancer, AIDS-Related Cancers, Kaposi Sarcoma, AIDS-Related Lymphoma, Primary CNS Lymphoma, Anal Cancer, Appendix Cancer, Astrocytomas, Atypical Teratoid/Rhabdoid Tumor, Basal Cell Carcinoma, Bile Duct Cancer, Bladder Cancer, Bone Cancer (including Ewing Sarcoma and Osteosarcoma and Malignant Fibrous Histiocytoma), Breast Cancer, Bronchial Tumors, Burkitt Lymphoma, Gastrointestinal Carcinoid Tumor, Carcinoid Tumors, Cardiac (Heart) Tumors, Embryonal Tumors, Germ Cell Tumors, Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal, Esthesioneuroblastoma, Extracranial Germ Cell Tumor, Extragonadal Germ Cell Tumor, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Extracranial Germ Cell Tumor, Extragonadal Germ Cell Tumor, Ovarian Cancer, Testicular Cancer, Gestational Trophoblastic Disease Gliomas, Hairy Cell Leukemia, Head and Neck Cancers, Heart Tumors, Hepatocellular Cancer, Langerhans Cell Histiocytosis, Hodgkin Lymphoma, Hypopharyngeal Cancer, Intraocular Melanoma, Islet Cell Tumors, Pancreatic Neuroendocrine Tumors, Pancreatic Cancer, Kaposi Sarcoma, Laryngeal Cancer, Laryngeal Papillomatosis, Leukemia, Lip and Oral Cavity Cancer, Liver Cancer, Lung Cancer, Non-Hodgkin Lymphoma, Malignant Fibrous Histiocytoma of Bone, Osteosarcoma, Melanoma, Intraocular Melanoma, Merkel Cell Carcinoma, Skin Cancer, Mesothelioma, Malignant Mesothelioma, Metastatic Squamous Neck Cancer with Occult Primary, Midline Tract Carcinoma Involving NUT Gene, Mouth Cancer-Head and Neck Cancer, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myeloproliferative Neoplasms, Myelogenous Leukemia, Chronic (CML), Nasal Cavity and Paranasal Sinus Cancer, Nasopharyngeal Cancer, Neuroblastoma, Non-Hodgkin Lymphoma, Non-Small Cell Lung Cancer, Oral Cancer, Lip and Oral Cavity Cancer, Oropharyngeal Cancer, Oral Cavity Cancer, Osteosarcoma, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Peritoneal Cancer, Prostate Cancer, Rectal Cancer, Colorectal Cancer, Renal Cell (Kidney) Cancer, Retinoblastoma, Rhabdomyosarcoma, Salivary Gland Cancer, Salivary Gland Tumors, Sarcoma, Osteosarcoma, Rhabdomyosarcoma, Uterine Sarcoma, Uterine Cancer, Vascular Tumors, Sézary Syndrome, Skin Cancer, Small Cell Lung Cancer, Small Intestine Cancer, Soft Tissue Sarcoma, Squamous Cell Carcinoma, Squamous Neck Cancer, Stomach (Gastric) Cancer, Cutaneous T-Cell Lymphoma, Testicular Cancer, Throat Cancer, Thymoma, Thymic Carcinoma, Thyroid Cancer, Thyroid Tumors, Transitional Cell Cancer of the Renal Pelvis and Ureter, Urethral Cancer, Uterine Cancer, Endometrial, Uterine Sarcoma, Vaginal Cancer, Vascular Tumors, Vulvar Cancer, Waldenström Macroglobulinemia (Non-Hodgkin Lymphoma) and Wilms Tumor.

Other and further objects, features, and advantages would be apparent and eventually more readily understood by reading the following specification and be reference to the accompanying drawings forming a part thereof, or any examples of the presently preferred embodiments of the invention given for the purpose of the disclosure.

BRIEF DESCRIPTION OF THE DRAWINGS

FIG. 17 shows one example of a T cell response to hMPV.

FIG. 18 shows one example of a T cell response to hMPV including an antigen hierarchy.

FIG. 21 provides one example of a T cell response to PIV3.

FIG. 22 shows one example of a T cell response to PIV3 including an antigen hierarchy.

FIG. 24 demonstrates an example where Granzyme B is used to determine a percentage of responders vs. non-responders for the characterization of an immune response against a pathogen.

DETAILED DESCRIPTION

Figure 1:
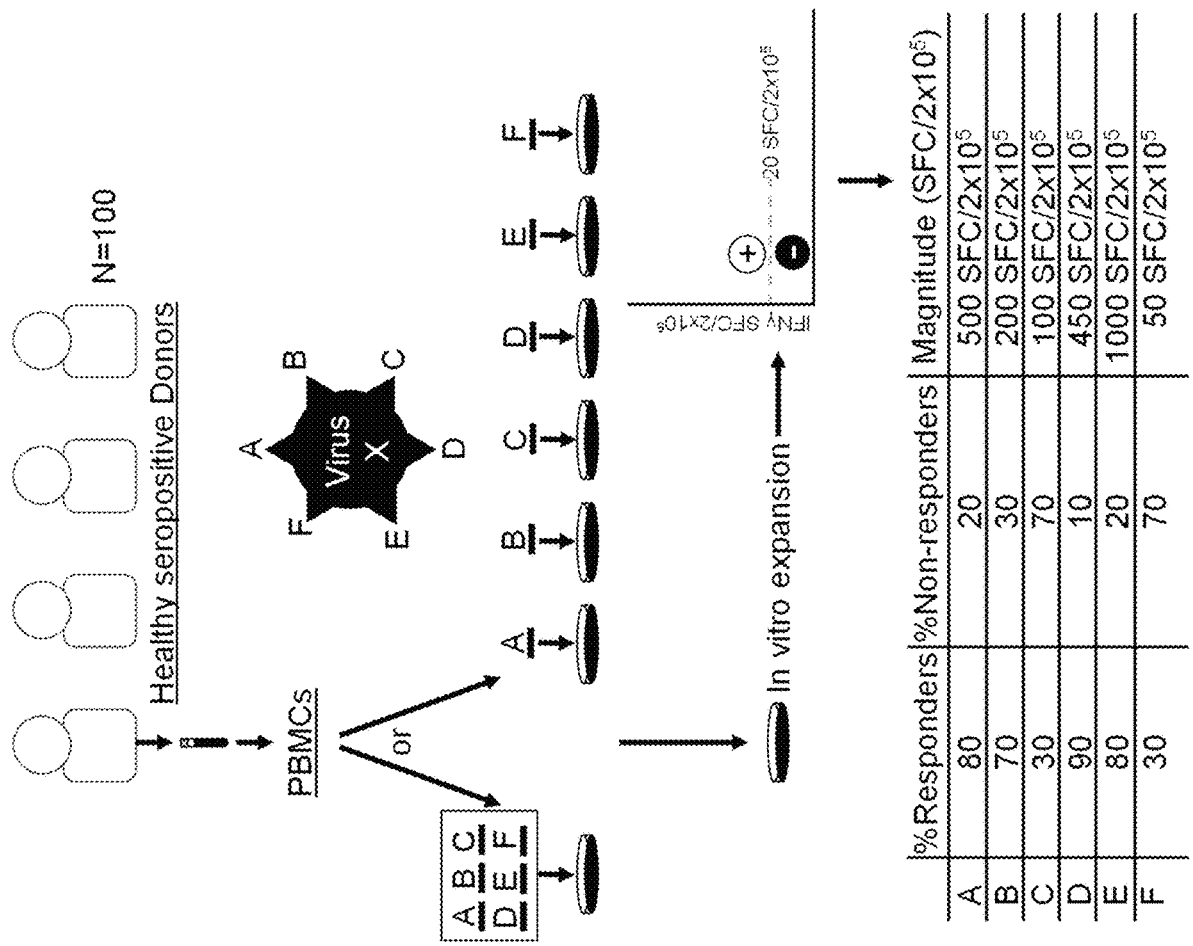
FIG. 1 illustrates an example of immunogenic antigen identification for an exemplary Virus X including exposing PBMCs to multiple antigens followed by re-challenge and determination of a threshold and identification of responders and non-responders.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "biological activity" is defined as a biological change in the production of effector molecules, such as IFN gamma, granzyme B, IL2, TNF alpha, specific lysis of target cells, or expression of cell surface molecules such as CD25, CD69, CD27, CD28, or CD107 a/b, for example.

I. General Embodiments

In some embodiments of the disclosure, an individual is in need of the methods and/or compositions of the disclosure. In specific embodiments, the individual is immunocompromised (which for example, may be defined as an individual whose ability to fight infectious disease with the immune system is compromised or entirely absent for any reason). In specific embodiments, the immunocompromised individual has had a stem cell transplant, has had an organ transplant, and so forth. In another specific embodiment, the individual has cancer or is at risk of developing cancer.

Embodiments of the disclosure concern the establishment of a hierarchy of immunodominance for a pathogen or cancer, and in representative cases the pathogen is PIV (including at least PIV3), hMPV, cytomegalovirus, BK virus, human herpesvirus 6, adenovirus, Epstein Barr virus, BK virus, RSV, Influenza, Parainfluenza, Bocavirus, Coronavirus, LCMV, Mumps, Measles, Metapneumovirus, Parvovirus B, Rotavirus, West Nile Virus, JC, or HHV7. Cancer antigens may be from cancer of the lung, breast, brain, colon, skin, prostate, pancreas, endometrium, kidney, ovary, testes, bone, spleen, liver, gall bladder, thyroid, esophagus, intestine, bladder, rectum, anus, stomach, head and neck, throat, pituitary gland, or multiple myeloma or lymphoma, for example. In specific embodiments, when the pathogen is a virus, examples of thresholds of activity for distinguishing responders and non-responder is a value above 20 IFN gamma spot-forming cells (SFC)/$2 \times 10^5$ input cells or 10 granzyme B SFC/$2 \times 10^5$ input cells in ELIspot assays. One skilled in the art recognizes that these represent examples of biological activity used to define thresholds of activity. However, the examples of numerical thresholds to define biological activity are subject to change depending on the assays/tools used to measure biological activity.

In particular embodiments, one or more quantitative biological responses are utilized in a determination for rank of immunogenicity of antigens from a pathogen. In specific embodiments, the response is utilized to identify a critical level of T cell activity, including a level that can be used to determine responders vs. non-responders. In certain embodiments, a quantitative biological response is the production (such as secreted from the cell) or expression (such as membrane-bound on the cell) of a compound from T cells upon recognition of a particular target. In specific embodiments, the compound is IL1α, IL1β, IL-2, IL-3, IL-4, IL-5, IL-6, IL-9, IL-10, IL-12 (p35+p40), IL-13, IL-14, IL-15, IL-16, IL-17a, IL-17B, IL-17F, IL-18, IL-19, IL-20, IL-21, IL-22, IL-23 (p90+p43), IL-25, IL-26, IL-27 (p28+EBI3), IL-28A/B/IL29A, IL-30 (p28 subunit of IL-27), IL-31, IL-32, IL-33, IL-35 (p35+EBI3), TNFα, LTα, LTβ, LIGHT, OX40L, CD25, CD45, CD40L, FASL, CD27L, CD30L, 4-1BBL, TRAIL, RANK Ligand, GM-CSF, IFNγ, LIF, MIF, TGFβ1, TGFβ2, and/or TGFβ3. In specific embodiments, the compound is IL2, IFNγ, granzyme B, CD25, perforin, GM-CSF, and/or TNFα. In some embodiments, the biological response is the upregulation of one or more markers upon stimulation with a cognate antigen, such as CD25, CD27, CD28, CD45, CD69, and/or CD107.

The skilled artisan recognizes that the term SFC is utilized in reference to Enzyme-linked immunosorbent spot (ELIspot) technique that identifies cells that express or secrete a particular compound of interest. The technique employs the use of target protein-specific antibodies immobilized on suitable membranes. Compounds produced by cells of interest plated at varying densities are captured by a first antibody that recognizes the compound and then visualized by a second labeled antibody also specific for the compound. The enumeration of this reaction is a biomarker for certain methods disclosed herein.

II. Identification of Immunogenic Antigens and Efficacy Order Thereof

Particular embodiments of the disclosure provide methods and compositions related to the identification of immunogenic antigen(s) that are particularly suitable for generation of and/or utilization in one or more types of immunotherapies. In specific embodiments, in a collection of antigens one or more antigens from the collection are identified as being more immunogenic than other antigen(s). The collection of antigens may be multiple antigens from the same entity, such as from the same pathogen or from the same cancer type (including tumor antigens). In some cases, the collection of antigens include some or a majority of possible antigens from a pathogen or a cancer, and in certain cases the collection of antigens comprise all possible antigens from a pathogen or a cancer. The pathogen may be a virus, bacteria, or fungus, for example.

In general embodiments, a range of immunogenicity for a variety of antigens from a pathogen or cancer is ordered after at least a first and second challenge with the antigens to T cells, followed by determination of a mathematical value that reflects the effectiveness of response of the T cells, wherein the determination occurs after the second or a subsequent challenge. As an example, T cells from individuals are stimulated in vitro with a collection of antigens, and this initial stimulation can occur either with the different antigens being pooled for exposure to the T cells or with the different antigens being separated for exposure to the T cells. The stimulation may or may not occur in the presence of Th1-polarizing cytokines, in certain cases. Following a suitable amount of time (for example, 2, 3, 4, 5, 6, 7, 8, 9, 10, 11, or 12 days), the T cells are subjected to a second challenge, but in the second challenge the T cells are exposed to the different antigens in a separated manner (not pooled). Following a suitable amount of time (for example, 15 mins-72 hours), one or more biological responses of the T cells are evaluated, such as in a quantitative fashion. For example, as a biological response one can assess the production of one or more certain compound(s) (including produced and secreted from the cell or produced for cell surface expression, for example) as a measure of the activity of the T cells. The measurements may occur following a certain period of time after exposing the T cells to the second or subsequent challenge (for example, 15 mins-72 hours).

A quantitative output of the method for a particular antigen may be characterized as a function of one, two, or more values. In specific embodiments the quantitative output includes 1) the number of donors whose T cell progenies effectively recognized the particular antigen, and 2) the magnitude of the T cell response (for example, the number of SFC per certain number of input T cells).

In specific embodiments, a threshold by which the qualitative determination of whether or not the T cells are responding to the antigen is set. The parameters for defining a threshold of activity are defined as above and include determination of a level of unspecific responses by measuring the magnitude of biological activity against an irrelevant target (antigens not expressed by the pathogen or tumor of interest) or against an unmanipulated PBMCs. This level of unspecific response then establishes a baseline to discriminate between responders and non-responders. Thus, in certain embodiments, a quantitated output of a biological response is measured against a threshold quantity to determine the efficacy and magnitude of the response from each plurality of T cells that is specific for one antigen. In at least some cases, the efficacy encompasses the percentage of individuals in a population that have a biological response that exceeds the threshold quantity. T cells that have greater magnitudes of response than the threshold are considered responders, whereas those with response values less than the threshold value are considered non-responders.

In specific embodiments, a threshold by which the qualitative determination of the magnitude of T cell to the antigen is established. An unspecific response may be determined based upon biological activity against an irrelevant target (antigens not expressed by the pathogen or tumor of interest) or against unmanipulated PBMCs is measure. This establishes a threshold for distinguishing responders from non-responders. A responder is signified when the response rises above the established unspecific response. A non-responder is signified with the response does not rise above the established unspecific response. Thus, in certain embodiments, a quantitated output of a biological response is measured against a threshold quantity to determine the efficacy and magnitude of the response from each plurality of T cells that is specific for one antigen. In at least some cases, the efficacy encompasses the percentage of individuals in a population that have a biological response that exceeds the threshold quantity. T cells that have greater magnitudes of response than the threshold are considered responders, whereas those with response values less than the threshold value are considered non-responders.

Quantitation of a T cell response may be measured by any suitable gauge, such as one or more changes identified intracellularly, secreted, or on the cell surface of cells in the culture. Production of certain compounds, either that are soluble or non-soluble, secreted or not secreted, may be measured. Such compounds may be of any kind, but in specific embodiments they are cytokines. Examples of specific compounds to measure includes IL1α, IL1β, IL-2, IL-3, IL-4, IL-5, IL-6, IL-9, IL-10, IL-12 (p35+p40), IL-13, IL-14, IL-15, IL-16, IL-17a, IL-17B, IL-17F, IL-18, IL-19, IL-20, IL-21, IL-22, IL-23 (p90+p43), IL-25, IL-26, IL-27 (p28+EBI3), IL-28A/B/IL29A, IL-30 (p28 subunit of IL-27), IL-31, IL-32, IL-33, IL-35 (p35+EBI3), TNFα, LTα, LTβ, LIGHT, OX40L, CD40L, FASL, CD27L, CD30L, 4-1BBL, TRAIL, RANK Ligand, GM-CSF, IFNγ, LIF, MIF, TGFβ1, TGFβ2, TGFβ3, and a combination thereof. In cases wherein one evaluates cell surface phenotypical changes, one can measure expression levels of CD11a, CD11c, CD16, CD25, CD27, CD28, CD31, CD38, CD40L, CD43, CD44, CD45, CD49d, CD62L, CD69, CD95, CD122, CD127, CXCR3, CCR5, CCR6, CCR7 and/or KLRG-1, for example. In some cases intracellular and extracellular changes are assessed, and such changes may comprise production/expression of IL-1β, IL2, IL4, IL6, IL12, IFNγ, TNFα, TGFβ, CD107 and/or GM-CSF, for example.

In particular embodiments, the percentages of responders and the percentage of non-responders are utilized in a mathematical relationship with the magnitude of the biological activity that was in response to exposure to a desired agent that is intended to elicit a biological response, which in specific embodiments may represent the measurement of IFN gamma SFC. In particular cases, the mathematical relationship includes the product of the percentage of responders and the magnitude of the response as a ratio to the percentage of non-responders. In specific cases, the mathematical relationship is the product of the percentage of responders plus 1 times the magnitude of the response divided by the percentage of non-responders plus 1.

In particular embodiments, the percentages of responders and the percentage of non-responders are utilized in a mathematical relationship with the magnitude of the biological response (which in specific embodiments may represent the measurement of IFN gamma. In particular cases, the mathematical relationship includes the product of the percentage of responders and the magnitude of the response as a ratio to the percentage of non-responders. In specific cases, the mathematical relationship is the product of (percentage of responders+1) and the magnitude of the response divided by the percentage of non-responders+1.

In particular embodiments a mathematical relationship of a percentage of responders and magnitude of responses for a particular biological measurement is represented in a mathematical formula. Although more than one formula may be applicable, in specific embodiments the formula is as follows:

$$\frac{(\text{percentage of responders} + 1) \times \text{magnitude of biological response}}{(\text{percentage of non-responders} + 1)}$$

Once a value from this mathematical relationship is determined for each antigen, the values for each antigen can be compared and ordered in a hierarchy, for example of most effective antigens to least effective antigens. This spectrum of immunogenicity provides information to a user that is in need of selecting the most suitable antigen(s), for example to be used in immunotherapy. In specific embodiments, following use of this method, one may select 1, 2, 3, or more of the most effective antigens from a collection of possible antigens to be used as the antigen(s) for immunotherapy. In specific embodiments, one selects only the most immunogenic antigen according to the output of the method, whereas in other cases one may select the 2, 3, 4 or more most immunogenic antigens according to the output of the method. In specific cases, one may select the most immunogenic antigen according to output of the method in addition to selecting the second-most immunogenic antigen according to output of the method, third-most immunogenic antigen according to output of the method, and/or fourth-most immunogenic antigen according to output of the method, and so forth. The immunotherapy that employs the most effective antigen(s) as identified in the methods of the disclosure may be of any kind, including a vaccine, immunogenic composition, adoptive T cell transfer, and so forth.

In certain embodiments, an individual that has a medical condition associated with a pathogen or that is seropositive for a pathogen, or that has cancer or is at risk for cancer, may be provided a therapeutically effective amount of immunotherapy that has been designed based on methods of characterizing immunogenic antigens as described herein.

Specific examples of identification of immunogenic antigens for exemplary pathogens and ordering of their immunogenicity/efficacy are provided in the Examples section below.

III. Mathematical and Other Correlations Between Immune Cells and their Clinical Efficacy In particular embodiments of the disclosure, there are methods and compositions that are utilized to determine the efficacy of certain immune cells, such as T cells, NK cells, or NK T cells. The cells may or may not be engineered based on determination of a hierarchy of antigen immunodominance, as described above. In particular embodiments, biological features of a cell product is correlated to efficacy, including clinical efficacy.

In particular embodiments, T cells are produced upon an initial and/or second or subsequent stimulation with an antigen, such as a pathogenic or cancer (including tumor) antigen(s). The specificity and cytotoxicity of the T cells may be measured to provide insight to the clinical efficacy for a certain plurality of antigen-specific T cells. In doing so, one or more biological measurements are assessed for the T cells, such as the amount of secreted compound from the cell and/or amount of cell surface markers on the cell. One or more biological measurements may be intracellular or on the cell surface. The measurements may occur following a certain period of time after exposing the T cells to one or more stimulations, such as within about 15 minutes but no later than 72 hours following one or more stimulations.

In particular embodiments, a value for the biological measurement of such T cells may be compared to a value for an unrelated entity, such as an unrelated or irrelevant target (for example, an antigen that is not present in a particular pathogen or cancer of interest). In at least certain examples the unrelated entity is unmanipulated cells, including unmanipulated PBMCs. In at least certain cases, a percentage of responders for a given antigen is determined using a ratio of a value for a biological measurement for the T cells in question and a value of an unmanipulated cellular counterpart. In specific cases, a percentage of responders for a given antigen is determined by dividing a value of a biological measurement for the cells with a value of a biological measurement of an unmanipulated cellular counterpart. In at least some embodiments, upon such calculation when the result is greater than or equal to 1, the individual whose T cells were tested in the method is considered a responder; when the calculation result is less than one, then the individual whose T cells were tested in the method is considered a non-responder.

In the context of specificity for the T cells, one can test the ability of the cells to produce a certain compound following exposure of the cells to the antigen, for example with at least two separate exposures to the antigen. In particular embodiments, the cells are considered specific when the sum of compound-producing spot-forming cells (SFC) directed against all antigens for a specific pathogen or cancer is ≥ a certain value of $SFCs/2 \times 10^5$ input cells dependent upon the production of which compound for the cells is being measured. For example, for IFNγ production, the baseline to measure a response is $\geq 20$ $SFC/2 \times 10^5$ input cells, although for Granzyme B the baseline to measure a response is $\geq 10$ $SFC/2 \times 10^5$ input cells.

In the context of measuring cytotoxicity for the cells, the cytotoxicity may be determined by standard killing assays including co-culture assays, non-radioactive and radioactive labeling of antigen-loaded/expressing targets. One specific embodiment includes a chromium release assay where T cells are utilized as effectors and the targets are chromium-labeled autologous PHA blasts pulsed with the antigen(s) in question. Effector to target ratios may be (or may be at least or no more than): 5:1, 10:1, 15:1, 20:1, 25:1, 30:1, 35:1, 40:1, 45:1, 50:1, 55:1; 60:1, 65:1, 70:1, 75:1, 80:1, 85:1, 90:1, or 95:1, etc. The cells may be considered to be cytotoxic against a particular pathogen or tumor antigen if the percentage of specific lysis of PHA blasts pulsed with the relevant antigens is higher than the lysis mediated by an irrelevant T cell product or unmanipulated PBMCs. In some conditions a threshold of activity in this assay can be considered as 10% specific lysis at a 40:1 effector to target ratio (for example, after subtracting the percentage of unspecific killing of target cells expressing an unrelated peptide (e.g., not present in the pathogen or tumor of interest).

Clinical efficacy for a particular plurality of antigen-specific T cells may be determined mathematically as a function of antigen specificity and/or cytotoxicity. In specific embodiments, a quantitative value for the efficacy of the cells is obtained through a mathematical relationship that utilizes values for biological measurements for the antigen-specific T cells and unmanipulated control cells, such as unmanipulated PBMCs and utilizes a value for specific killing.

Figure 38:
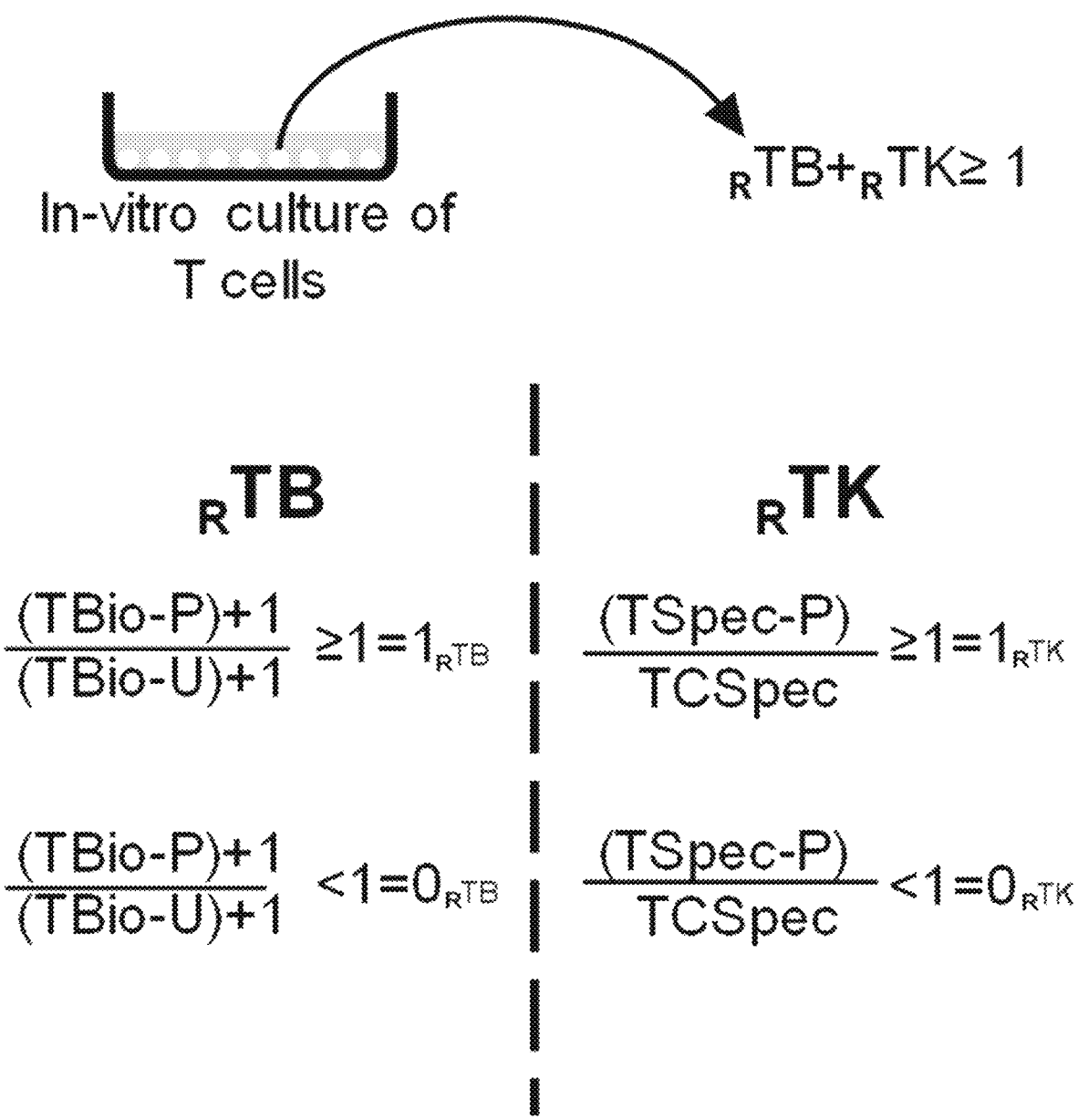
FIG. 38 shows one example of a mathematical relationship for a definition for a product of T cells.

One example of a specific mathematical formula that considers antigen specificity and cytotoxicity includes the following:

$$(_RTB)+(_RTK)\geq 1$$

where $_RTB$ is defined as $[(\text{Thio-P})+1]/[(\text{Tbio-U})+1]$, which when $\geq 1$ will be equivalent to an $_RTB$ value of 1 and when <1 will correspond to an $_RTB$ value of 0; and $_RTK$ is defined as [TSpec-P/TCSpec], which when $\geq 1$ will be equivalent to an $_RTK$ value of 1 and when <1 will correspond to an $_RTK$ value of 0 (see FIG. 38).

Tbio-P is defined as the biological characteristic(s) of the in vitro T cell product and Tbio-U are the biological characteristic(s) of unmanipulated PBMCs or irrelevant antigen. TSpec-P, or the specific killing ability of the in vitro T cell product, is defined as the percentage of lysed HLA-matched target cells expressing the cognate antigen at a predefined effector to target ratio, (e.g., 40:1 effector to target ratio) after subtracting the percentage of unspecific killing by unmanipulated PBMCs of target cells expressing an irrelevant peptide, i.e., an antigen or marker not present within the pathogen or tumor of interest at a predefined effector to target ratio (TCSpec).

In specific embodiments, when for the above-referenced formula the calculation of $(_RTB)+(_RTK)$ is greater than or equal to 1, then the population of T cells being tested will be clinically efficacious. Such cells may be administered in therapeutically effective amounts to an individual in need thereof. When for the above-referenced formula the calculation of $(_RTB)+(_RTK)$ is less than one, the population of T cells being tested will not be clinically efficacious. Such cells may not be administered in therapeutically effective amounts to an individual in need thereof.

Specific examples of mathematical correlations between engineered immune cells and their clinical efficacy are provided in the Examples section below.

Finally, if multiple products are available for clinical use as defined by the formula $(_RTB)+(_RTK)\geq 1$ then products can be ranked either using the raw numerical data $(_RTB$ and/or $_RTK)$ prior to transformation to a binary output. Alternatively the supplemental formula $\alpha(_RTB)+\beta(_RTK)=\phi$ can be applied. In this supplemental formula phi is defined as a clinical efficacy variable (the higher the value, the 'better' the product).

$$\alpha(_RTB)+\beta(_RTK)=$$

Where $_RTB$ is defined as the value resulting from [(Thio-P)+1]/[(Tbio-U)+1]

Where $_RTK$ is defined as the value resulting from [(% TSpec-P)/TCSpec]

where $\alpha$ and $\beta$ are defined as weighting coefficients dependent upon variables including but not limited to therapeutic applications, manufacturing processes, peptide mixtures, cell lines, etc.

where $\phi$ is defined as a clinical efficacy value that may be used to determine a ranking of clinical efficacy among therapeutic products IV. Methods of Generating Antigen-Specific T Cells In specific embodiments, the present disclosure concerns the development of antigen-specific T cells that target at least one antigen from a pathogen (including viral, bacterial, or fungal) or other disease-associated antigen, including tumor antigens. In certain aspects of the disclosure, the present disclosure concerns the development of antigen-specific T cells that target antigens from at least one virus, for example.

In one embodiment, a healthy donor provides a sample, such as a blood sample or leukapheresis product of leukopak. PBMCs are obtained and exposed to the entire pathogen or one or more parts of the pathogen. The cells may also be exposed to one or more cytokines. Following at least 48 hours in culture the cells are fractioned into multiple tubes and re-challenged with individual antigens. The cells may also be exposed to one or more cytokines.

Embodiments of the disclosure concern the generation of antigen-specific T cell lines with specificity against one or more pathogenic or cancer antigens. In certain embodiments, the generation of antigen-specific T cells with such specificity does not utilize dendritic cells in the preparation of such lines, although in alternative embodiments dendritic cells are utilized in standard methods. In some cases, the antigen is presented to PBMCs in the form of one or more peptides that span some or all of the antigen. The antigenic peptides may be provided to the PBMCs in a library of peptide mixtures, which may be referred to as pepmixes. In other aspects of the disclosure, in the preparation of the antigen-specific T cells the disclosure allows for the pooling of a variety of pepmixes.

In some embodiments of the disclosure, following antigen selection methods as encompassed herein, there is a method of generating antigen-specific T cells that target at least one, two, or more antigens from one, two, or more viruses, comprising the steps of: contacting a plurality of peripheral blood mononuclear cells with at least two libraries of peptides, the libraries of peptides each comprising peptides that correspond to a particular viral antigen; and expanding the plurality of cells in the presence of one or more cytokines. In specific embodiments, the method occurs in the absence of exposing the libraries to isolated peptide-pulsed dendritic cells prior to expanding the antigen-specific T cells. In certain embodiments, the one or more cytokines are selected from the group consisting of IL4, IL7, IL12, IL21, IL15, IL6 and a combination thereof. In some embodiments, the peptides are further defined as peptides that overlap in sequence to span part or all of a viral antigen. For example, in certain aspects the peptides overlap by at least three, four, five, or six amino acids, and in some embodiments the peptides are at least six, seven, or eight or more amino acids in length.

In at least some methods of the disclosure, the antigen-specific T cells generated thereby are administered to an individual, for example, an immunocompromised individual. In some cases, the individual has had allogeneic stem cell transplant. In specific embodiments, the cells are administered by injection, such as intravenous, intramuscular, intradermal, subcutaneous, intraperitoneal injection, and so forth, for example. In some embodiments, the individual has lymphoma or leukemia. In some embodiments, the antigen-specific T cells are further defined as polyclonal CD4+ and CD8+ antigen-specific T cells. The PBMCs may be allogeneic to the individual or may be autologous to the individual.

The infection in the individual (or risk or susceptibility thereof) may be from any kind of pathogen, but in specific embodiments the infection is the result of one or more viruses. The pathogenic virus may be of any kind, but in specific embodiments it is from one of the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Arenaviridae, calciviridae, coronaviridae, parvoviridae, reoviridae, poxviridae, or Togaviridae. In some embodiments, the virus produces antigens that are immunodominant or subdominant or produces both kinds. In specific cases, the virus is selected from the group consisting of EBV, CMV, Adenovirus, BK virus, HHV6, RSV, Influenza, Parainfluenza, Bocavirus, Coronavirus, LCMV, Mumps, Measles, Metapneumovirus, Parvovirus B, Rotavirus, West Nile Virus, Spanish influenza, and a combination thereof.

In some aspects the infection is the result of a pathogenic bacteria, and the present disclosure is applicable to any type of pathogenic bacteria. Exemplary pathogenic bacteria include at least *Bacillus anthracis, Bacillus cereus, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica,* or *Yersinia pseudotuberculosis,* for example.

In some aspects the infection is the result of a pathogenic fungus, and the present disclosure is applicable to any type of pathogenic fungus. Exemplary pathogenic fungi include at least *Candida, Aspergillus, Cryptococcus, Histoplasma, Pneumocystis, Stachybotrys, Blastomyces, Coccidioides, Cladosporium, Exserohilum, Penicillium marneffei,* mucormycetes, *Sporothrix,* or *Tinea.*

In some embodiments of the disclosure, the individual may be at risk or have cancer and the present disclosure is applicable to any type of cancer. The cancer may be of any kind or origin, but in specific embodiments it is of the following types: carcinoma, sarcoma, leukemia, lymphoma, multiple myeloma, melanoma, brain and spinal cord tumors, germ cell tumors, blastomas, neuroendocrine tumors, carcinoid tumors and benign tumors. In specific cases, the cancer is selected from the group consisting of Acute Lymphoblastic Leukemia (ALL), acute Myeloid Leukemia (AML), Adrenocortical Carcinoma, Adrenal Cortex Cancer, AIDS-Related Cancers, Kaposi Sarcoma, AIDS-Related Lymphoma, Primary CNS Lymphoma, Anal Cancer, Appendix Cancer, Astrocytomas, Atypical Teratoid/Rhabdoid Tumor, Basal Cell Carcinoma, Bile Duct Cancer, Bladder Cancer, Bone Cancer (including Ewing Sarcoma and Osteosarcoma and Malignant Fibrous Histiocytoma), Breast Cancer, Bronchial Tumors, Burkitt Lymphoma, Gastrointestinal Carcinoid Tumor, Carcinoid Tumors, Cardiac (Heart) Tumors, Embryonal Tumors, Germ Cell Tumors, Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal, Esthesioneuroblastoma, Extracranial Germ Cell Tumor, Extragonadal Germ Cell Tumor, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Extracranial Germ Cell Tumor, Extragonadal Germ Cell Tumor, Ovarian Cancer, Testicular Cancer, Gestational Trophoblastic Disease Gliomas, Hairy Cell Leukemia, Head and Neck Cancers, Heart Tumors, Hepatocellular Cancer, Langerhans Cell Histiocytosis, Hodgkin Lymphoma, Hypopharyngeal Cancer, Intraocular Melanoma, Islet Cell Tumors, Pancreatic Neuroendocrine Tumors, Pancreatic Cancer, Kaposi Sarcoma, Laryngeal Cancer, Laryngeal Papillomatosis, Leukemia, Lip and Oral Cavity Cancer, Liver Cancer, Lung Cancer, Non-Hodgkin Lymphoma, Malignant Fibrous Histiocytoma of Bone, Osteosarcoma, Melanoma, Intraocular Melanoma, Merkel Cell Carcinoma, Skin Cancer, Mesothelioma, Malignant Mesothelioma, Metastatic Squamous Neck Cancer with Occult Primary, Midline Tract Carcinoma Involving NUT Gene, Mouth Cancer-Head and Neck Cancer, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myeloproliferative Neoplasms, Myelogenous Leukemia, Chronic (CML), Nasal Cavity and Paranasal Sinus Cancer, Nasopharyngeal Cancer, Neuroblastoma, Non-Hodgkin Lymphoma, Non-Small Cell Lung Cancer, Oral Cancer, Lip and Oral Cavity Cancer, Oropharyngeal Cancer, Oral Cavity Cancer, Osteosarcoma, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Peritoneal Cancer, Prostate Cancer, Rectal Cancer, Colorectal Cancer, Renal Cell (Kidney) Cancer, Retinoblastoma, Rhabdomyosarcoma, Salivary Gland Cancer, Salivary Gland Tumors, Sarcoma, Osteosarcoma, Rhabdomyosarcoma, Uterine Sarcoma, Uterine Cancer, Vascular Tumors, Sézary Syndrome, Skin Cancer, Small Cell Lung Cancer, Small Intestine Cancer, Soft Tissue Sarcoma, Squamous Cell Carcinoma, Squamous Neck Cancer, Stomach (Gastric) Cancer, Cutaneous T-Cell Lymphoma, Testicular Cancer, Throat Cancer, Thymoma, Thymic Carcinoma, Thyroid Cancer, Thyroid Tumors, Transitional Cell Cancer of the Renal Pelvis and Ureter, Urethral Cancer, Uterine Cancer, Endometrial, Uterine Sarcoma, Vaginal Cancer, Vascular Tumors, Vulvar Cancer, Waldenström Macroglobulinemia (Non-Hodgkin Lymphoma) and Wilms Tumor.

In some embodiments of the disclosure, a library of peptides is provided to PBMCs ultimately to generate antigen-specific T cells. The library in particular cases comprises a mixture of peptides ("pepmixes") that span part or all of the same antigen. Pepmixes utilized in the disclosure may be from commercially available peptide libraries, for example made up of peptides that are 15 amino acids long and overlapping one another by 11 amino acids, in certain aspects. In some cases, they may obtained commercially and/or be generated synthetically. Examples include those from JPT Technologies (Springfield, Va.) or Miltenyi Biotec (Auburn, Calif.). In particular embodiments, the peptides are at least 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more amino acids in length, for example, and in specific embodiments there is overlap of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids in length, for example. The mixture of different peptides may include any ratio of the different peptides, although in some embodiments each particular peptide is present at substantially the same numbers in the mixture as another particular peptide.

In specific embodiments, cells of any kind related to the disclosure may be cultured in suitable media alone or supplemented with cytokines and they may be cultured in a gas permeable culture device (such as G-Rex10 (Wilson Wolf Manufacturing Corporation, New Brighton, Minn.)), other culture apparatus, bioreactor or system or tissue culture plates. Media and/or cytokines may be replenished and cultures may be split following a suitable period of time. In specific embodiments, one or more particular cytokines are employed, including IL7, IL4, IL15, IL12, IL21 and/or IL2, for example.

Embodiments of preparing T cells may comprise the steps of contacting a plurality of peripheral blood mononuclear cells with one, two, or more libraries of peptides, wherein the library or libraries of peptides each comprise peptides that correspond to one or more particular antigens; and expanding the plurality of cells in the presence of one or more cytokines, optionally IL4, IL15, IL21, IL12, IL6 and/or IL7.

V. Kits of the Disclosure

Any of the compositions described herein may be comprised in a kit. In a non-limiting example, cells, cytokines, sample extraction apparatuses, cell culture media, cell culture flasks, peptides, proteins, viruses, and/or other reagents may be comprised in a kit.

The kits may comprise suitably aliquoted compositions utilized in the present disclosure. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the compositions in close confinement for commercial sale. Such containers may include injection or blow-molded plastic containers into which the desired vials are retained. In specific embodiments, the kit comprises one or more means for obtaining blood cells and/or bone marrow cells.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The examples provided herewith are included to demonstrate particular embodiments of the disclosure. It should be appreciated by those of skill in the art that the techniques disclosed in the examples that follow represent techniques discovered by the inventor to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Immunogenic Antigen Identification and Correlation to Clinical Efficacy

In particular embodiment, this disclosure concerns a process for identifying antigens derived from pathogens (viruses, bacteria or fungi) and/or cancer that are immunogenic and have important therapeutic applications. In certain aspects, the process involves compartmentalizing part or all of an entire organism, such as a virus, into fragments known as antigens and establishing a rank of significant therapeutic antigen targets. This information can then be used to select particularly useful fragment(s) or combination of fragments in an organism for the development of treatments, such as vaccines, adoptive cell therapy or any combination thereof. Importantly, this process comprises the identification of immunogenic antigens and therefore is not restricted to a single HLA type unlike previous methods, which may function on the epitope/HLA-restricted level.

One example of this could include the following scenario wherein Virus X is compartmentalized into 6 fragments, or antigens, named A, B, C, D, E, and F (FIG. 1). These fragmented components of Virus X are then used to perform an in vitro stimulation of PBMCs or T cells isolated from healthy individuals (this stimulation can occur either with these fragments pooled together or individually). In this example, T cells obtained from 100 (for example, a minimum of 5 and with no maximum) healthy seropositive individuals for Virus X were cultured in vitro with individual or pooled fragmented targets for a period of 10 days (for example, in a range of 6-14 days) in the presence of Th1-polarizing cytokines. After this initial T cell challenge, the T cells were extracted and challenged again but this time only with individual fragments (antigens). After this second challenge, T cells were assessed for their response. One method to assess T cell response is to evaluate IFNγ production, although other methods to evaluate T cell response are known and can be used. In this example, the IFNγ production was assessed using IFNγ ELIspot. This information can then be processed to determine a threshold of responders vs. non-responders as well as the magnitude of response. A threshold of activity (which may be referred to as a benchmark) for different pathogens (including viruses) and cancer may or may not be the same value for each biological activity measured. For example, different viruses may utilize the threshold for measuring IFNγ production as 20 SFC/2×10$^5$. As another example, different viruses may utilize the threshold for measuring Granzyme B as 10 SFC/2×10$^5$.

Using this technique, the threshold of responders was determined to be a value above 30 SFC per 2×10⁵ input T cells. A threshold of response for biological activity may be (or may be at least or no more than) 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1250, 1500, 1750, 2000, 2250, 2500, 3000, 3500, 4000, 4500, or more SFC/2×10⁵.

An example of these results as illustrated in FIG. 1 follows:

Antigen A was recognized by 80% of donors (n=80) with a mean of 500 SFC/2×10⁵ input T cells.

Antigen B was recognized by 70% of donors (n=70) with a mean of 200 SFC/2×10⁵ input T cells.

Antigen C was recognized by 30% of donors (n=30) with a mean of 100 SFC/2×10⁵ input T cells.

Antigen D was recognized by 90% of donors (n=90) with a mean of 450 SFC/2×10⁵ input T cells.

Antigen E was recognized by 80% of donors (n=80) with a mean of 1000 SFC/2×10⁵ input T cells.

Antigen F was recognized by 30% of donors (n=30) with a mean of 50 SFC/2×10⁵ input T cells.

To next define a hierarchy of immunodominance, the inventors developed a TC (T Cell)-test that takes into consideration both the frequency of responding donors and the number of reactive T cells. The formula is as follows:

$$\frac{(\% \text{ of responders} + 1) \times \text{Magnitude of response} (SFC/2 \times 10^5)}{(\% \text{ of non-responders} + 1)}$$

Figure 2:
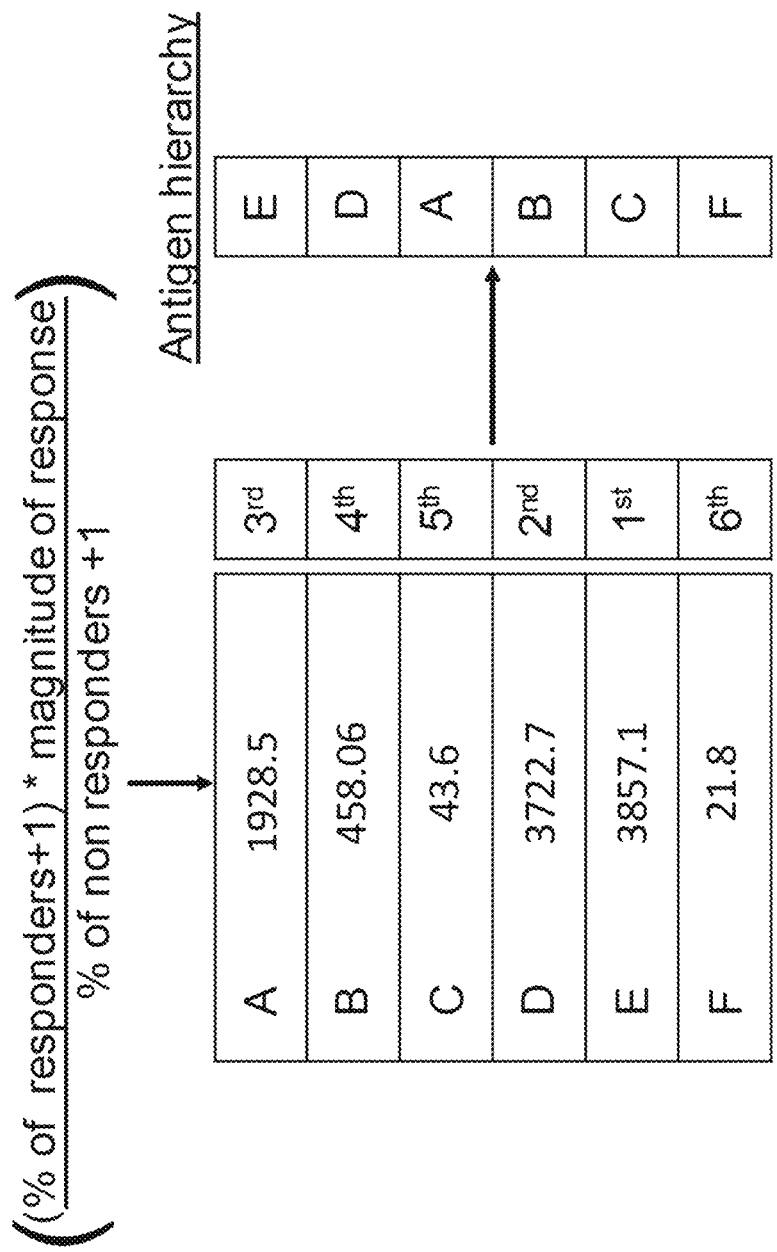
FIG. 2 provides an example of a mathematical formula for ordering the immunogenicity of each antigen in FIG. 1 and identification of an antigen hierarchy.

Thus, a TC-score can be applied to each of the target antigens, as shown in FIG. 2. Using this formula, for example, Antigen A is applied a score of 1928.5, Antigen B is applied a score of 458.1, Antigen C is applied a score of 43.6, Antigen D is applied a score of 3722.7, Antigen E is applied a score of 3857.1 and Antigen F is applied a score of 21.8. Thus, the antigens can be organized into the following hierarchy of immunodominance:

$E>D>A>B>C>F$

Figure 3:
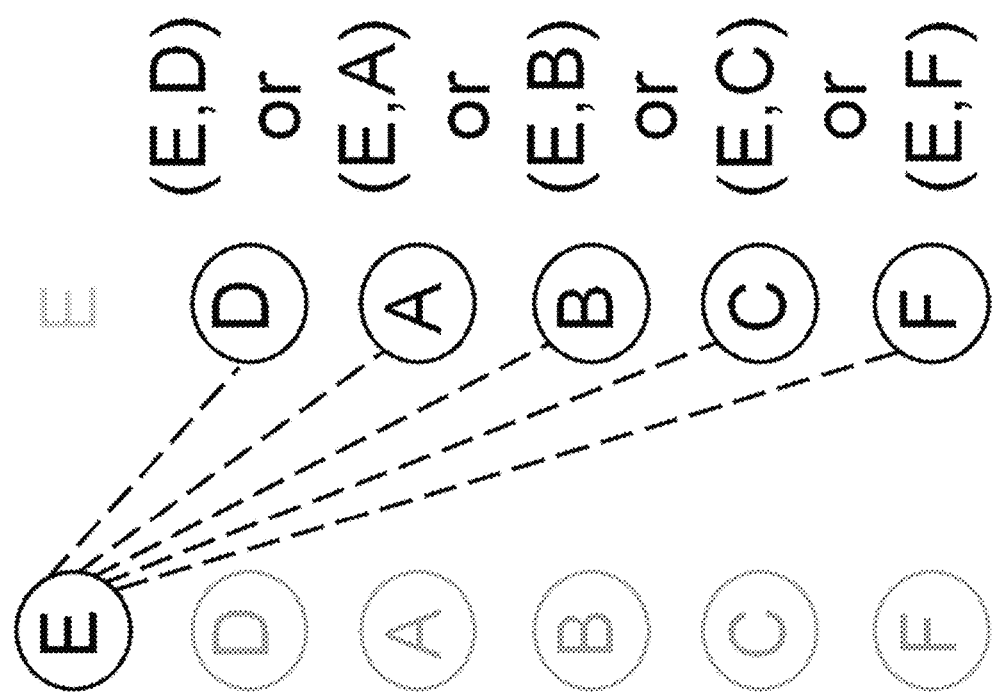
FIG. 3 shows one example of selection of specific antigens based on the antigen hierarchy in FIG. 2.
Figure 4:
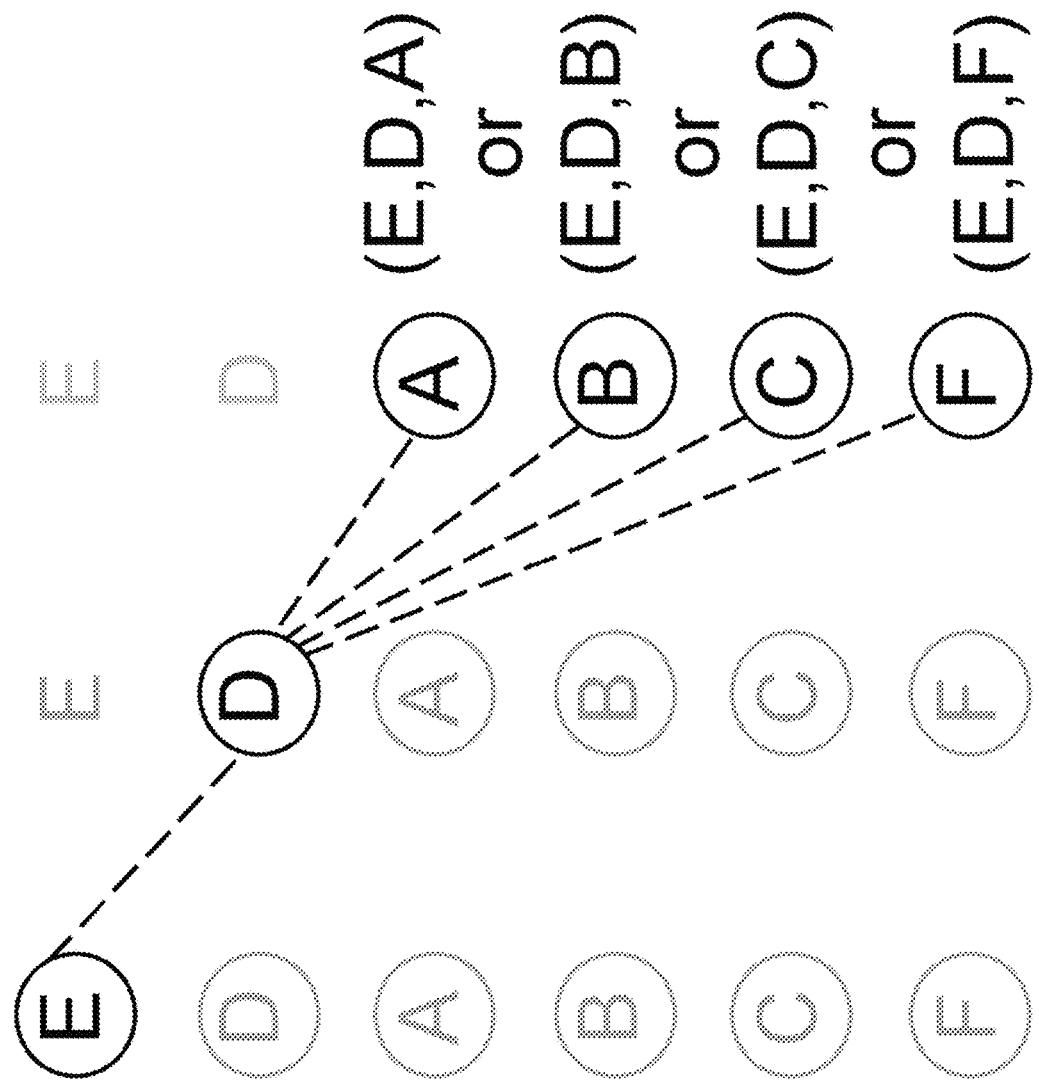
FIG. 4 shows one example of selection of specific antigens based on the antigen hierarchy in FIG. 2.
Figure 5:
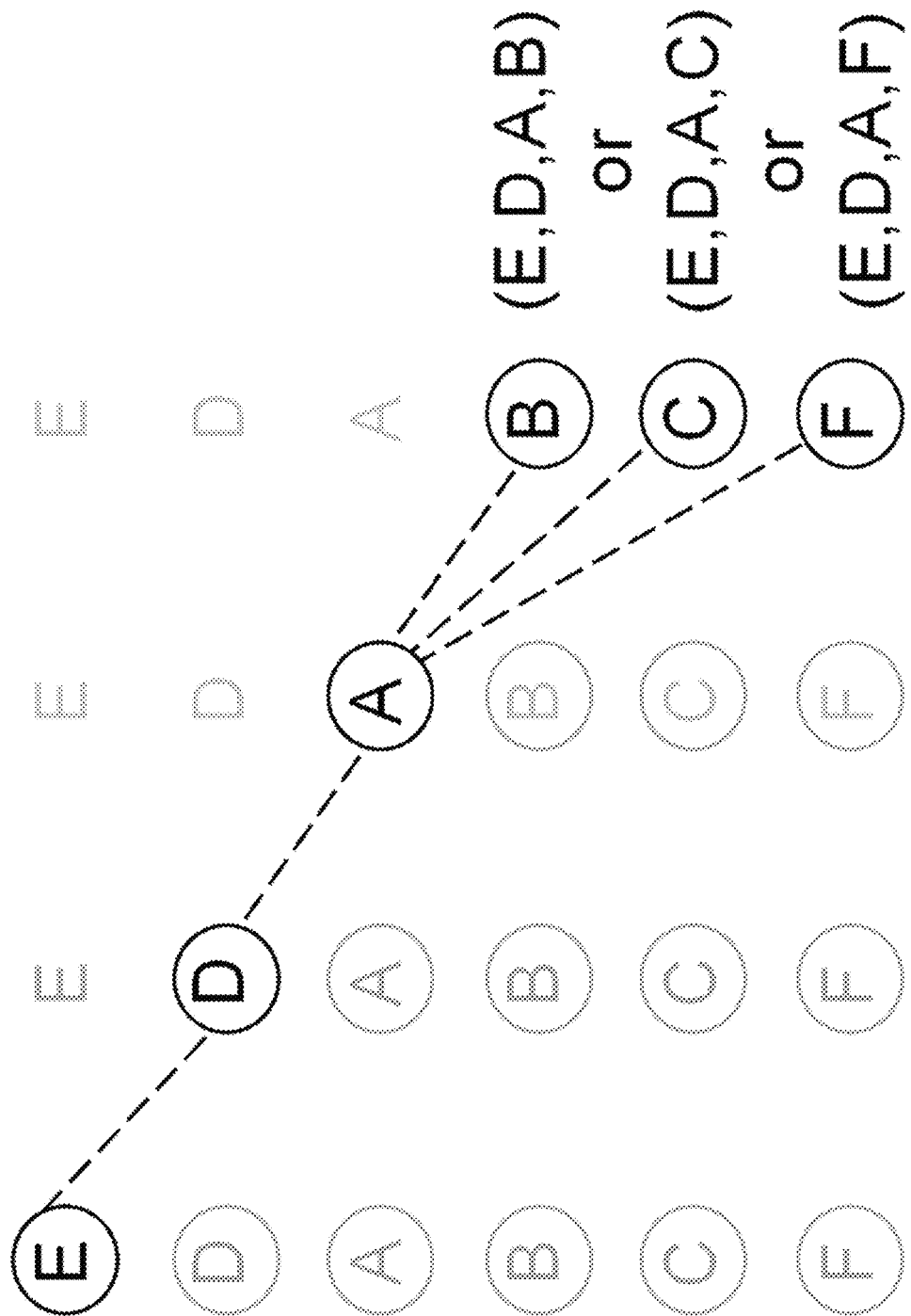
FIG. 5 shows one example of selection of specific antigens based on the antigen hierarchy in FIG. 2.

Hence, in order to provide protective immunity to a patient infected with Virus X, the following represents the identification of desired target or combination of targets (FIGS. 3, 4, and 5):

(a) the most immunodominant target antigen (Antigen E)
(b) a combination of the two most immunodominant targets (E+D)
(c) a combination of the three most immunodominant targets (E+D+A)
(d) a combination of the four most immunodominant targets (E+D+A+B)
(e) a combination of the five most immunodominant targets (E+D+A+B+C)
(f) a combination of the six most immunodominant targets (E+D+A+B+C+F)

It is important to note the method described above can be applied to pathogens other than viruses, including but not limited to bacteria, parasites and fungi as well as tumors.

Figure 6:
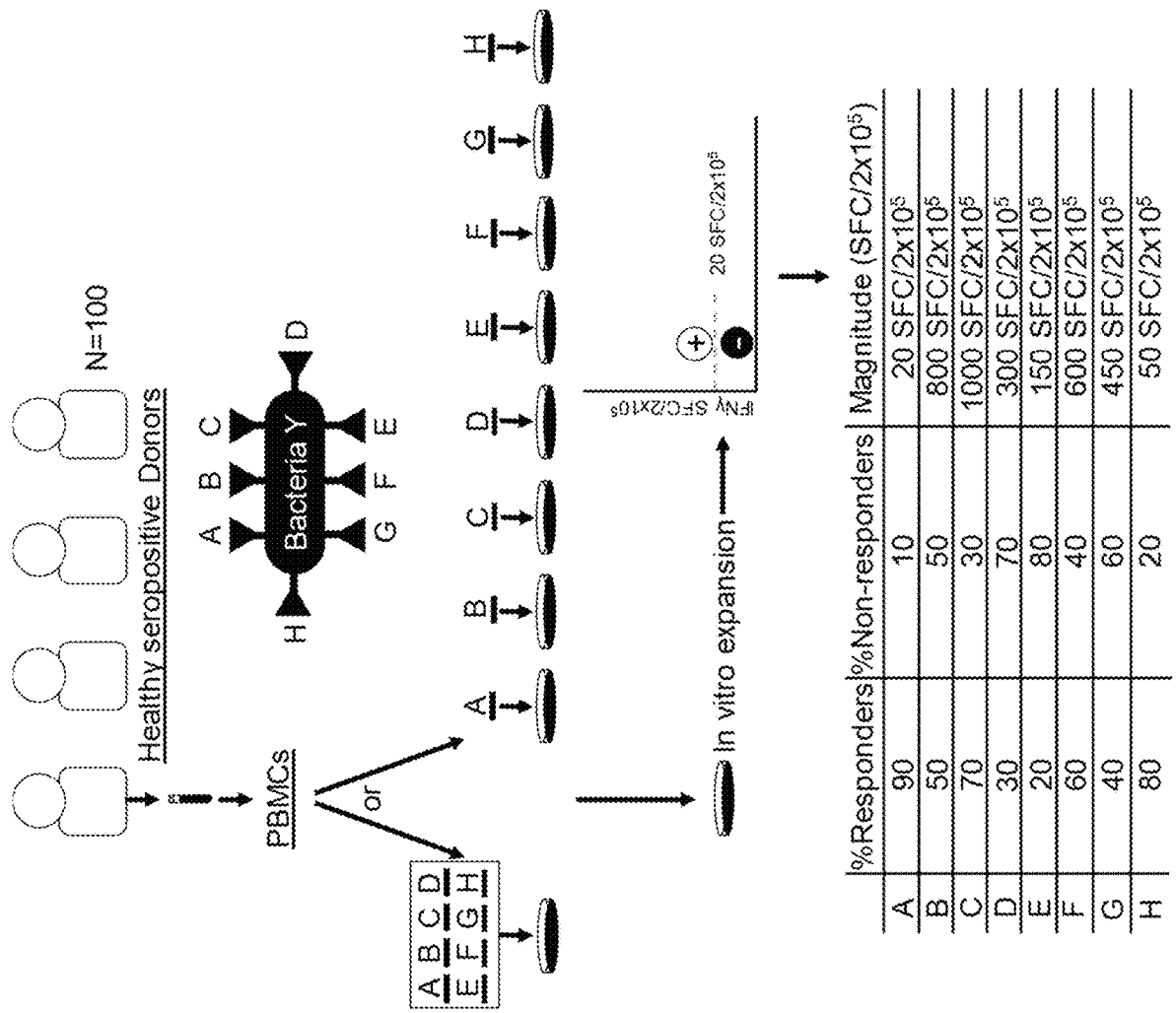
FIG. 6 illustrates an example of immunogenic antigen identification for an exemplary Bacteria Y including exposing PBMCs to multiple antigens followed by re-challenge and determination of a threshold and identification of responders and non-responders.

Therefore, a second example of the process described above could include the following scenario where Bacteria Y is compartmentalized into 8 fragments, or antigens, named A, B, C, D, E, F, G and H. Utilizing the process described above, an example of the results for Bacteria Y as illustrated in FIG. 6 follows:

Antigen A was recognized by 90% of donors (n=90) with a mean of 20 SFC/2×10⁵ input T cells.

Antigen B was recognized by 50% of donors (n=50) with a mean of 800 SFC/2×10⁵ input T cells.

Antigen C was recognized by 70% of donors (n=70) with a mean of 1000 SFC/2×10⁵ input T cells.

Antigen D was recognized by 30% of donors (n=30) with a mean of 300 SFC/2×10⁵ input T cells.

Antigen E was recognized by 20% of donors (n=20) with a mean of 150 SFC/2×10⁵ input T cells.

Antigen F was recognized by 60% of donors (n=60) with a mean of 600 SFC/2×10⁵ input T cells.

Antigen G was recognized by 40% of donors (n=40) with a mean of 450 SFC/2×10⁵ input T cells.

Antigen H was recognized by 80% of donors (n=80) with a mean of 50 SFC/2×10⁵ input T cells.

Figure 7:
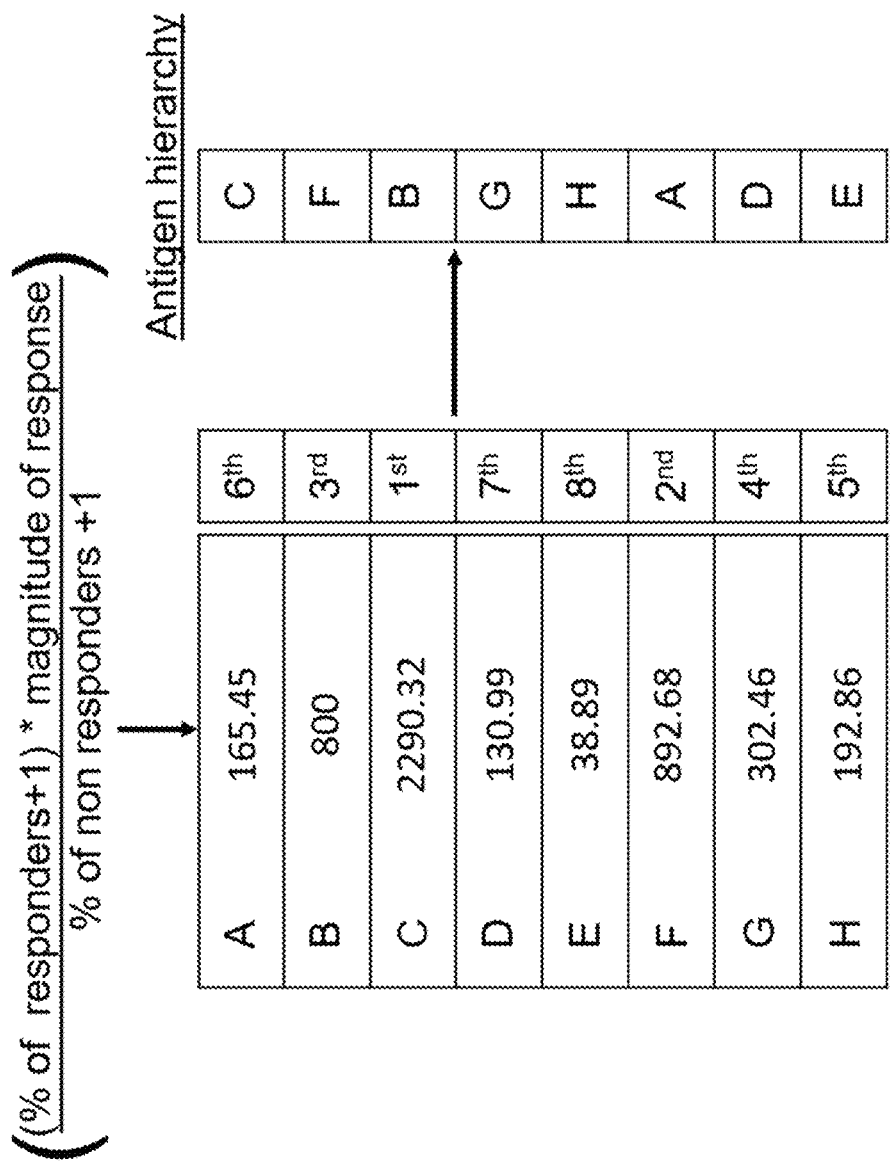
FIG. 7 provides an example of a mathematical formula for ordering the immunogenicity of each antigen in FIG. 6 and identification of an antigen hierarchy.

The hierarchy of immunodominance was determined utilizing the TC-test and applying a TC-scores to each of the Bacteria Y target antigens, as illustrated in FIG. 7. For instance, Antigen A is applied a score of 167.45, Antigen B is applied a score of 800, Antigen C is applied a score of 2290.32, Antigen D is applied a score of 130.99, Antigen E is applied a score of 38.89, Antigen F is applied a score of 892.68, Antigen G is applied a score of 302.46, and Antigen H is applied a score of 192.86. Thus, the antigens can be organized into the following hierarchy;

$C>F>B>G>H>A>D>E$

Figure 8:
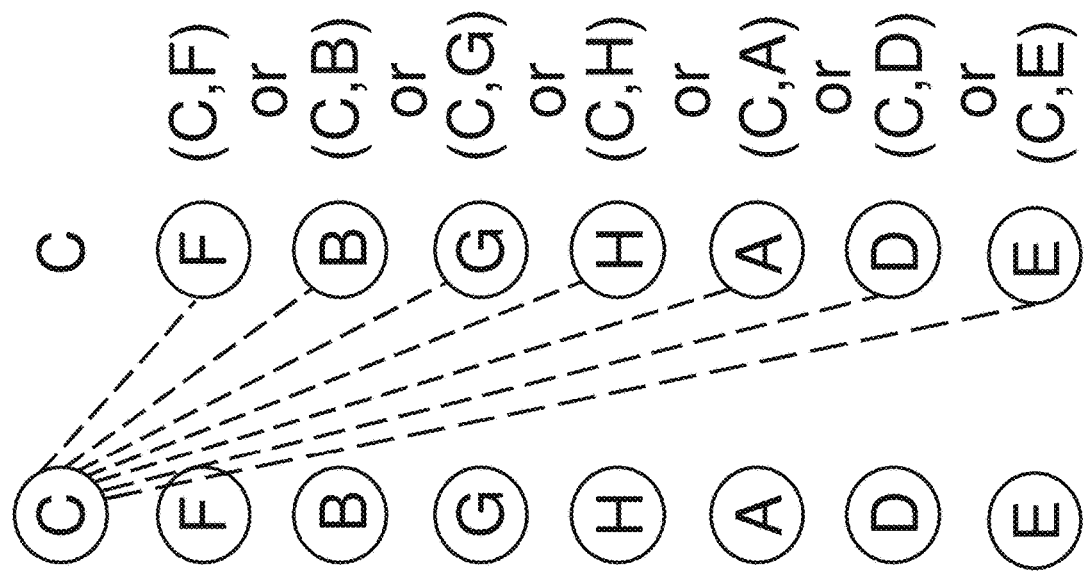
FIG. 8 shows one example of selection of specific antigens based on the antigen hierarchy in FIG. 7.
Figure 9:
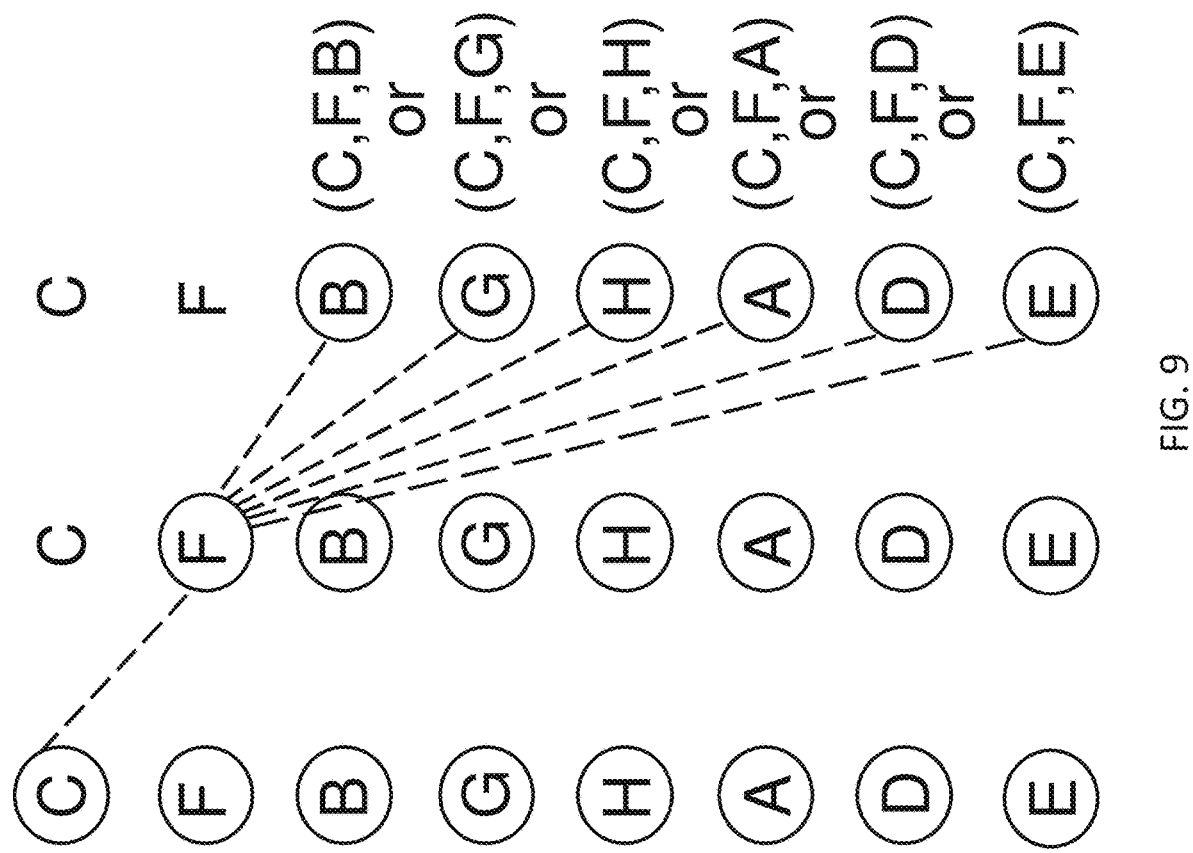
FIG. 9 shows one example of selection of specific antigens based on the antigen hierarchy in FIG. 7.
Figure 10:
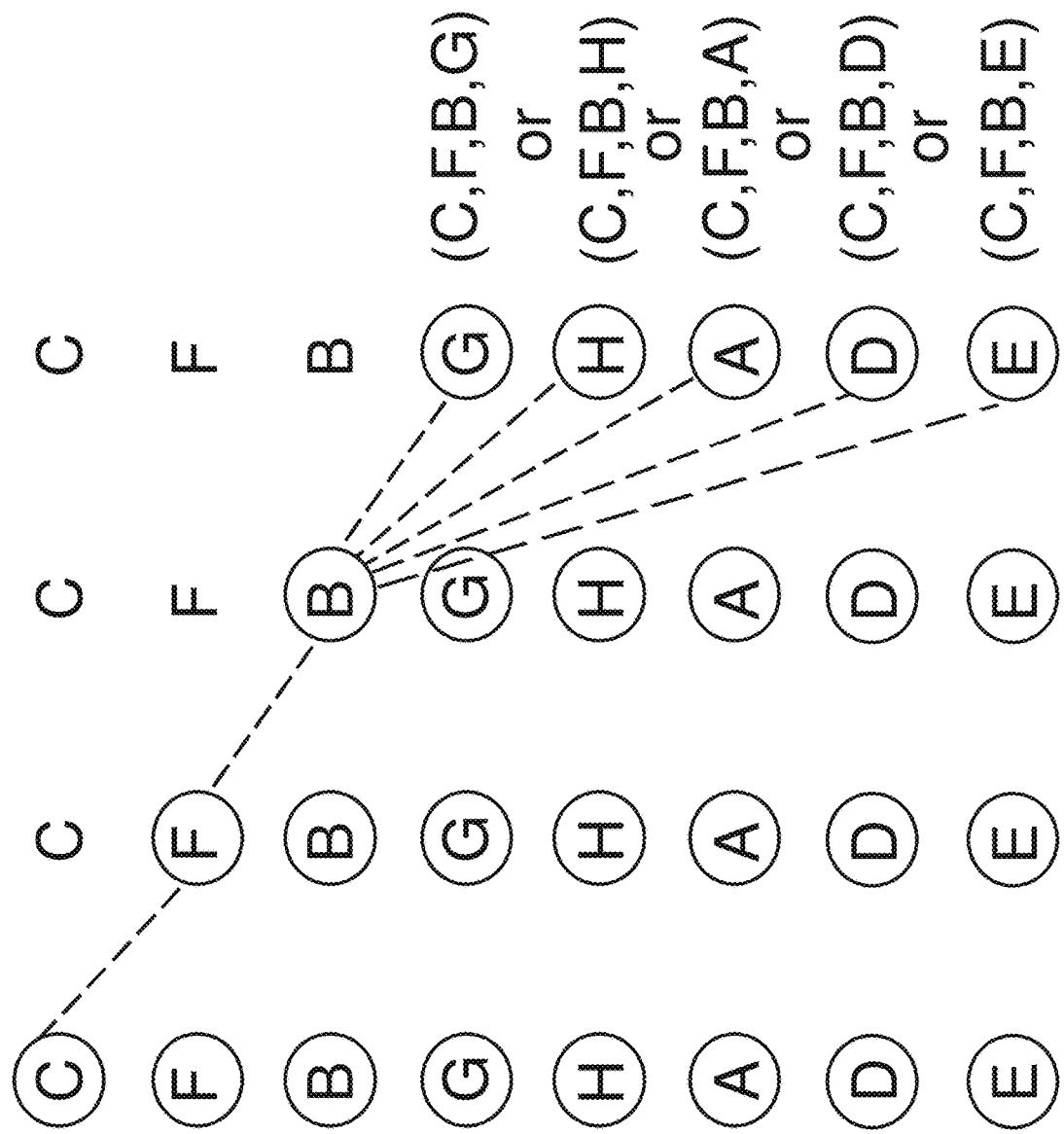
FIG. 10 shows one example of selection of specific antigens based on the antigen hierarchy in FIG. 7.

Thus, in order to provide protective immunity to a patient infected with Bacteria Y, the following represents the identification of desired target or combination of target antigens (FIGS. 8, 9 and 10):

(a) the most immunodominant target antigen (Antigen C)
(b) a combination of the two most immunodominant targets (C+F)
(c) a combination of the three most immunodominant targets (C+F+B)
(d) a combination of the four most immunodominant targets (C+F+B+G)
(e) a combination of the five most immunodominant targets (C+F+B+G+H)
(f) a combination of the six most immunodominant targets (C+F+B+G+H+A)
(g) a combination of the six most immunodominant targets (C+F+B+G+H+A)
(h) a combination of the seven most immunodominant antigens (C+F+B+G+H+A+D)
(i) a combination of the seven most immunodominant antigens (C+F+B+G+H+A+D+E)

Figure 11:
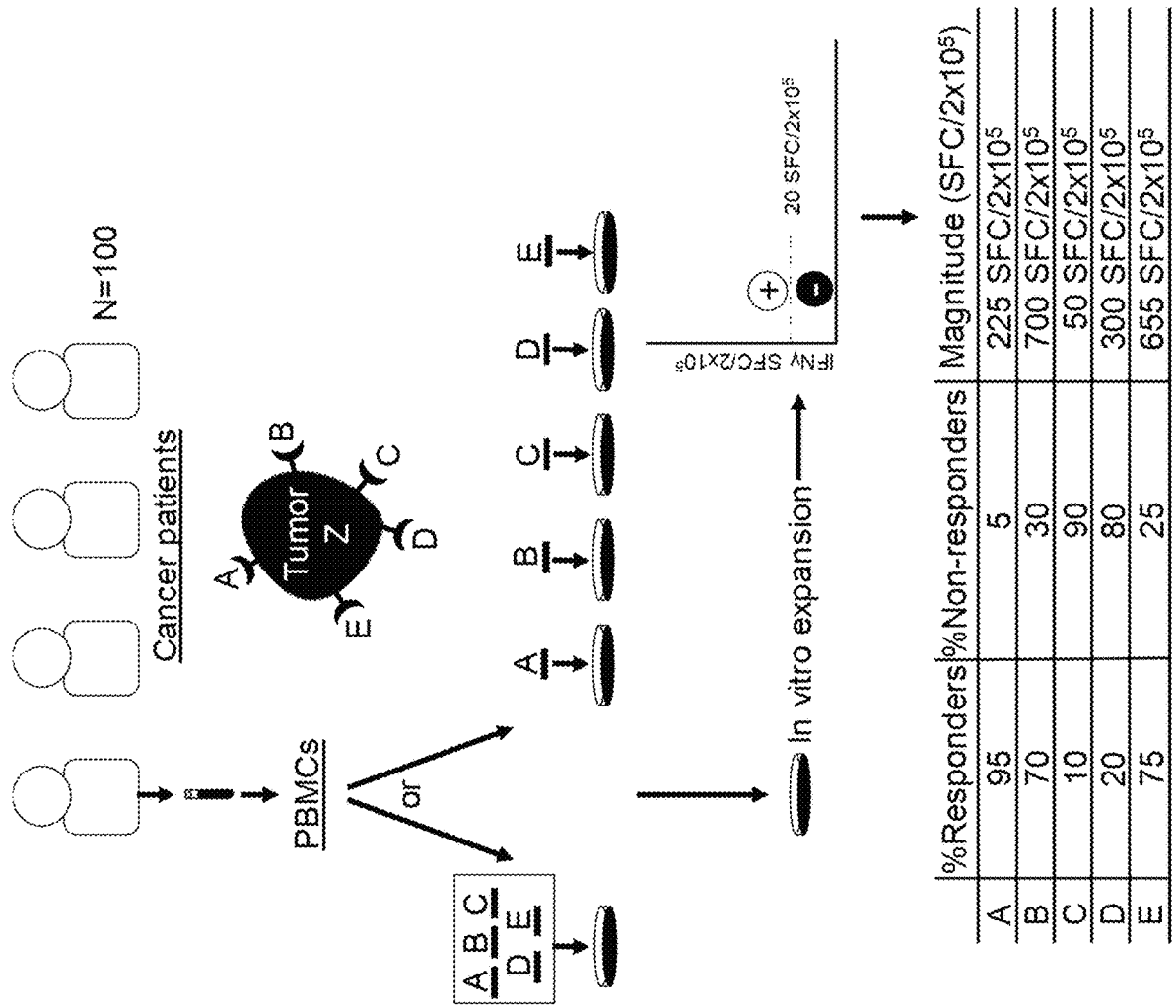
FIG. 11 illustrates an example of immunogenic antigen identification for an exemplary Tumor Z including exposing PBMCs to multiple antigens followed by re-challenge and determination of a threshold and identification of responders and non-responders.

A third example of identifying the hierarchy of immunodominant antigens could include the following scenario where Tumor Z is compartmentalized into 4 fragments, or antigens, named A, B, C, D, E (FIG. 11).

In this example, T cells obtained from 100 individuals with Tumor Z were cultured in vitro with individual or pooled fragmented targets for a period of 10 days in presence of Th1-polarizing cytokines. After this initial T cell challenge, the T cells were extracted and challenged again but this time only with antigens. After this second challenge, IFNγ production was assessed using IFNγ ELIspot.

The threshold of responders was determined to be a value above 20 SFC per $2\times10^5$ input T cells. However, a threshold of response for biological activity may be (or may be at least or no more than) 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1250, 1500, 1750, 2000, 2250, 2500, 3000, 3500, 4000, 4500, or more $SFC/2\times10^5$.

An example of these results follows:

Antigen A was recognized by 95% of donors (n=95) with a mean of 225 $SFC/2\times10^5$ input T cells.

Antigen B was recognized by 70% of donors (n=70) with a mean of 700 $SFC/2\times10^5$ input T cells.

Antigen C was recognized by 10% of donors (n=10) with a mean of 50 $SFC/2\times10^5$ input T cells.

Antigen D was recognized by 20% of donors (n=20) with a mean of 300 $SFC/2\times10^5$ input T cells.

Antigen E was recognized by 75% of donors (n=75) with a mean of 655 $SFC/2\times10^5$ input T cells.

Figure 12:
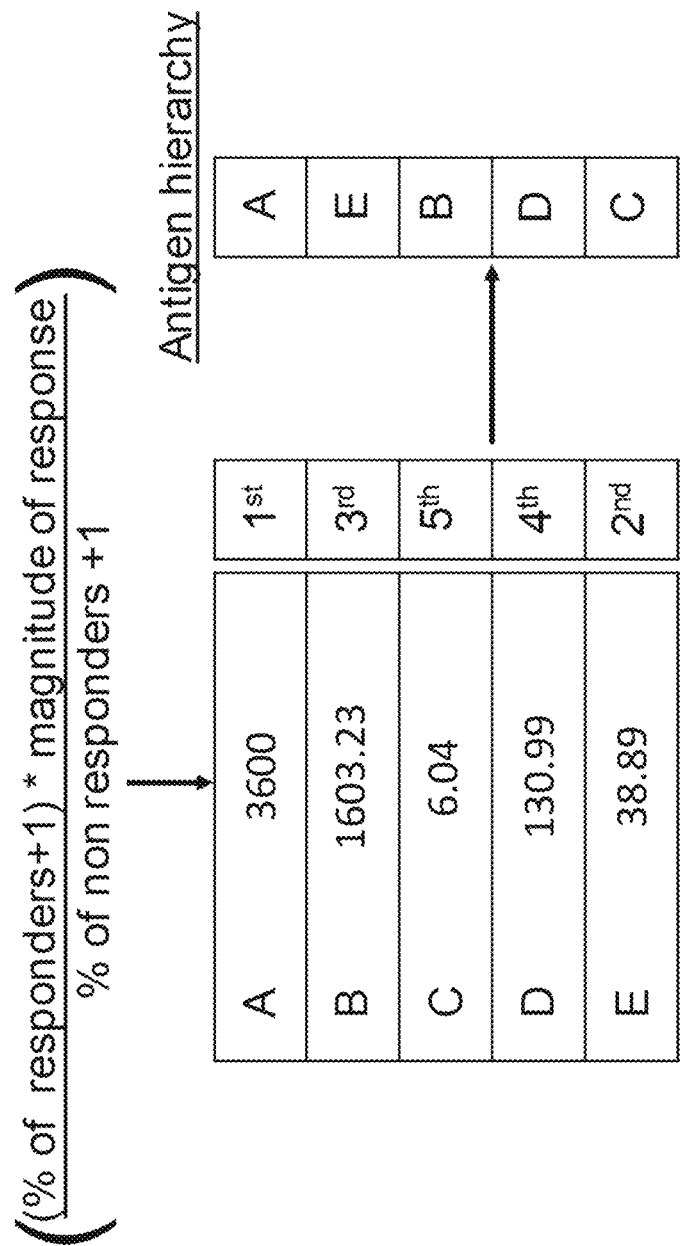
FIG. 12 provides an example of a mathematical formula for ordering the immunogenicity of each antigen in FIG. 11 and identification of an antigen hierarchy.

The hierarchy of response was determined using the TC-test and applying a TC-score to each of the target antigens, as shown in FIG. 11. For instance, Antigen A was assigned a score of 3600; Antigen B was assigned a score of 1603.23; Antigen C was applied a score of 6.04; Antigen D was assigned a score of 130.99; and Antigen E was assigned a score of 38.89. Therefore, the antigens can be organized in the following hierarchy (FIG. 12):

$$A>E>B>D>C$$

Figure 13:
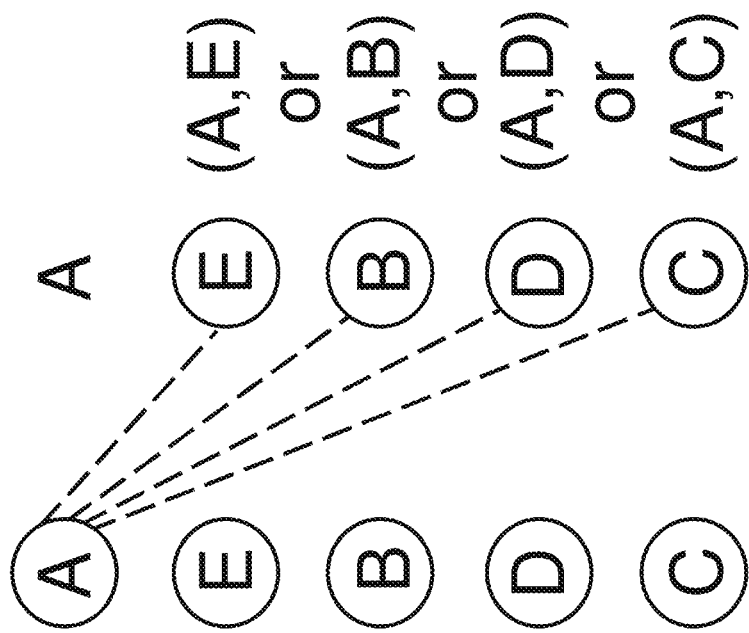
FIG. 13 shows one example of selection of specific antigens based on the antigen hierarchy in FIG. 12.
Figure 14:
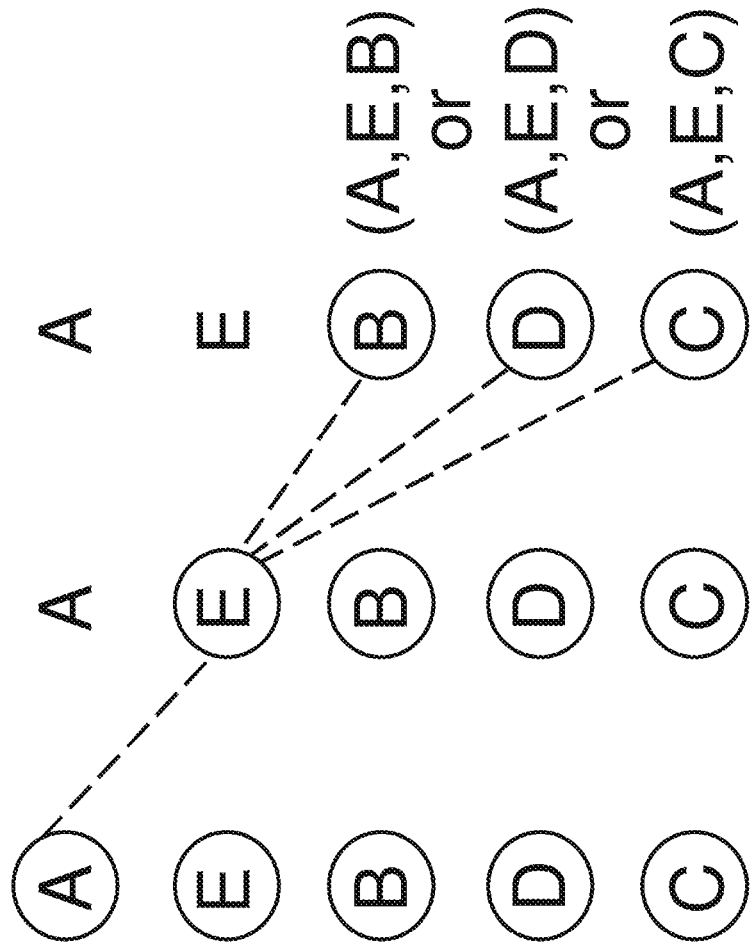
FIG. 14 shows one example of selection of specific antigens based on the antigen hierarchy in FIG. 12.
Figure 15:
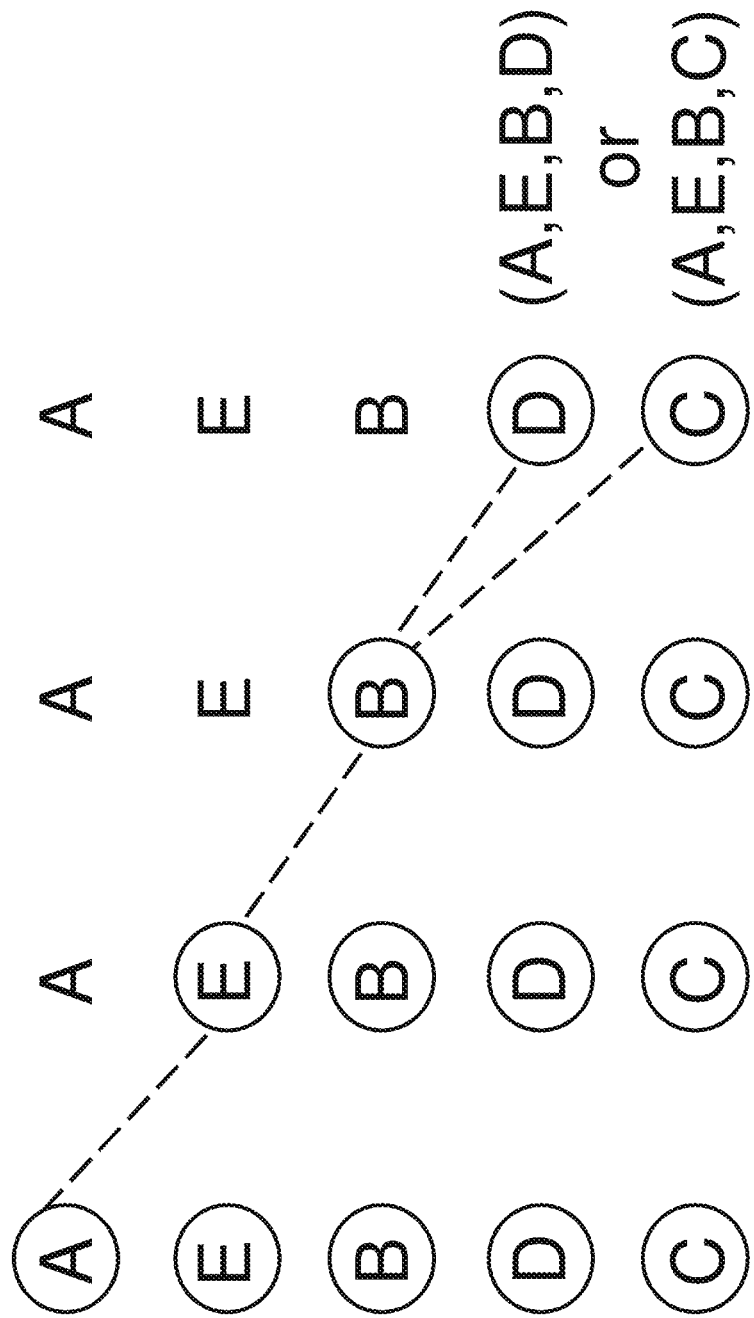
FIG. 15 shows one example of selection of specific antigens based on the antigen hierarchy in FIG. 12.

Thus, in order to provide protective immunity to a patient with Tumor Z, the following represents the identification of desired target or combination of targets (FIGS. 13, 14 and 15):

(a) the most immunodominant target antigen (Antigen A)
(b) a combination of the two most immunodominant targets (A+E)
(c) a combination of the three most immunodominant targets (A+E+B)
(d) a combination of the four most immunodominant targets (A+E+B+D)
(e) a combination of the five most immunodominant targets (A+E+B+D+C)

Example 2

Identifying the Hierarchy of Immunodominance for HMPV

Human Metapneumovirus (HMPV) is an important causative agent of acute respiratory disease in infants, the elderly and immunocompromised individuals (Wen S C & Williams J V Clin. Vaccine Immunol. 2015).

Virology

Figure 16:
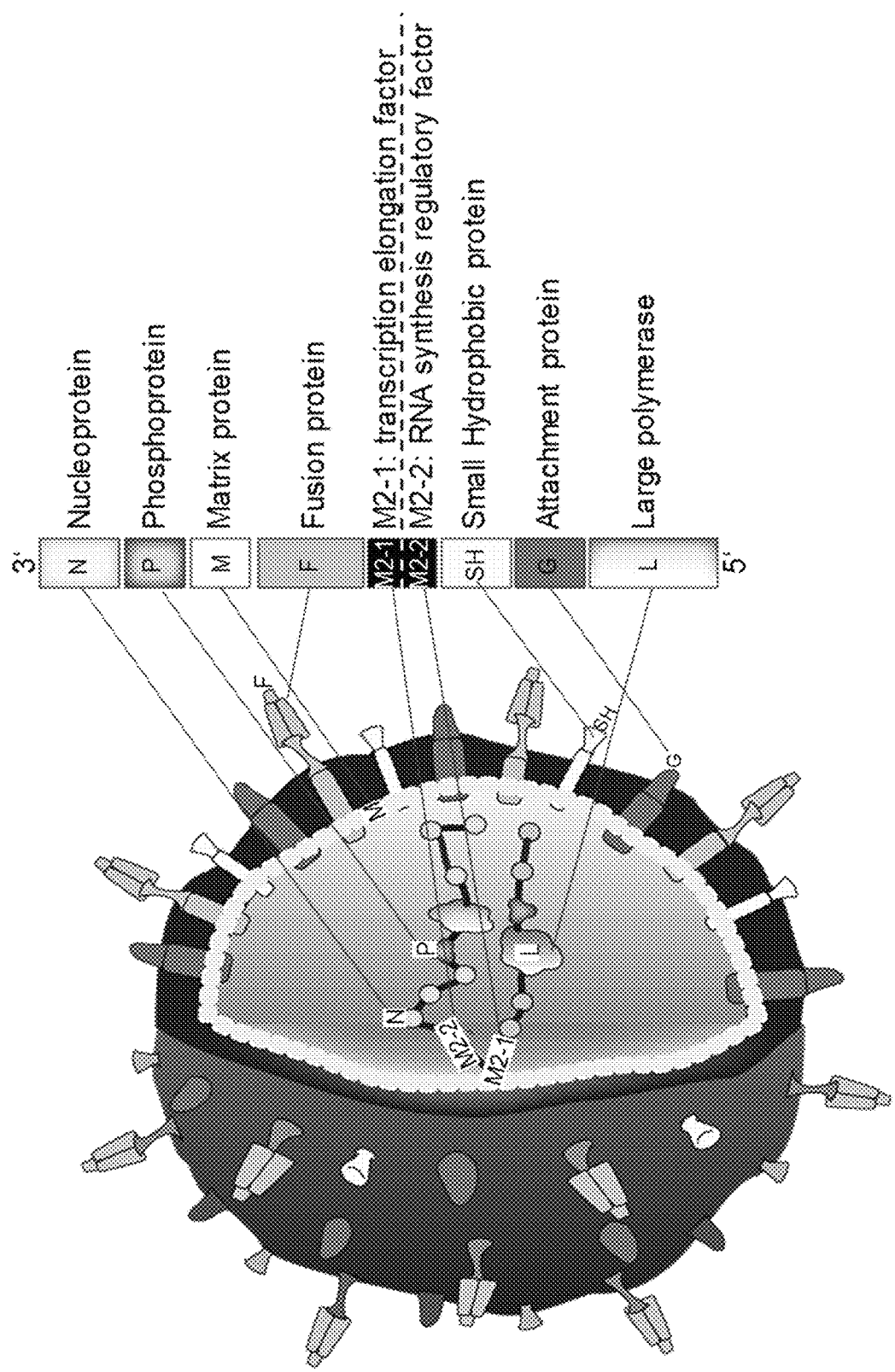
FIG. 16 illustrates a HMPV molecule and its gene products, including 3'-N-P-M-F-M2-SH-G-L-5'.
Figure 19:
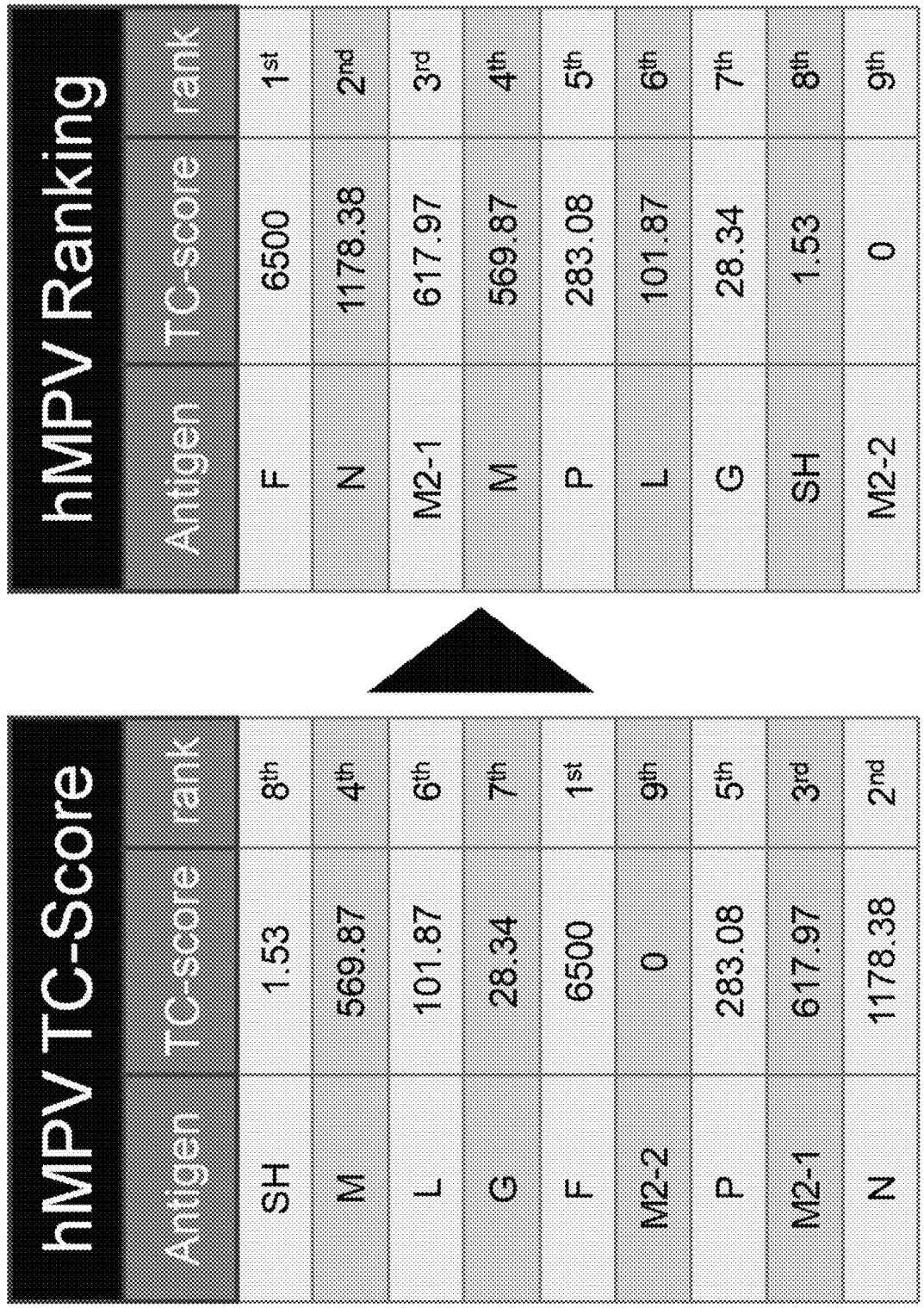
FIG. 19 provides an exemplary of a T cell score that corresponds to hMPV ranking.
Figure 20:
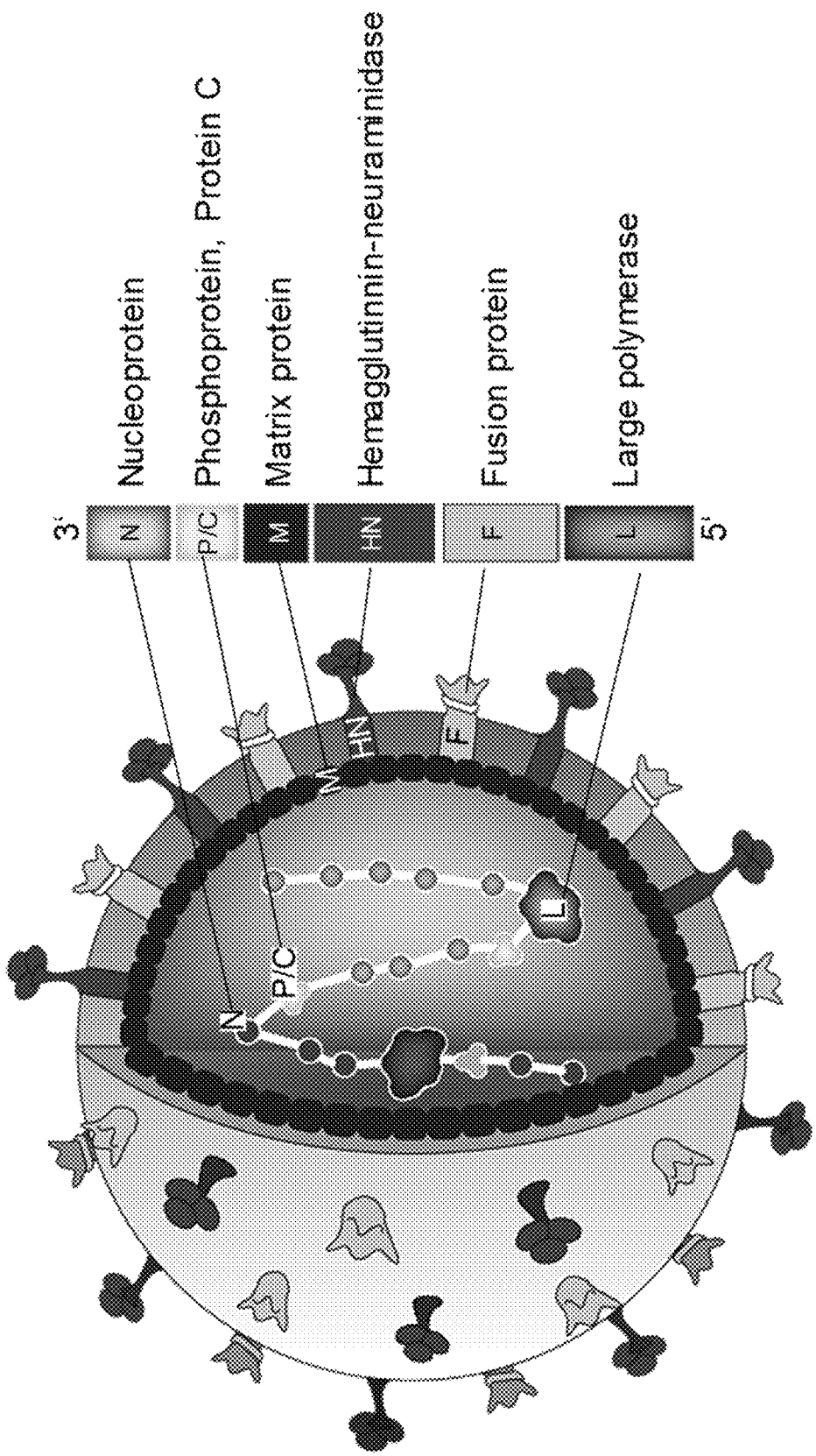
FIG. 20 illustrates a PIV3 molecule and its gene products, including N-P-M-F-HN-L.
Figure 23:
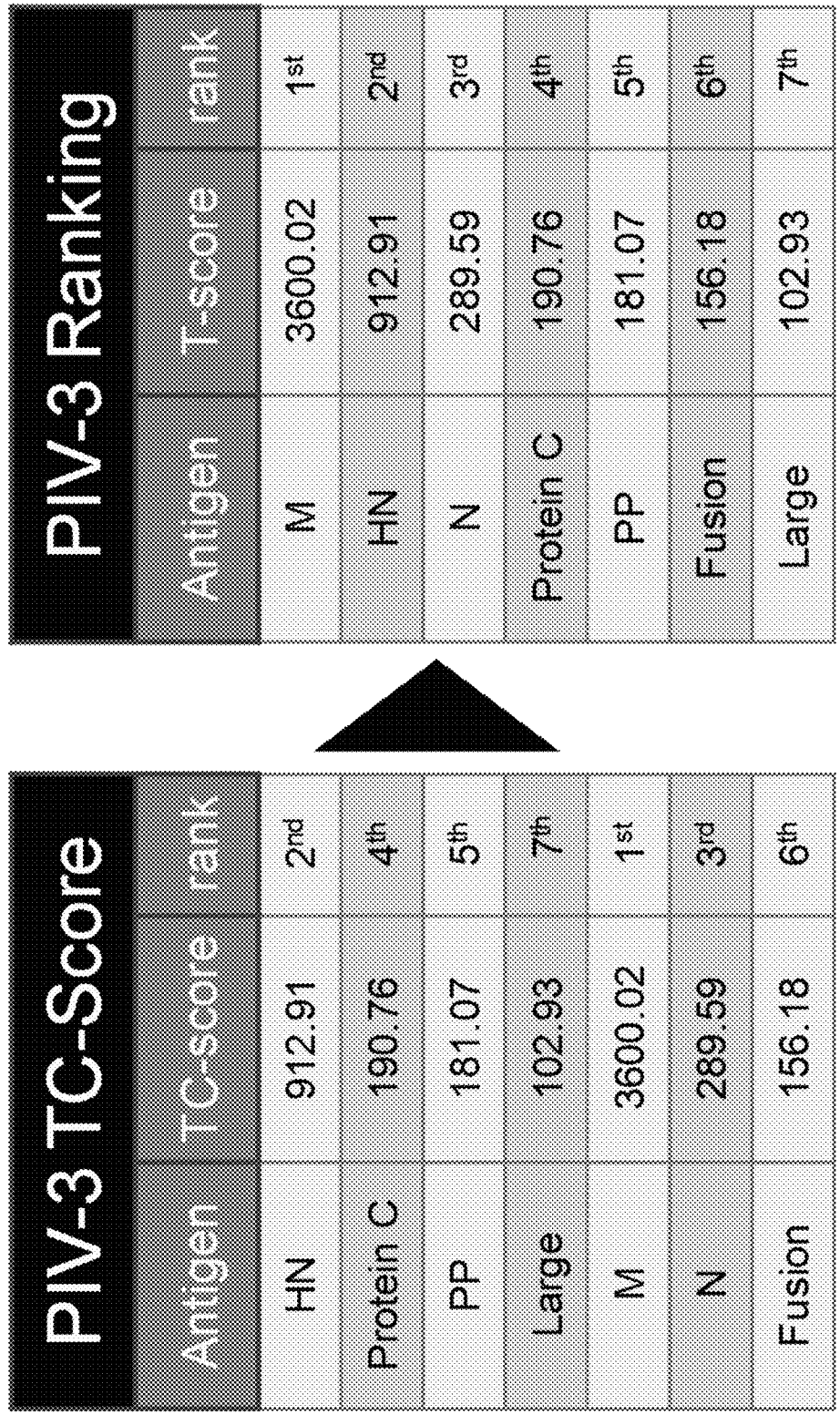
FIG. 23 provides an exemplary of a T cell score that corresponds to PIV3 ranking.
Figure 25:
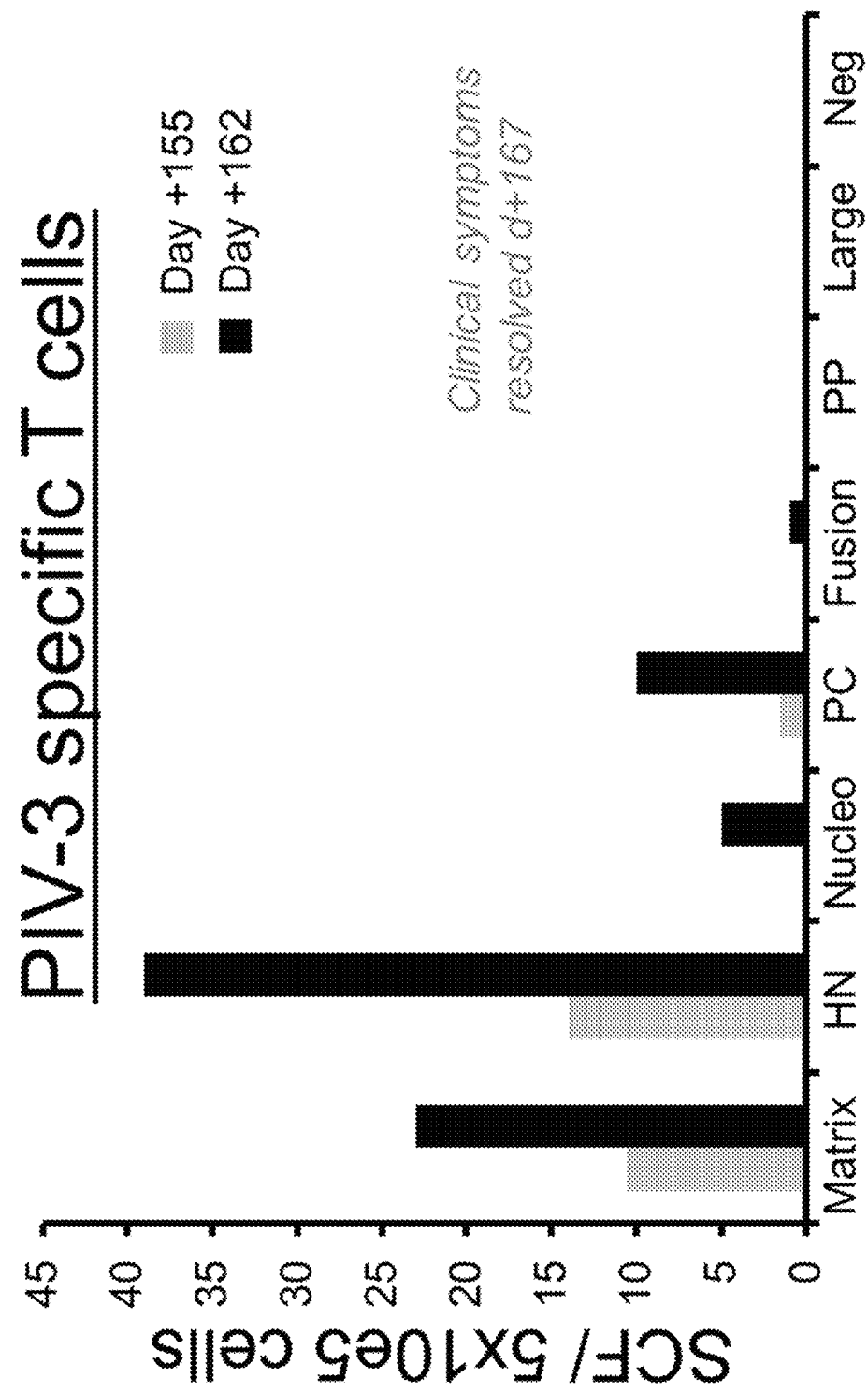
FIG. 25 demonstrates the frequency of PIV3-specific T cells targeting antigens M and N exhibiting a particular enrichment between Day 155 and Day 162.
Figure 26:
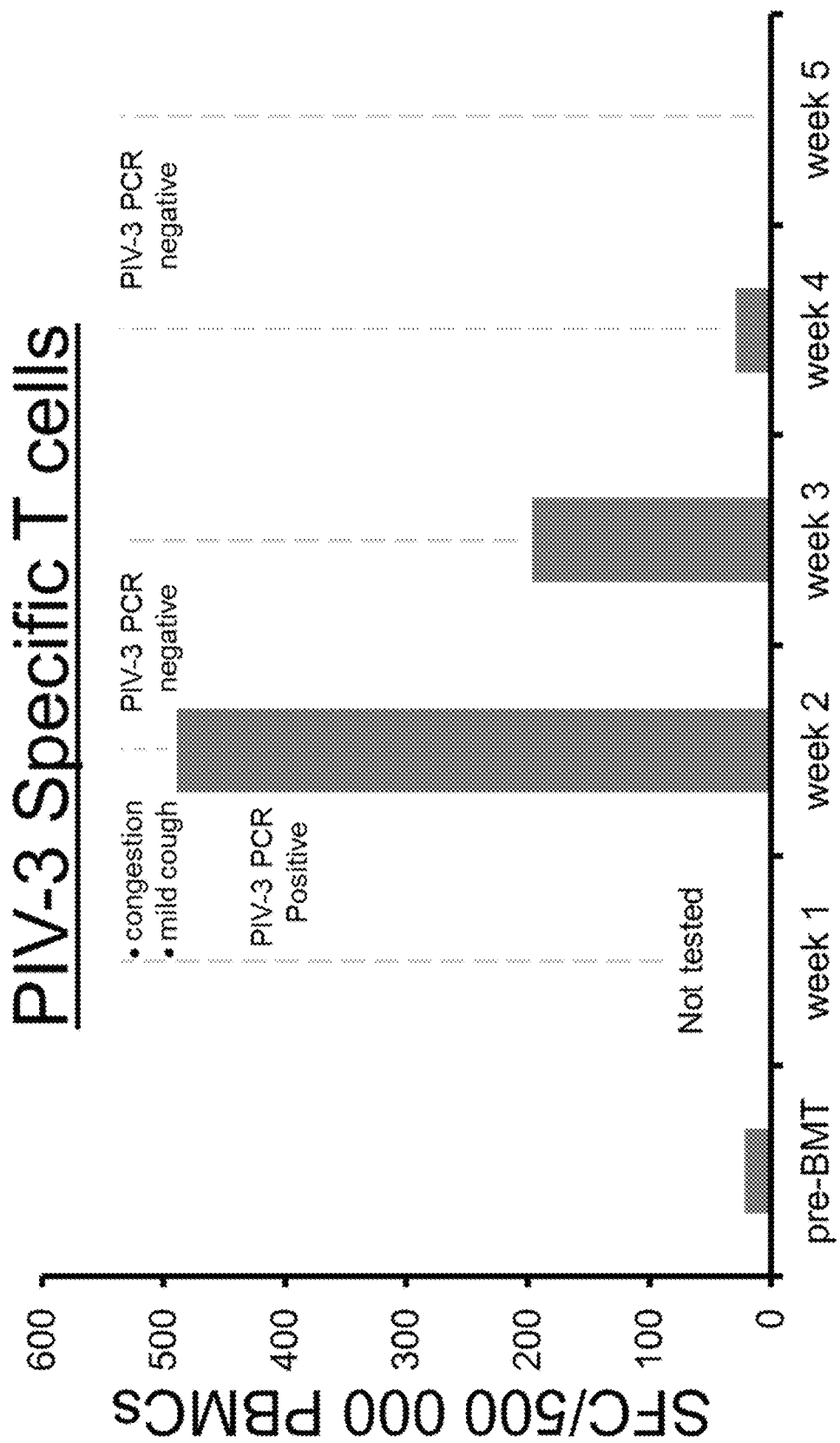
FIG. 26 shows an example of clinical relevance of PIV3 T cells to control viral infection, where an increase in the frequency of PIV3-specific T cells had an inverse correlation with the symptoms of infection and viral detection in a representative patient with active infection post bone marrow transplant (BMT).

HMPV is an enveloped, negative-sense, single-stranded RNA virus of the Metapneumovirus genus, Pneumovirinae subfamily, within the Paramyxoviridae family. The HMPV genome contains 8 genes, in the order 3'-N-P-M-F-M2-SH-G-L-5', encoding 9 proteins (FIG. 16).

There are three transmembrane glycoproteins on the virion surface: small hydrophobic (SH) protein, a heavily glycosylated putative attachment protein (G), and the fusion (F) glycoprotein, which mediates viral fusion and entry. While the function of the SH protein is unclear, several studies suggest a role for this protein in inhibiting the innate and adaptive immune responses. The matrix protein (M) lines the virion beneath the viral membrane and, analogously to the RSV M protein, plays a role in viral assembly and budding. The RNA genome is entirely encapsidated by the nucleoprotein (N) to form the nucleocapsid (sometimes called the ribonucleoprotein complex). The N protein, phosphoprotein (P), M2-1 protein, and large RNA-dependent RNA polymerase protein (L), associate with the RNA genome to form the viral RNA polymerase complex. The second M (M2) gene encodes two proteins: M2-1, which promotes transcription processivity in RSV and is essential for the synthesis of full-length mRNAs, and M2-2, which balances transcription and genome replication (Wen S C and Williams J V *Clin. Vaccine Immunol.* 2015).

Transmission

HMPV is thought to be transmitted by direct or close contact with contaminated secretions, which may involve saliva, droplets or large particle aerosol. HMPV RNA is found in excretions five days to two weeks after initiation of symptoms. However, the extent of contagiousness is unknown since detection of HMPV RNA in respiratory samples from patients recovering from infection does not per se indicate viable contagious viral particles (Haas L E et al. Viruses 2013).

Epidemiology and Clinical Features

HMPV is commonly found in the pediatric population, with high susceptibility rates in children less than 2 years old (Panda S et al. Int. J. Infect. Dis. 2014). In a retrospective study done on nasal-wash specimens obtained over a 25-year period from otherwise-healthy children presenting with acute respiratory illness, 20% of nasal-wash specimens contained HMPV RNA or viable virus (recovered in culture). The mean age of HMPV-infected children was 11.6 months, and the majority of the illnesses occurred in late winter/early spring (Wen S C & Williams J V Clin. Vaccine Immunol. 2015).

The proportion of HMPV infections in adults varies between 3%-7.1%. This is higher (ranging from 4.3%-13.2%) in hospitalized adults (Haas L E et al. Viruses 2013). HMPV infection in adults normally shows only mild flu-like symptoms. However, in some adult cases (especially elderly adults), severe complications such as chronic obstructive pulmonary disease (COPD) can occur. Dyspnea is more likely in adults as compared to children. HMPV infection has also been reported in several immunocompromised patients, such as lung transplant recipients, patients with hematological malignancies, and hematopoietic stem cell transplant recipients (Panda S et al. Int. J. Infect. Dis. 2014). Clinical course in these patients is prolonged and respiratory failure may develop (Haas L E et al. Viruses 2013).

Prevention and Treatment

Although there are currently no HMPV vaccines licensed for use in humans, a variety of strategies including the use of inactivated virus, subunit protein, virus-like particles, live attenuated virus and chimeric virus have been investigated in animal models.

Several monoclonal antibodies have been developed to target the HMPV fusion protein. Two murine MAbs, MAb 234 and MAb 338, exhibited high-affinity binding to F protein and were effective when administered prophylactically or therapeutically in animal models. Similarly, human monoclonal antibodies, MPE8 and 54G10 exhibited prophylactic and therapeutic efficacy against HMPV in mouse models.

Treatment for HMPV infection in humans is mainly supportive. Ribavirin, a nucleoside analog was shown to have efficacy against HMPV both in vitro and in BALB/c mice. However, ribavirin is expensive, can cause adverse effects, such as hemolytic anemia, and is a potential teratogen. Furthermore, no controlled trials have been performed to study its efficacy in treating HMPV infection, though there are numerous anecdotal reports. Ribavirin has been administered to patients with severe HMPV infections, in some cases with intravenous immunoglobulin (IVIg). IVIg has antiviral activity against HMPV in vitro, although it requires infusions of large fluid volumes and is associated with adverse events in children with congenital heart disease (Wen S C & Williams J V Clin. Vaccine Immunol. 2015).

Immune Response and Correlates of Protection

Adaptive immune response (humoral and cellular immunity) is the most important aspect of protective immunity against HMPV. Indeed, animal studies show that passive transfer of antibody is sufficient to protect from HMPV replication. T cells are also important for viral clearance. Depletion of both CD4+ and CD8+ T cells resulted in higher viral titers after HMPV challenge in BALB/c mice (Wen S C & Williams J V Clin. Vaccine Immunol. 2015). In addition, human patients with previous HMPV respiratory disease were shown to have CD8+ T cell responses to HMPV proteins (Wen S C & Williams J V Clin. Vaccine Immunol. 2015). Therefore assessing the immunodominant hierarchy of HMPV is necessary to develop new therapeutic strategies.

Establishing a Hierarchy of Immunodominance for hMPV

Applying the process and TC-test described in Example 1, the following represents a novel characterization of T cell response for hMPV:

hMPV was compartmentalized into the following fragments: SH, M, L, G, F, M2-2, P, M2-1 and N. The percentage of responders were 3.4% for SH, 79.3% for M, 44.8% for L, 31% for G, 96.5% for F, 0% for M2-2, 68.9% for P, 79.3% for M2-1 and 86.2% for N and a magnitude of response of 34 for SH, 154 for M, 125 for L, 62 for G, 300 for F, 0 for M2-2, 130 for P, 167 for M2-1 and 220 for N. Applying the TC-test, we identified a TC-score of 1.53 for SH, 569.87 for M, 101.87 for L, 28.34 for G, 6500 for F, 0 for M2-2, 283.08 for P, 617.97 for M2-1, and 1178.38 for M (FIGS. 17-18). Applying the TC-score, the inventors ranked the different hMPV antigens (FIG. 19) as follows:

*F>N>M2-1>M>P>L>G>SH>M2-2*

Hence, in order to provide protective immunity to a patient infected with HMPV, the following represents the identification of desired target or combination of targets (FIG. 19):

(a) the most immunodominant target antigen (Antigen F)
(b) a combination of the two most immunodominant targets (F+N)
(c) a combination of the three most immunodominant targets (F+N+M2-1)
(d) a combination of the four most immunodominant targets (F+N+M2-1+M)
(e) a combination of the five most immunodominant targets (F+N+M2-1+M+P)
(f) a combination of the six most immunodominant targets (F+N+M2-1+M+P+L)
(g) a combination of the seven most immunodominant targets (F+N+M2-1+M+P+L+G)
(h) a combination of the eight most immunodominant targets (F+N+M2-1+M+P+L+G+SH)
(i) a combination of the nine most immunodominant targets (F+N+M2-1+M+P+L+G+SH+M2-2)

Example 3

Identifying the Hierarchy of Immunodominance for PIV3

Human parainfluenza virus type 3 (PIV3) is a respiratory tract pathogen and is a major cause of bronchiolotis and pneumonia in infants and very young children (Zvirbliene A. et al. Viral Immunology 2009). In addition to young children, PIV3 poses a threat to the elderly and to immunocompromised adults. PIV3 infection also causes severe illness leading to death (35%-75%) in patients receiving hematopoietic stem cell transplant (HSCT) (Nichols W G et al. Blood 2001; Maziarz R T et al. Biol Blood Marrow Transplant 2010; Sasaki M et al. Emerging Infect. Dis. 2013)

Virology

PIV3 is a representative of the genus Respirovirus of the family Paramyxoviridae. It is an enveloped RNA virus containing a single-stranded RNA genome of negative polarity. The PIV3 genome contains approximately 15,500 nucleotides organized to encode at least six structural proteins in the invariant order N-P-M-F-HN-L (FIG. 20).

Infection of the host cell by PIV3 is initiated by binding of the hemagglutinin-neuraminidase (HN) glycoprotein on the virion envelope to sialic acid on cellular membrane proteins. The fusion (F) protein then mediates the fusion between the viral envelope and the host-cell plasma membrane. This releases the viral nucleocapsid, which consists of the viral genome tightly bound by the nucleoprotein (N) and associated with the phosphoprotein (P) and the large RNA-dependent RNA polymerase (L) protein. The nucleocapsid-bound polymerase directs copying of the viral genes into separate mRNA transcripts and also directs replication of the RNA genome. Progeny nucleocapsids assemble and are packaged into virions that bud from plasma membrane. The matrix (M) protein coats the inner surface of the envelope and the spike-like glycoproteins F and HN project from the outer surface of the envelope (Schmidt A C et al. Expert Rev Respir. Med. 2012)

Transmission

Viral transmission occurs by direct inoculation of contagious secretions from hands or of large particle aerosols into the eyes, nose, or, rarely, the mouth (Maziarz R T et al. Biol Blood Marrow Transplant 2010). Replication of PIV3 occurs in the superficial epithelial cells lining the respiratory tract. Infection typically starts in the mucous membranes of the nose and throat but an infectious virus may also be transmitted directly to the lower respiratory tract (LRT) (Schmidt A C et al. Expert Rev Respir. Med. 2012).

Epidemiology and Clinical Features

Approximately 18,000 infants and children are hospitalized each year in the United States because of lower respiratory tract infections (LRTIs) caused by PIV3. Bronchiolitis and pneumonia are the most common clinical presentations (Henrickson K J Clin. Microbiology Rev. 2003). In addition to young children, PIV3 is highly problematic in immunocompromised children and adults like transplant recipients. For example, between 5-7% of adult HSCT recipients become infected with PIV3; approximately 24-50% of whom develop severe LRTIs like pneumonia and 22-75% of these patients die from respiratory failure (Henrickson K J Clin. Microbiology Rev. 2003). A retrospective study found that 25% of pediatric HSCT patients with PIV3 infection developed pneumonia and 33% died from it (Lujan-Zilbermann J et al. Clin Infect. Dis. 2001). Similarly, PIV3 has been shown to cause serious LRTIs and death (8%) in lung transplant recipients up to 5 years after transplantation (Vilchez R A. et al. Clin Infect. Dis. 2001).

Prevention and Treatment

Current approaches to PIV3 vaccines include intranasal administration of live attenuated strains, subunit strategies using the HN and F proteins, recombinant bovine/human viruses, and strains engineered using reverse genetics. In fact, two investigational vaccines, rhPIV3cp45 (or MEDI-560) an attenuated stain of PIV3 developed by cold passage, and B/hPIV3-RSV-F (or MEDI-534) a cDNA-derived chimeric bovine/human PIV3, are currently being tested in Phase I clinical trials. Analysis of safety and immunogenicity data is pending (Schmidt A C et al. Expert Rev Respir. Med. 2012).

Agents found to have in vitro antiviral activity against paramyxoviruses including PIV3 include neuraminidase inhibitors (e.g., zanamivir), protein synthesis inhibitors (puromycin), nucleic acid synthesis inhibitors, benzthiazole derivatives, 1,3,4-thiadizol-2-ylcyanamide, carbocyclic 3-deezaadenosine, ascorbic acid, calcium elenolate and extracts of *Sanicula europaea*. None of these compounds or drugs have yet found clinical applications (Henrickson K J Clin. Microbiology Rev. 2003).

Ribavirin is a guanosine analog used to stop viral RNA synthesis and viral mRNA capping. Anecdotal reports of decreased PIV3 shedding and clinical improvement have been reported in immunocompromised patients treated with aerosolized and oral ribavarin. However, a recent review at Fred Hutchinson Cancer Center demonstrated that established PIV3 pneumonias responded poorly to aerosolized ribavarin (Nicholas W G et al. Biol. Blood Marrow Transpl. 2001). Currently there are no antiviral drugs with proven clinical efficacy against PIV3 (Henrickson K J Clin. Microbiology Rev. 2003).

Immune Response and Correlates of Protection

PIV3 infections can induce potent humoral and cellular immune responses in the infected host. Both serum and mucosal neutralizing antibodies can provide lasting protection against disease (Schmidt A C et al. Expert Rev Respir. Med. 2012). Similarly, Cytotoxic T-lymphocyte responses appear to be important in the clearance of virus from the LRT during infections with PIV3 (Henrickson K J Clin. Microbiology Rev. 2003). Therefore assessing the immunodominant hierarchy of PIV3 is necessary to develop new therapeutic strategies.

Establishing a Hierarchy of Immunodominance for PIV3

Applying the process and TC-test described in Example 1, the following represents a novel characterization of T cell response for PIV3:

PIV3 was compartmentalized into the following fragments: HN, Protein C, PP, Large, M, N and Fusion. The percentage of responders were 88.2% for HN, 47% for Protein C, 47% for PP, 47% for Large, 94.1% for M, 64.7% for N and 47% for Fusion and the magnitude of response was 131 for HN, 214.6 for Protein C, 203.7 for PP, 115.8 for Large, 261.2 for M, 160 for N and 175.7 for Fusion. Applying the TC-test, we identified a TC-score of 912.91 for HN, 190.76 for Protein C, 181.07 for PP, 102.93 for Large, 3600 for M, 289.59 for N and 156.18 for Fusion (FIGS. 21 and 22). Applying the TC-score, the inventors ranked the different PIV3 antigens as follows (FIG. 23):

$$M>HN>\text{Large}>N>\text{Protein } C>PP>\text{Fusion}>\text{Large}$$

Hence, in order to provide protective immunity to a patient infected with PIV3, the following represents the identification of desired target or combination of targets (FIG. 13):

(a) the most immunodominant target antigen (Antigen M)
(b) a combination of the two most immunodominant targets (M+HN)
(c) a combination of the three most immunodominant targets (M+HN+N)
(d) a combination of the four most immunodominant targets (M+HN+N+Protein C)
(e) a combination of the five most immunodominant targets (M+HN+N+Protein C+PP)
(f) a combination of the six most immunodominant targets (M+HN+N+Protein C+PP+Fusion)
(g) a combination of the seven most immunodominant targets (M+HN+Large+N+Protein C+PP+Fusion+Large)

Example 4

Identification of Percentage of Responders

As shown in FIGS. 18 and 22, and as an example, the threshold of IFNγ production can be used to identify a critical level of T cell activity that can be used to determine responders vs. non-responders. However, one skilled in the art will recognize that this threshold is not exclusive to IFNγ production and can be substituted by any other biological marker produced (as in secreted by the cells and measured from the supernatant of a culture of cells) or expressed (as in a non-soluble marker fixed on a cellular membrane) by T cells upon the recognition with a relevant target including but not limited to IL2, Granzyme B, CD25, GM-CSF, and TNFα, for example. All such markers can be used to determine responders vs. non-responders by first identifying a threshold of unspecific response. The level of unspecific response can be identified by the magnitude of biological activity detected against an irrelevant antigen (e.g, an antigen not used in the initial T cell stimulation). For example, when analyzing the immune response to a virus encoding 5 antigens (A, B, C, D, E) an irrelevant antigen would be antigen F derived from a different virus or against unmanipulated PBMCs. This has been determined as 20 SFC per $2\times10^5$ for IFNγ and 10 SFC per $2\times10^5$ for Granzyme B, in specific embodiments. FIG. 24 shows an example where Granzyme B is used to determine a percentage of responders vs. non-responders for the characterization of an immune response against a pathogen.

Example 5

TC-Score Identifies Clinically Relevant Targets

To confirm the clinical relevance of the hierarchy established by the TC-score, the inventors analyzed the immune T cell response against PIV3 in a patient with active infection. As shown in FIG. 25, the frequency of PIV3-specific T cells targeting antigens M and N exhibit a particular enrichment between Day 155 and Day 162, correlating with a subsequent improvement in clinical symptoms, which subsided by Day 167. Another example of clinical relevance of PIV3 T cells to control viral infection is shown in FIG. 26, where an increase in the frequency of PIV3-specific T cells had an inverse correlation with the symptoms of infection and viral detection by PCR present in a single representative patient with active infection post bone marrow transplant (BMT).

Figure 27:
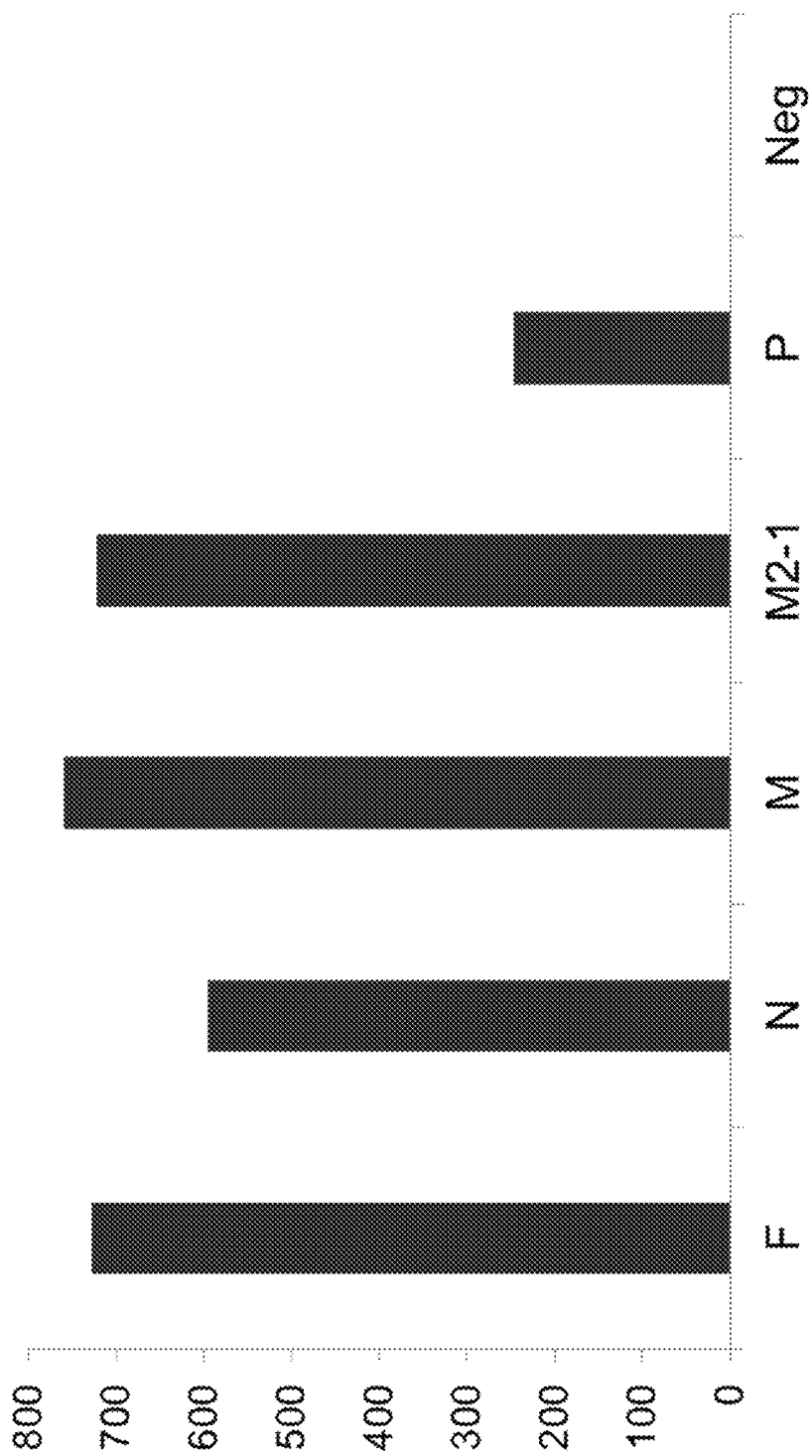
FIG. 27 illustrates the clinical relevance of the immune T cell response against different hMPV antigens.

FIG. 27 illustrates the clinical relevance of the immune T cell response against different hMPV antigens. This figure shows the frequency of T cells reactive against proteins F, N, M, M2-1 and P detected in a single representative patient with active HMPV infection, whose symptoms resolved after detection of these T cells in peripheral blood.

Targeting Top-Ranked Antigens Using T-Cells

Figure 28:
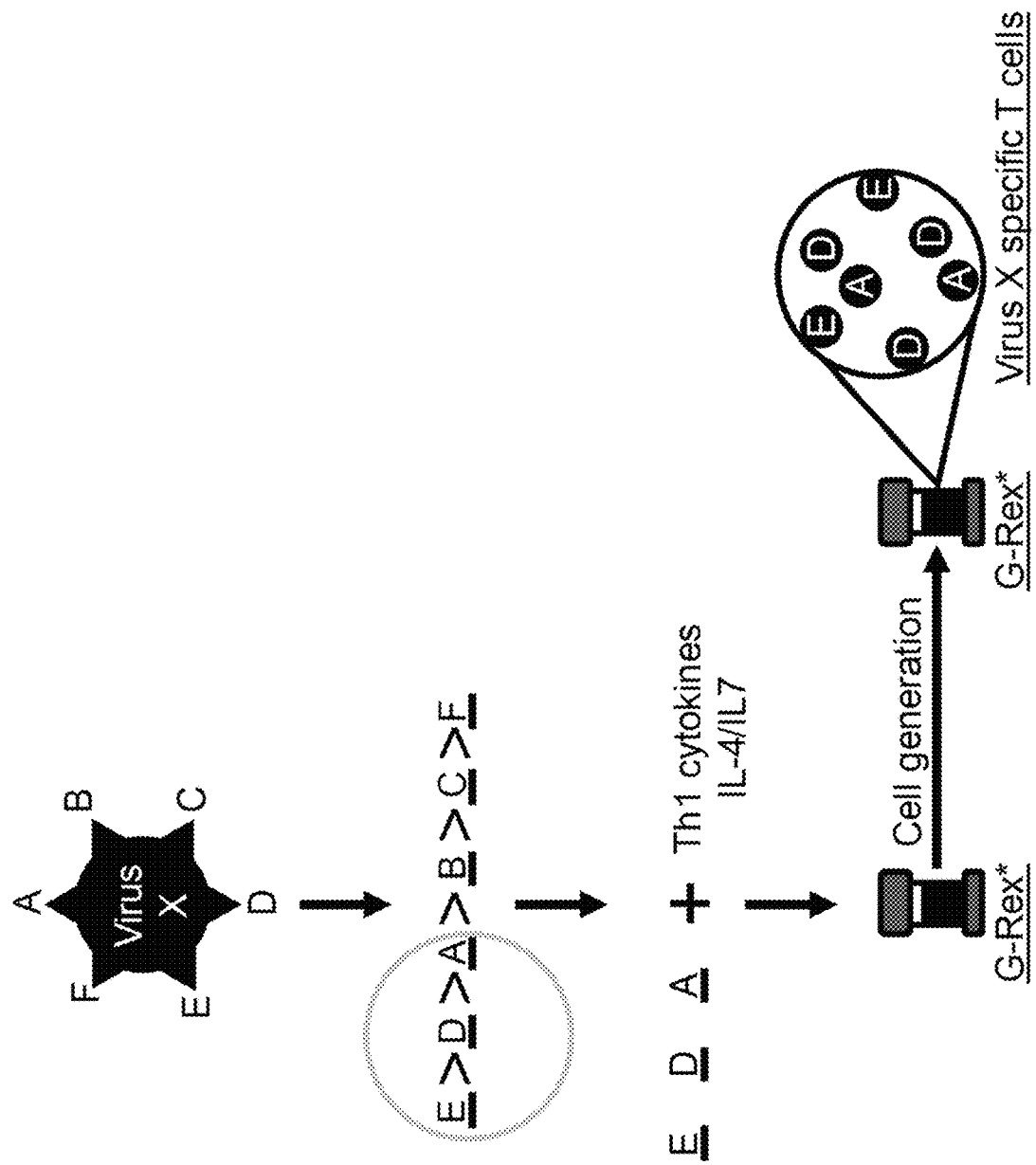
FIG. 28 illustrate a therapeutic application of ranking where the top targets of a Virus X are identified as a source of antigen.
Figure 29:
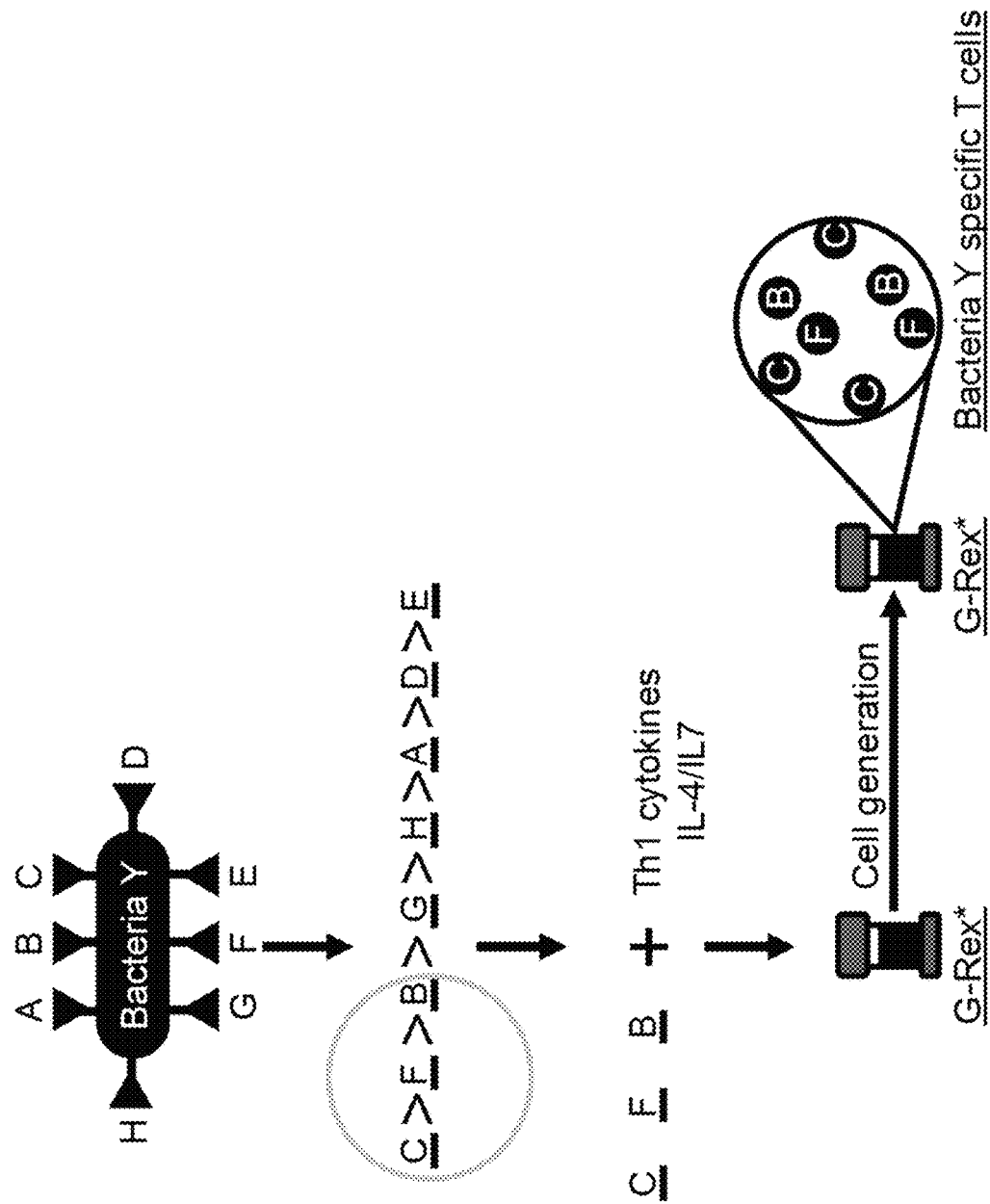
FIG. 29 illustrate a therapeutic application of ranking where the top targets of a Bacteria Y are identified as a source of antigen.
Figure 30:
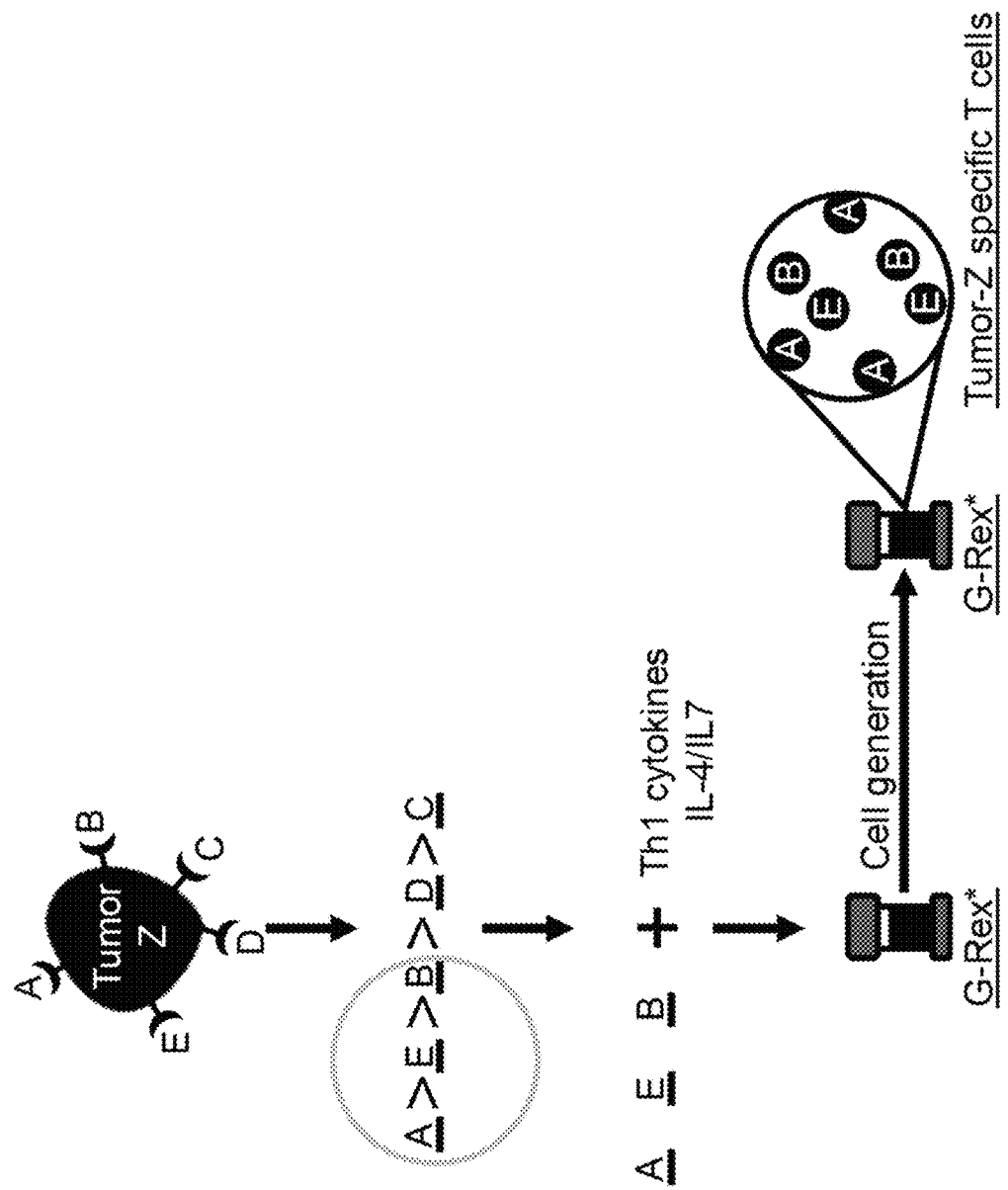
FIG. 30 illustrate a therapeutic application of ranking where the top targets of a Tumor Z are identified as a source of antigen.

FIGS. 28, 29, and 30 illustrate the therapeutic application of this ranking where the top targets of a given pathogen or cancer are identified as a source of antigen. Culture conditions with this will then result in a subsequent enrichment of T cells specific for the given targets.

Generation of PIV3-Specific T Cells for Therapeutic Use

Figure 31:
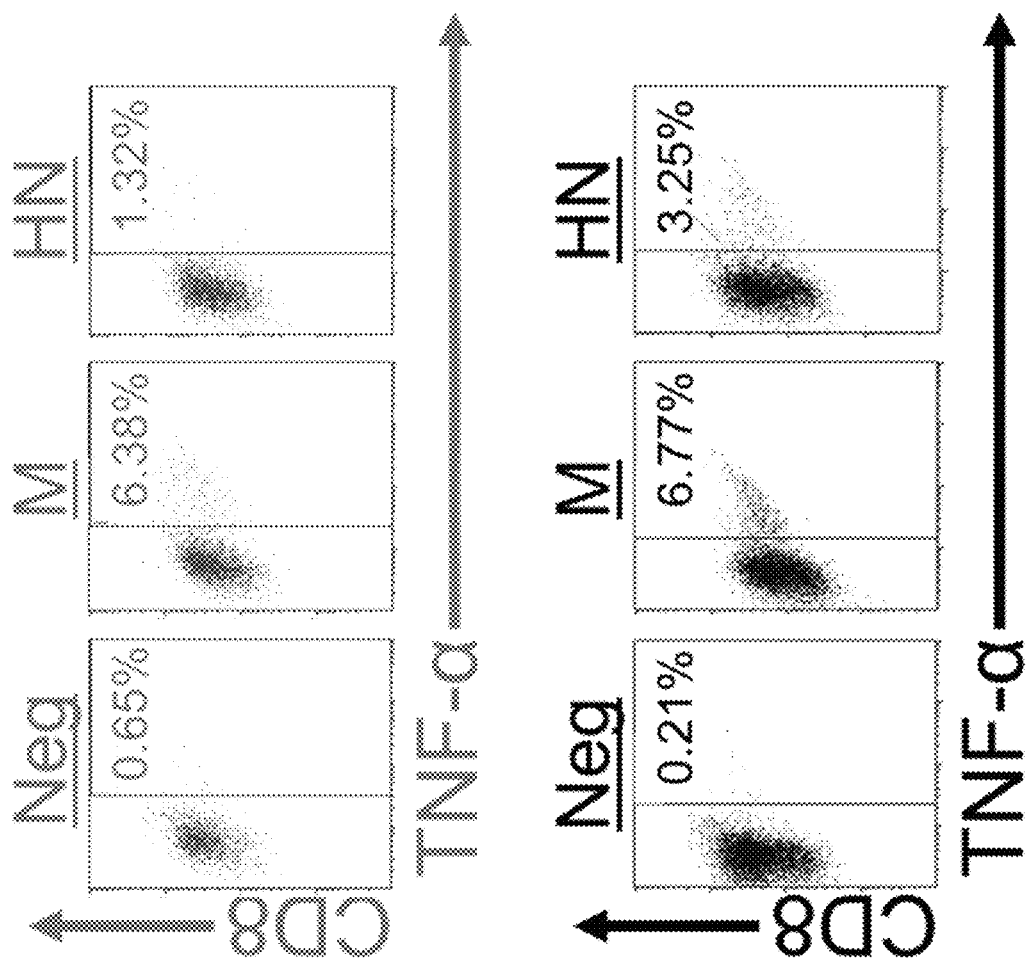
FIG. 31 demonstrates phenotypic characteristics of a T cell product.
Figure 32:
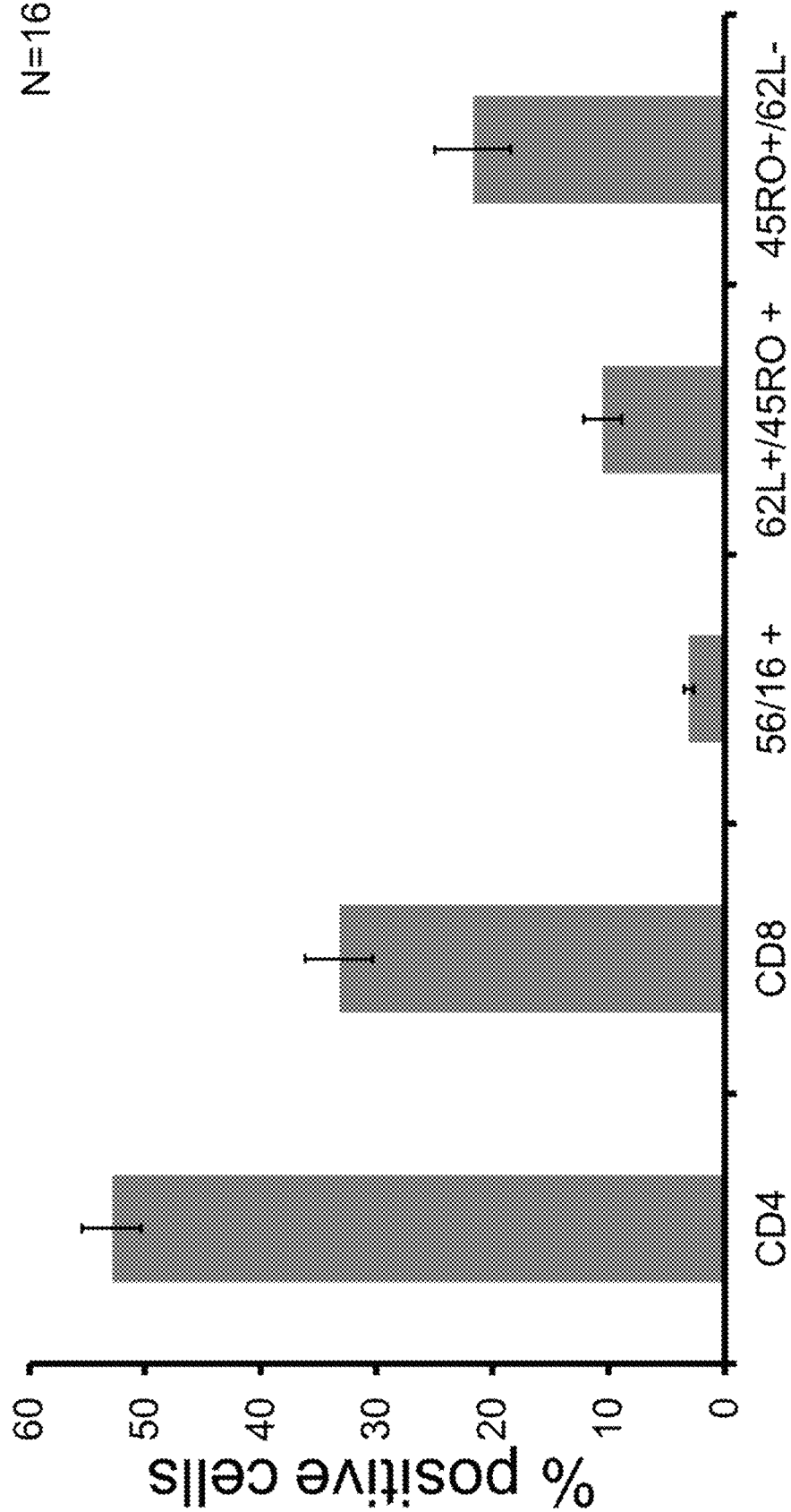
FIG. 32 shows the antigen specificity of CD4+ and CD8+ as detected by intracellular cytokine staining for antigens M and HN.

PBMCs isolated from healthy PIV3-seropositive individuals were cultured with peptides overlapping the entire proteins M and HN in the presence of Th1-polarizing cytokines for a period of 10 days. FIG. 31 shows the phenotypic characteristics of a T cell product and FIG. 32 shows the antigen specificity of CD4+ and CD8+ as detected by intracellular cytokine staining for antigens M and HN.

Generation of hMPV-Specific T Cells for Therapeutic Use

Figure 33:
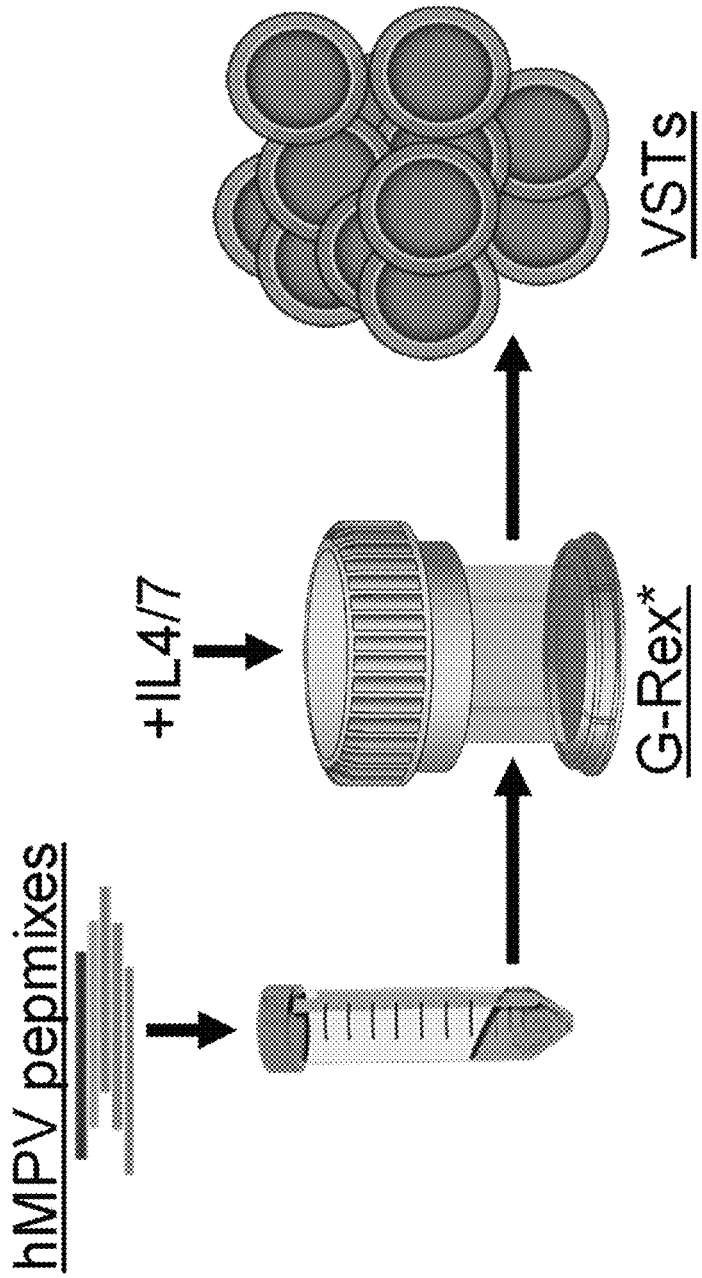
FIG. 33 illustrates one example of hMPV T cell manufacture.
Figure 34:
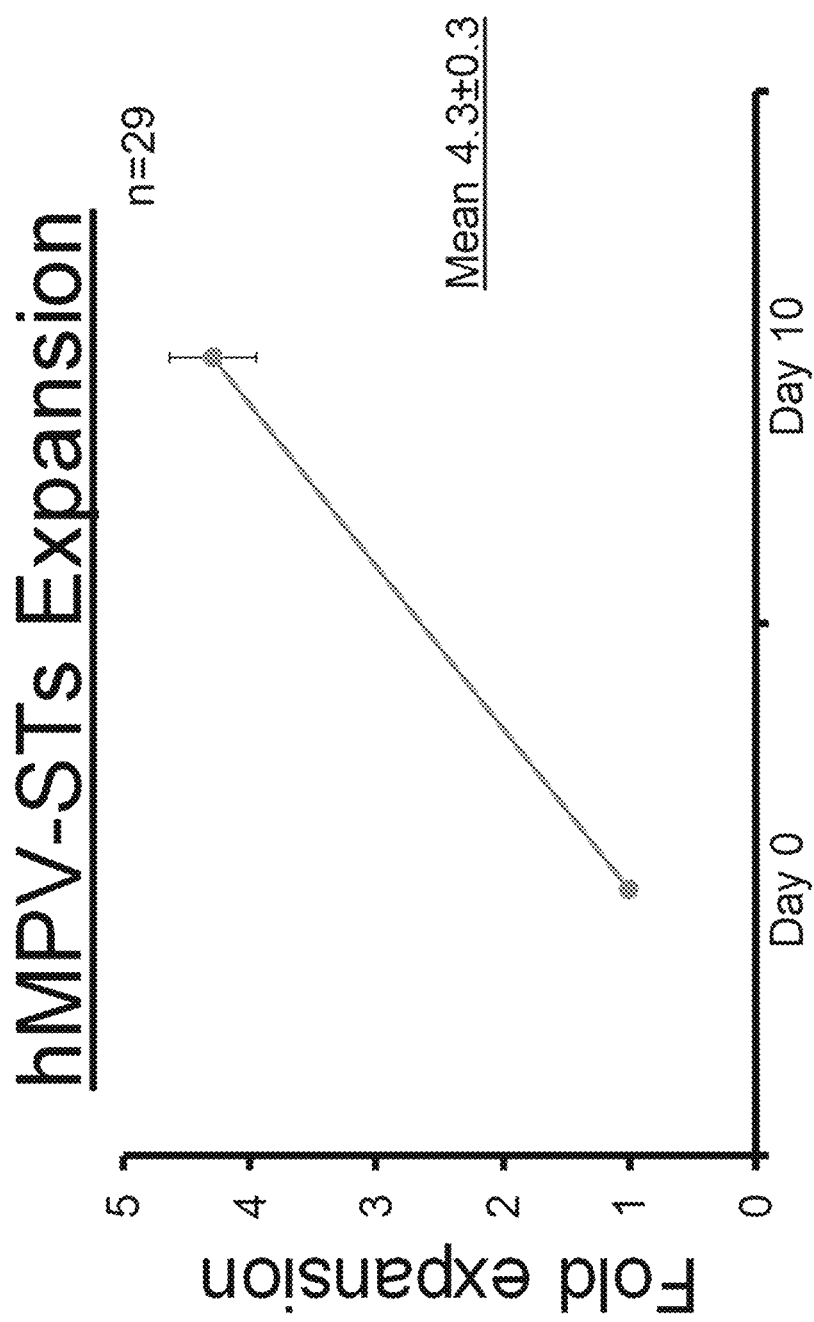
FIG. 34 demonstrates expansion of T cells from an example as shown in FIG. 33.
Figure 35:
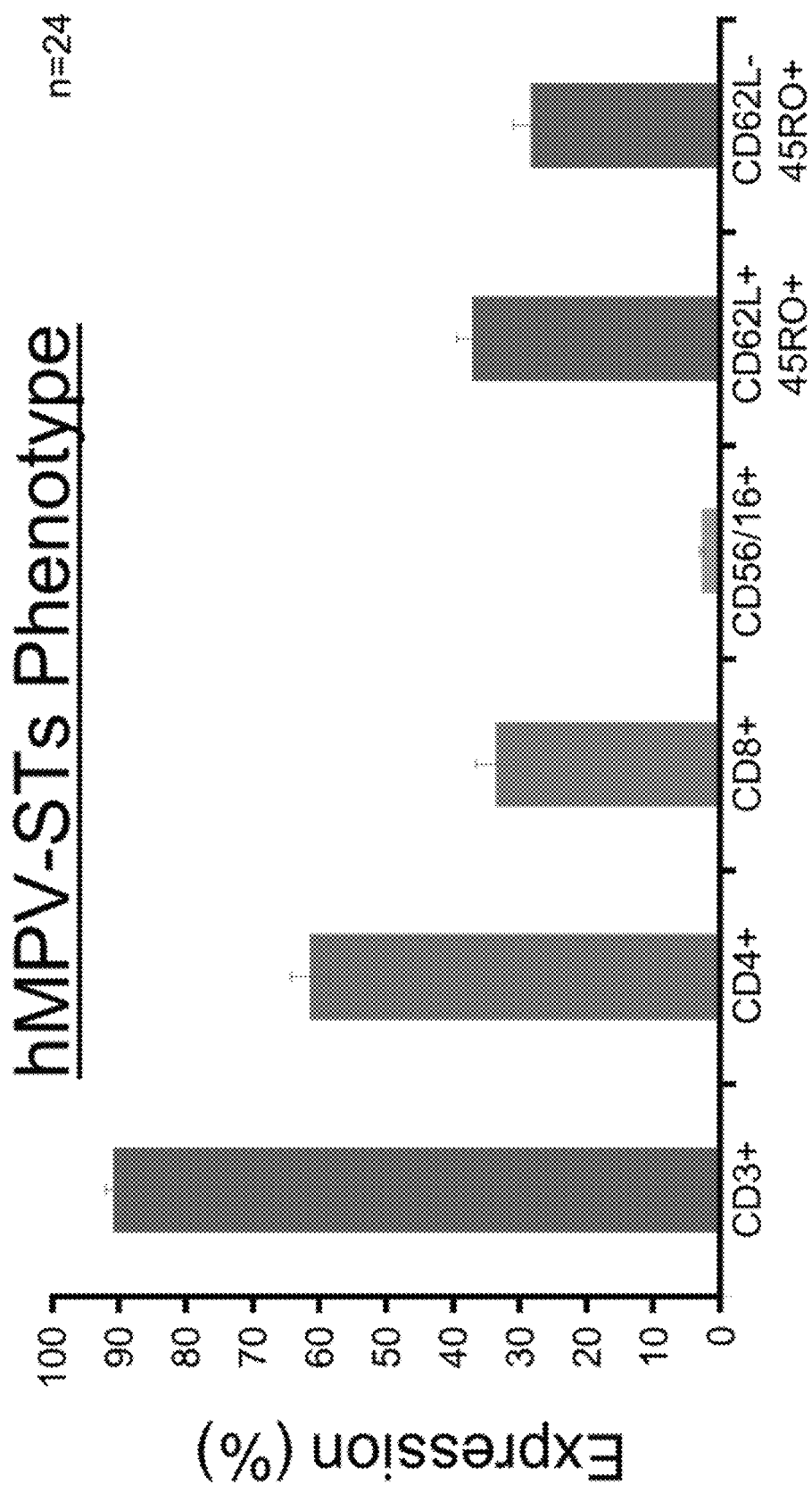
FIG. 35 shows the phenotype of hMPV STs.
Figure 36:
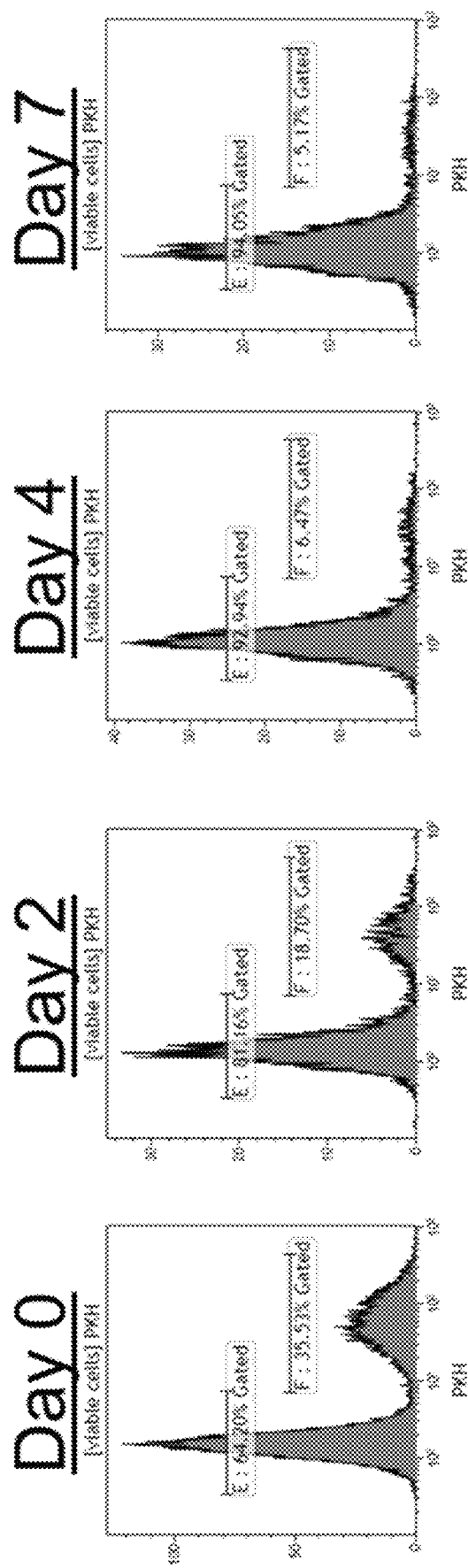
FIG. 36 provides results of a culture with HMVP-specific T cells resulted in a progressive decline in the HMPV target cells.
Figure 37:
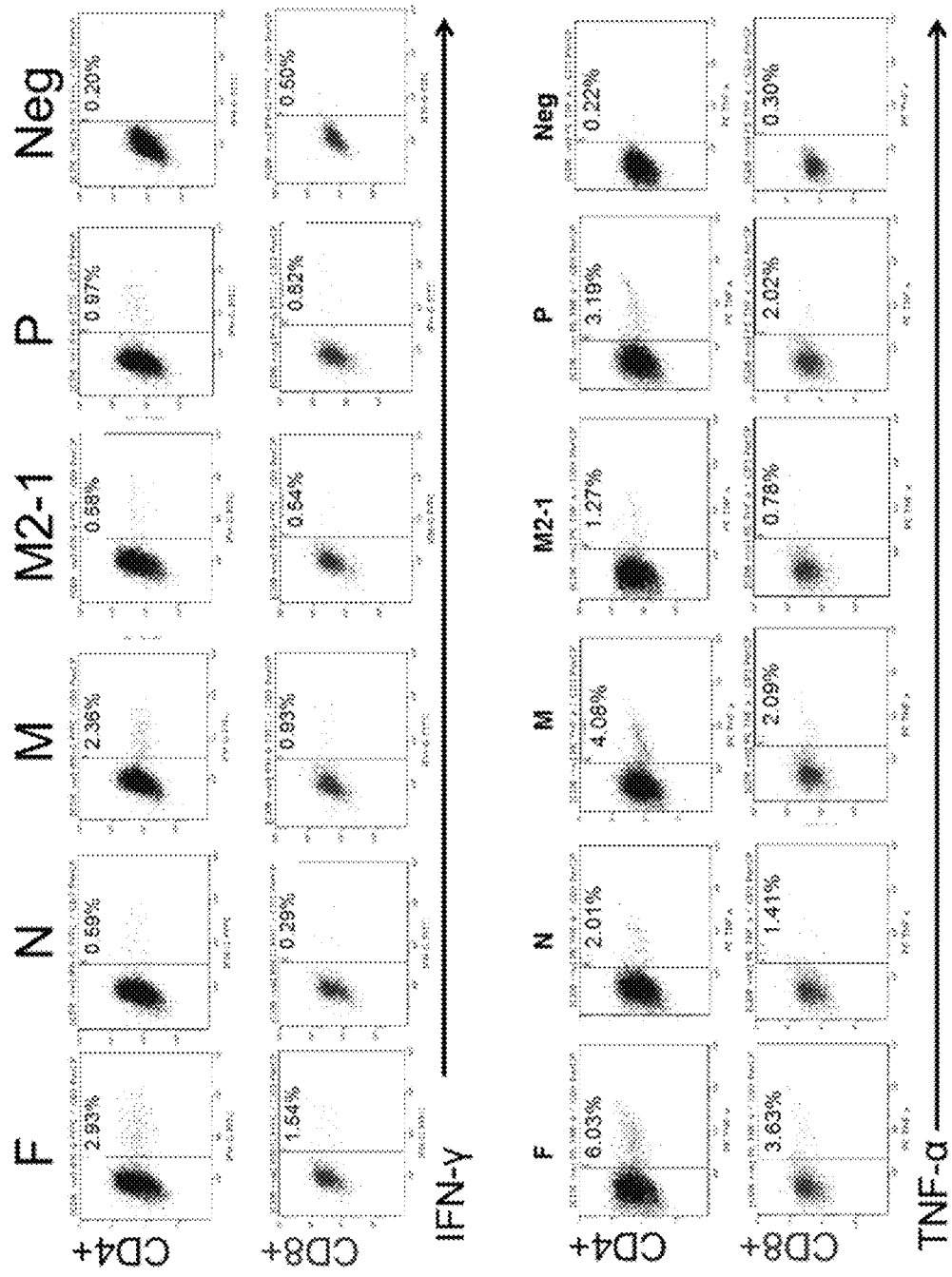
FIG. 37 shows that the cells in FIG. 35 were antigen-specific as detected by intracellular cytokine staining for relevant antigens.

PBMCs isolated from healthy hMPV-seropositive individuals were cultured with peptides overlapping the entire protein in the presence of Th1-polarizing cytokines using the G-Rex culture system (or any other cell culture platform, bioreactor or tissue culture plates) for a period of 10 days as illustrated in FIG. 33. This process resulted in the significant expansion of T cells as illustrated in FIG. 34. Upon examination, these expanded cells were polyclonal (FIG. 35) and found to be antigen-specific as detected by intracellular cytokine staining for relevant antigens (FIG. 37). To evaluate the antiviral properties of this expanded T cell product, HLA matched target cells were pulsed with HMPV peptides and labeled with PKH dye and cultured at a 1:1 ratio with HMPV-specific T cells. As shown in FIG. 36, the culture with virus-specific T cells resulted in a progressive decline in the HMPV target cells from 35.5% to 18.7% to 6.4% after Day 0, 2 and 4 of culture. Therefore, as time progresses, there is killing of infected cells.

Example 6

Identification of Clinical Efficacy for a Product

Product Composition

The inventors have identified examples of biological features of a final product that correlate with clinical efficacy, in certain embodiments.

In specific embodiments, the following description of how to identify if a product will have clinical efficacy in a patient is unrelated to other embodiments herein that concern determination of hierarchy of immunogenicity of antigens for a pathogen. That is, T cells having certain antigens may be subjected to the characterization methods below whether or not their respective antigen was selected based on an immunogenic hierarchy or was based on other methods of antigen selection, or is random.

Characterization of Virus-Specific T Cells

Identity: In some cases, the identity of the cells may be determined by HLA typing. The final product comprises donor-derived cells, in at least some cases. Therefore, the HLA type of the final product should be identical to that of the donor blood in certain embodiments.

Phenotypic analysis: Optimal in vivo T cell persistence and activity requires both helper (CD4+) and cytotoxic (CD8+) T cells. Phenotypic analysis may therefore be used to determine if product is comprised of polyclonal T cells.

Specificity: The antiviral specificity of product can be assessed in vitro by exposing the expanded cells to each of the individual synthetic peptide libraries and assessing their capacity to recognize each of the synthetic peptide libraries. For example, one method to assess product specificity involves testing the ability of these cells to produce cytokine interferon gamma (IFNγ) following synthetic peptide exposure using an IFNγ ELIspot test. In this test, cells are re-exposed to each of the viral antigens used for stimulation. Product is considered specific for Virus X when the sum of IFNγ-producing spot-forming cells (SFCs) directed against all antigens from target virus was ≥20 SFCs per $2\times10^5$ input cells (as an example of a threshold of activity).

Cytotoxicity: The cytotoxic specificity of product can be measured in a standard killing assays, where cells are used as effectors and the targets are, for example, chromium-labeled PHA blasts pulsed with the relevant pepmixes. Effector to target ratios may be (or may be at least or no more than): 5:1, 10:1, 15:1, 20:1, 25:1, 30:1, 35:1, 40:1, 45:1, 50:1, 55:1; 60:1, 65:1, 70:1, 75:1, 80:1, 85:1, 90:1, 95:1, etc. Autologous or allogeneic PHA blasts alone or loaded with irrelevant pepmixes can be used as specificity and alloreactivity controls. For example, a pProduct is considered to show cytotoxicity specificity against Virus X if the percentage of specific lysis of PHA blasts pulsed with relevant pepmixes is ≥10% at a 40:1 Effector effector to target ratio, in at least certain cases Killing of target cells at a given effector to target ratio is considered antigen-specific when above a baseline level (established using either unmanipulated PBMCs as effectors or assessing the activity of the T cell product against target cells pulsed with an irrelevant antigen).

The following represents a mathematical representation that allows one skilled in the art to identify a product composition:

Product Definition

The product is defined as T cells isolated from in vitro culture characterized by:

$$(_RTB)+(_RTK)\geq 1$$

where $_RTB$ is defined as [(Thio-P)+1]/[(Tbio-U)+1], which when ≥1 will be equivalent to an $_RTB$ value of 1 and when <1 will correspond to an $_RTB$ value of 0; and $_RTK$ is defined as [(% TSpec-P)/TCSpec], which when ≥1 will be equivalent to an $_RTK$ value of 1 and when <1 will correspond to an $_RTK$ value of 0 (see FIG. 38).

Tbio-P is defined as the biological activity of the in vitro T cell product and Tbio-U is the biological activity of the noise threshold, which as previously described can be the biological activity of unmanipulated PBMCs when in the presence of an antigen of interest or the biological activity of the in vitro T cell product when in the presence of an irrelevant antigen that is not of interest. Such biological activity could include, but is not limited to, IFNγ, IL2, GM-CSF and TNFα production for example and the upregulation of markers such as CD25, CD45, CD27, CD28, CD69 and CD107 for example.

TSpec-P, or the specific killing ability of the in vitro T cell product, is defined as the percentage of lysed HLA-matched target cells expressing the cognate antigen at a predefined effector to target ratio, (e.g., 40:1 effector to target ratio) after subtracting the percentage of unspecific killing by unmanipulated PBMCs of target cells expressing an irrelevant peptide, i.e. an antigen or marker not present within the pathogen or tumor of interest at a predefined effector to target ratio.

In the event that multiple products are available for clinical administration, the supplemental formula $[\alpha(_RTB)+\beta(_RTK)=\phi]$ can be applied to rank products in order of preference.

$$\alpha(_RTB)+\beta(_RTK)=\phi$$

Where $_RTB$ is defined as the value resulting from $[(\text{Tbio-P})+1]/[(\text{Tbio-U})+1]$ Where $_RTK$ is defined as the value resulting from $[(\% \text{TSpec-P})/\text{TCSpec}]$ where $\alpha$ and $\beta$ are defined as weighting coefficients dependent upon variables including but not limited to therapeutic applications, manufacturing processes, peptide mixtures, cell lines, etc.

where $\phi$ is defined as a clinical efficacy value that may be used to determine a ranking of clinical efficacy among therapeutic products Example 1 is an example of biological characteristics present in a product.
  Tbio-P=200 SFC per 2×10⁵ IFNγ
  Thio-U=50 SFC per 2×10⁵ IFNγ
  TSpec-P=40%
  TCSpec=10%
  α=1
  β=5
  $_RTB=[(\text{Thio-P})+1]/[(\text{Thio-U})+1]$
  $_RTB=[(200)+1]/[(50)+1]=3.94$
  Therefore,
  $_RTB=1$
  $_RTK=[(\text{TSpec-P})/(\text{TCSpec})]$
  $_RTK=[(40\%)/(10\%)]=4$
  Therefore,
  $_RTK=1$
Therefore, this example constitutes a product as defined by $(_RTB)+(_RTK) \geq 1$. In addition, the clinical efficacy of this product is 23.94 as defined by $\alpha(_RTB)+\beta(_RTK)=4$.

Example 2 is an example of biological characteristics present in a product.
  Tbio-P=100 SFC per 2×10⁵ Granzyme B
  Thio-U=10 SFC per 2×10⁵ Granzyme B
  TSpec-P=5%
  TCSpec=10%
  α=1
  β=5
  $_RTB=[(\text{Thio-P})+1]/[(\text{Thio-U})+1]$
  $_RTB=[(100)+1]/[(10)+1]=9.18$
  Therefore,
  $_RTB=1$
  $_RTK=[(\text{TSpec-P})/(\text{TCSpec})]$
  $_RTK=[(5\%)/(10\%)]=0.5$
  Therefore,
  $_RTK=0$
Therefore, Example 2 constitutes a product as defined by $(_RTB)+(_RTK) \geq 1$. In addition, the clinical efficacy of this product is 11.68 as defined by $\alpha(_RTB)+\beta(_RTK)=\phi$.

Because Examples 1 and 2 both constitute a product as defined by $(_RTB)+(_RTK) \geq 1$, the clinical efficacy value ($\phi$) will aid in determining product selection if a patient is eligible to receive both products from Example 1 and 2. A greater $\phi$ value represents a product with higher specificity and killing ability and therefore, products can be ranked. In this case, Example 1 constitutes a 'superior' product for administration to a patient based on its $\phi$ clinical efficacy variable.

Example 3 is an example of biological characteristics not present in a product.
  Tbio-P=50 SFC per 2×10⁵ IL2
  Tbio-U=70 SFC per 2×10⁵ IL2
  TSpec-P=9%
  TCSpec=10%
  α=1
  β=5
  $_RTB=[(\text{Thio-P})+1]/[(\text{Thio-U})+1]$
  $_RTB=[(50)+1]/[(70)+1]=0.7$
  Therefore,
  $_RTB=0$
  $_RTK=[(\text{TSpec-P})/(10\%)]$
  $_RTK=[(9\%)/(10\%)]=0.9$
  Therefore,
  $_RTK=0$
Therefore, Example 3 does not constitute a product as defined by $(_RTB)+(_RTK) \geq 1$.

Example 7

Product Manufacture

A product defined as in vitro T cells characterized by $(_RTB)+(_RTK) \geq 1$ can be attained through various manufacturing processes. The description below concerns embodiments for the determination of whether or not certain T cells are therapeutically useful. The following represent some manufacturing examples:

1. Manufacture and Cryopreservation of Virus-Specific T Cells

Mononuclear cells from peripheral blood or leukapheresis product from healthy donors are contacted with one or more overlapping synthetic peptide libraries encompassing all or part of the sequence of one or more of the antigens expressed by Virus X. Following synthetic peptide exposure antigen-specific T cells within mononuclear cells are activated and expand in an in vitro manufacturing process. In this example, Mononuclear cells will be activated and expanded for 9-11 days in vitro by adding them to a gas-permeable culture device (such as a G-Rex culture device) or tissue culture plates along with T cell media supplemented with the Th1 cytokines such as but not limited to IL7 and IL4 and clinical grade peptide mixtures (pepmixes) spanning the entire sequence of one or more antigens of Virus X. In addition to clinical grade peptide mixtures (pepmixes), one skilled in the art will recognize that the source of antigen could also include, for example, recombinant proteins, DNA, RNA encoding for an antigen(s), and so forth of the virus. In specific cases, the product meets the criteria set by $(_RTB)+(_RTK) \geq 1$, therefore it can be cryopreserved for future clinical use, for example.

Alternatively, additional antigen stimulations can be performed (on days 10-13 of culture) where antigen presenting cells that can either be autologous mononuclear cells (or) OKT3 blasts (or) PHA blasts (as examples) are pulsed again with the pepmixes specific for one or more antigens of Virus X and then irradiated (80 Gy) and subsequently used as stimulators. At the time of the 2nd stimulation cultures will be supplemented Th1 cytokines (such as but not limited to IL4+IL7, IL15, IL2, IL21, IL12 or combinations thereof) and 3 days later cultures are supplemented with IL2, or IL15, IL7, IL21, IL4 or combinations thereof. After 19-23 days in culture, cells specific for Virus X are harvested from the G-Rex culture device or tissue culture plates, pooled into appropriately-sized sterile containers and counted. The cells are washed by centrifugation and are then re-suspended in ice cold freezing medium up to a concentration of $1 \times 10^7$ cells/mL, in suitable aliquots for patient infusion. At this time, or within 7 days of freezing, an appropriate number of cells, culture supernatants pre and post washes, and aliquots of final cell suspension may be submitted for endotoxin testing and microbiological screens. At the same time, an appropriate number of cells may be taken for product characterization that includes HLA typing, phenotypic, specificity and/or cytolytic function, for example.

Figure 40:
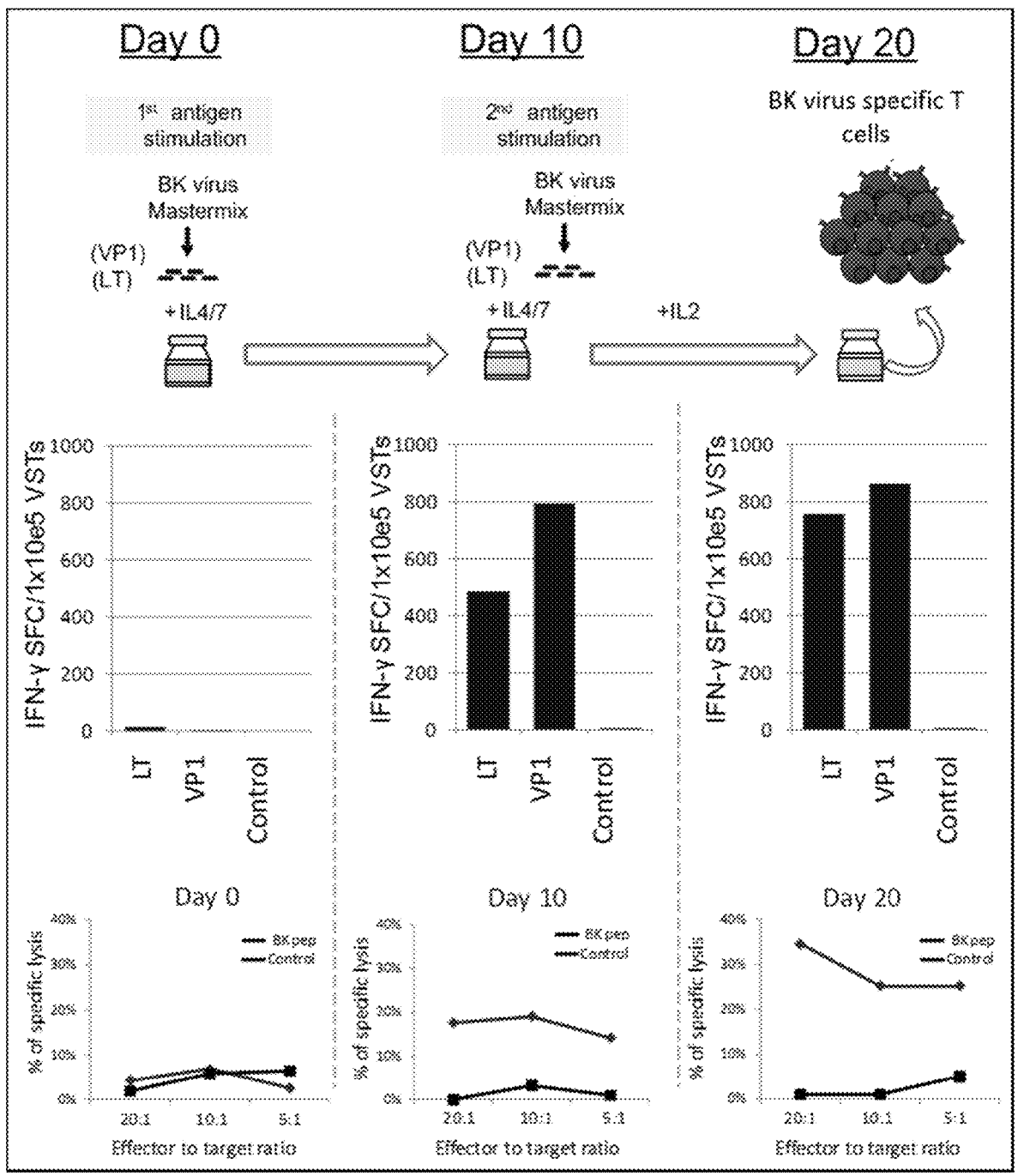
FIG. 40 demonstrates specificity and cytolytic capability of the cultures was assessed on Day 0, 10 and 20 for BK virus specific T cells.
Figure 41:
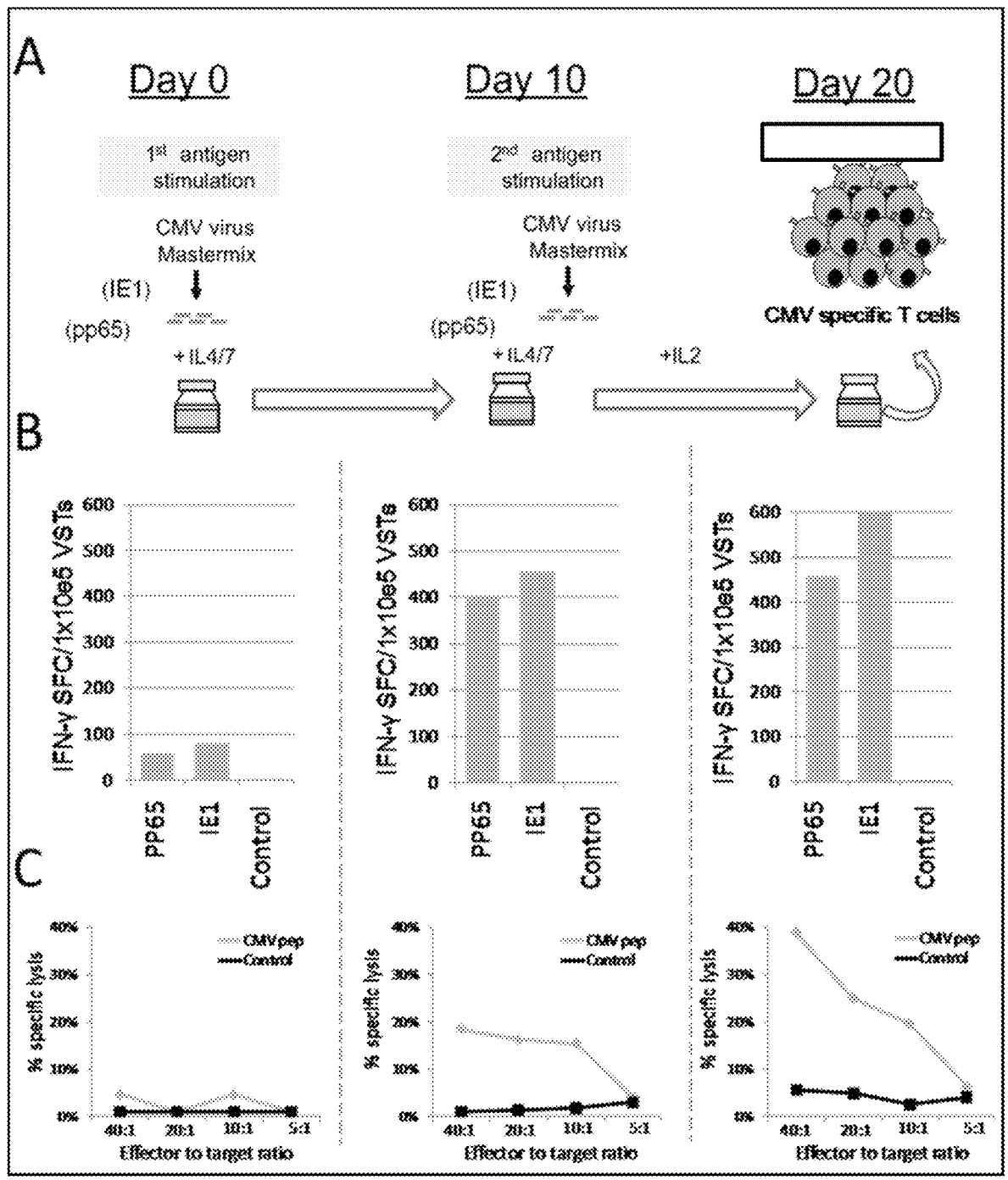
FIG. 41 demonstrates specificity and cytolytic capability of the cultures was assessed on Day 0, 10 and 20 for CMV specific T cells.

In specific embodiments, the time following the first antigen stimulation until the second antigen stimulation (see FIGS. 39-41 as examples) may be any suitable time and may vary depending on a variety of reasons, such as the antigen being utilized, for example. In particular embodiments the number of days between the first antigen stimulation and the second antigen stimulation is (or is at least or no more than) 1, 2, 3, 4, 5, 6, 7, 8, 9, 10, 11, 12, 13, 14, 15, 16, 17, 18, 19, 20, 21, 25, 30, 35, 40, 45, 50, or more days. In other embodiments, the time following the second antigen stimulation may be any suitable time and may vary depending on a variety of reasons, such as the antigen being utilized, for example. In particular embodiments the number of days between the second antigen stimulation and a subsequent step (such as an endpoint for the culture, a testing of the cells, a therapeutic use of the cells, and so forth) is (or is at least or no more than) 1, 2, 3, 4, 5, 6, 7, 8, 9, 10, 11, 12, 13, 14, 15, 16, 17, 18, 19, 20, 21, 25, 30, 35, 40, 45, 50, or more days.

2. Characterization of Virus-Specific T Cells

Identity: The identity of the cells will be determined by HLA typing. The final product consists of donor-derived cells. Therefore the HLA type of the final product should be identical to that of the donor blood.

Phenotypic analysis: Optimal in vivo T cell persistence and activity requires both helper ($CD4^+$) and cytotoxic ($CD8^+$) T cells. Phenotypic analysis is therefore used to determine if product is composed of polyclonal T cells.

Specificity: The antiviral specificity of product can be assessed in vitro by exposing the expanded cells to each of the individual synthetic peptide libraries and assessing their capacity to recognize each of the synthetic peptide libraries. For example, one method to assess product specificity involves testing the ability of these cells to produce cytokine interferon gamma (IFNγ) following synthetic peptide exposure using an IFNγ ELIspot test. In this test cells are reexposed to each of the viral antigens used for stimulation. Product is considered specific for Virus X when the sum of IFNγ-producing spot-forming cells (SFCs) directed against all antigens from target virus was ≥20 SFCs per $2 \times 10^5$ input cells.

Cytotoxicity: The cytotoxic specificity of product can be measured in a standard killing assays, where cells are used as effectors and the targets are PHA blasts pulsed with the relevant pepmixes. Autologous or allogeneic PHA blasts alone or loaded with irrelevant pepmix can be used as specificity and alloreactivity controls. Product is considered to show cytotoxicity against Virus X if the percentage of specific lysis of PHA blasts pulsed with relevant pepmixes is ≥10% at a 40:1 Effector to target ratio.

3. Data

The methods for manufacture and characterization of T-cells specific for immunodominant antigens of a virus as described above were used to generate T-cells specific for Adenovirus (AdV), BK virus (BKV) and Cytomegalovirus (CMV), as examples only.

3.1 Adenovirus

Adenovirus remains a major cause of morbidity and mortality in immunocompromised individuals, in whom it may produce pneumonia, hemorrhagic cystitis, nephritis, colitis, hepatitis, and encephalitis. The most frequently used drug for disease treatment is Cidofovir, but the clinical benefit in patients with overt viral disease is limited and the associated nephrotoxicity is a major concern. Moreover, in the absence of prospective, randomized, controlled trials, the efficacy of the drug remains uncertain (Leen A M et al. Biol. Blood Marrow Transpl. 2006). Given that viral clearance has been shown to correlate with the detection of circulating AdV-specific T cells adoptive T cell transfer has been considered as an alternative therapeutic option (Feuchtinger T. et al. Br. J. Hematol. 2005)

Figure 39:
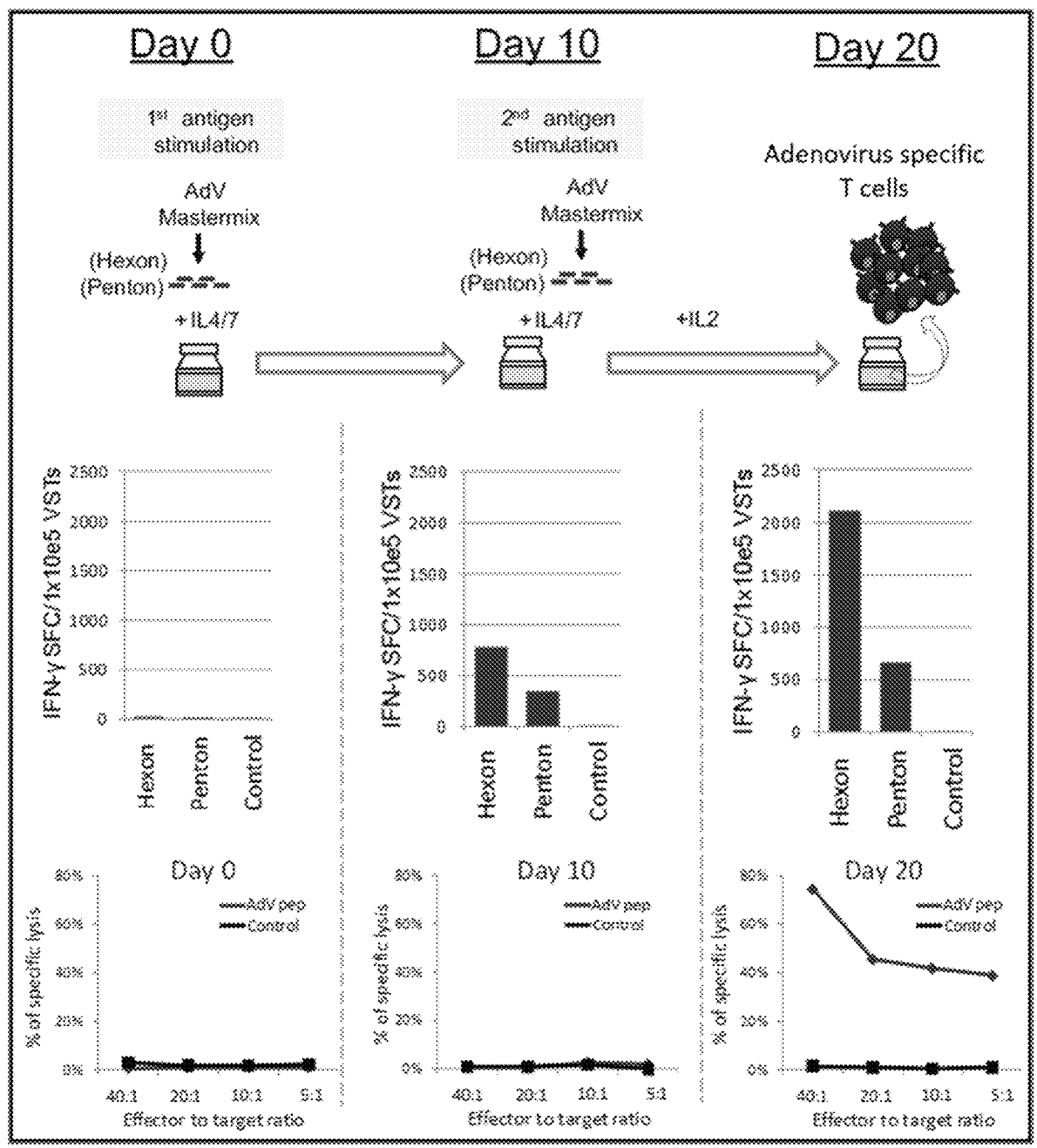
FIG. 39 demonstrates specificity and cytolytic capability of the cultures was assessed on Day 0, 10 and 20 for adenovirus-specific T cells.

To generate Adenovirus-specific T cells, mononuclear cells from peripheral blood product from healthy donors were activated and expanded in vitro by adding them to a GRex culture device along with T cell media supplemented with the cytokines IL7 and IL4 and clinical grade peptide mixtures (pepmixes) spanning the entire sequence of the most immunodominant antigens of Adenovirus, namely Hexon and Penton. For the second stimulation (on days 10-13 of culture) autologous PBMCs were pulsed again with the pepmixes specific for Hexon and Penton and then irradiated (80 Gy) and subsequently used as APCs followed by expansion in media supplemented with IL4 and IL7 and later supplemented with IL2. The specificity and cytolytic capability of the cultures was assessed on Day 0, 10 and 20 as shown in FIG. 39. Compared to unmanipulated PBMCs on Day 0, cultures on Day 10 showed a substantial increase in the frequency of Hexon- and Penton-directed T cells (28.7 and 32.3 fold increase, respectively) as evidenced by >20 IFNγ-producing SFCs. Cultures on Day 20 showed further increase in T cell specificity (2.7 and 1.9 fold increase in Hexon or Penton-reactive cells, respectively) over Day 10 cultures. Importantly the cultures on Day 20 contained cells that received a second stimulation which conferred the expanded cells with the ability to kill antigen-loaded target cells as evidenced by >10% cytotoxicity of Adenovirus antigen loaded target cells.

3.2 BK Virus

BKV is a ubiquitous polyomavirus that establishes a latent, asymptomatic infection in >90% of the general population. In both solid organ and HSCT allograft recipients, however, viral reactivation is frequent and correlates with the absence of circulating BKV-specific T cells. Thus, urinary shedding of BKV occurs in 60-80% of HSCT recipients (Tomblyn M et al. Bone Marrow Transpl. 2009), and develops into BKV-associated hemorrhagic cystitis (PVHC) in 5-15%, resulting in prolonged hospital stays, severe morbidity and increased mortality. Currently there are still no approved antiviral agents for treatment of BK virus infection.

To generate BK virus-specific T cells, mononuclear cells from peripheral blood from healthy donors were activated and expanded in vitro by adding them to a GRex culture device along with T cell media supplemented with the cytokines IL7 and IL4 and clinical grade peptide mixtures (pepmixes) spanning the entire sequence of the most immunodominant antigens of BK virus, namely LT and VP1. For the second stimulation (on days 10-13 of culture) autologous PBMCs were pulsed again with the pepmixes specific for LT and VP1 and then irradiated (80 Gy) and subsequently used as APCs followed by expansion in media supplemented with IL4 and IL7 and later supplemented with IL2. The specificity and cytolytic capability of the cultures was assessed on Day 0, 10 and 20 as described above and shown in FIG. 40. Compared to naïve cultures on Day 0, cultures on Day 10 showed a substantial increase in the frequency of LT and VP1-specific T cells (316.8 and 38.6 fold increase, respectively) as evidenced by >20 IFNγ-producing SFCs. Cultures on Day 20 showed further increase in T cell specificity (2.7 and 1.9 fold increase in LT and VP1-reactive cells, respectively) over Day 10 cultures. Importantly these cultures contained cells that received a second stimulation which conferred the expanded cells with the ability to kill antigen-loaded target cells as evidenced by >20% cytotoxicity of BK virus antigen loaded target cells.

3.3 Cytomegalovirus

Cytomegalovirus (CMV) is a latent beta-herpes virus that usually causes an asymptomatic infection in immunocompetent individuals. It persists in approximately 70% of healthy adults and replicates in epithelial cells, fibroblasts and monocytes. Reactivation of CMV in the stem cell recipient can result in significant morbidity and mortality, with clinical manifestations including interstitial pneumonitis, gastroenteritis, fevers, hepatitis, encephalitis and retinitis (Boeckh M et al. Biol. Blood Marrow Transpl. 2003). Cell-mediated immunity is considered the most important factor in controlling CMV infection and CMV-specific CD4+ and CD8+ lymphocytes play an important role in immune protection from both primary infection and subsequent reactivations.

To generate CMV-specific T cells, mononuclear cells from peripheral blood from healthy donors were activated and expanded in vitro by adding them to a GRex culture device along with T cell media supplemented with the cytokines IL7 and IL4 and clinical grade peptide mixtures (pepmixes) spanning the entire sequence of the most immunodominant antigens of CMV, namely IE1 and pp65. For the second stimulation (on days 10-13 of culture) autologous PBMCs were pulsed again with the pepmixes specific for IE1 and pp65 and then irradiated (80 Gy) and subsequently used as APCs followed by expansion in media supplemented with IL4 and IL7 and later supplemented with IL2. The specificity and cytolytic capability of the cultures was assessed on Day 0, 10 and 20 as described above and shown in FIG. 41. Compared to naïve cultures on Day 0, cultures on Day 10 showed a substantial increase in the frequency of IE1 and pp65 (6.66 and 5.7 fold increase, respectively) as evidenced by >20 IFNγ-producing SFCs. Cultures on Day 20 showed further increase in T cell specificity (1.1 and 1.4 fold increase in IE1 and pp65-reactive cells, respectively) over Day 10 cultures. Importantly these cultures contained cells that received a second stimulation which conferred the expanded cells with the ability to kill antigen-loaded target cells as evidenced by >20% cytotoxicity of CMV antigen loaded target cells.

In this section the manufacture and characterization of T cells specific for one or more immunodominant antigens of a virus is described. By providing 3 examples—AdV, BK virus and CMV—the inventors have shown that this process is robust and reproducible. In addition, this process allows one to generate virus-specific T cells that have a specificity of >20 IFNγ SFCs against the immunodominant antigens and a cytotoxicity of >10% that is predominantly attributable to a second stimulation included in the manufacturing process. This process can be therefore used to generate and characterize T cells specific for any viruses, including hMPV and PIV3 as previously described.

4. Scope

Antigen-specific T cells manufactured and characterized by the process described above can be utilized in both a donor specific and 3' party setting. The two are described in detail below:

4.1 Donor Specific Setting

Figure 42:
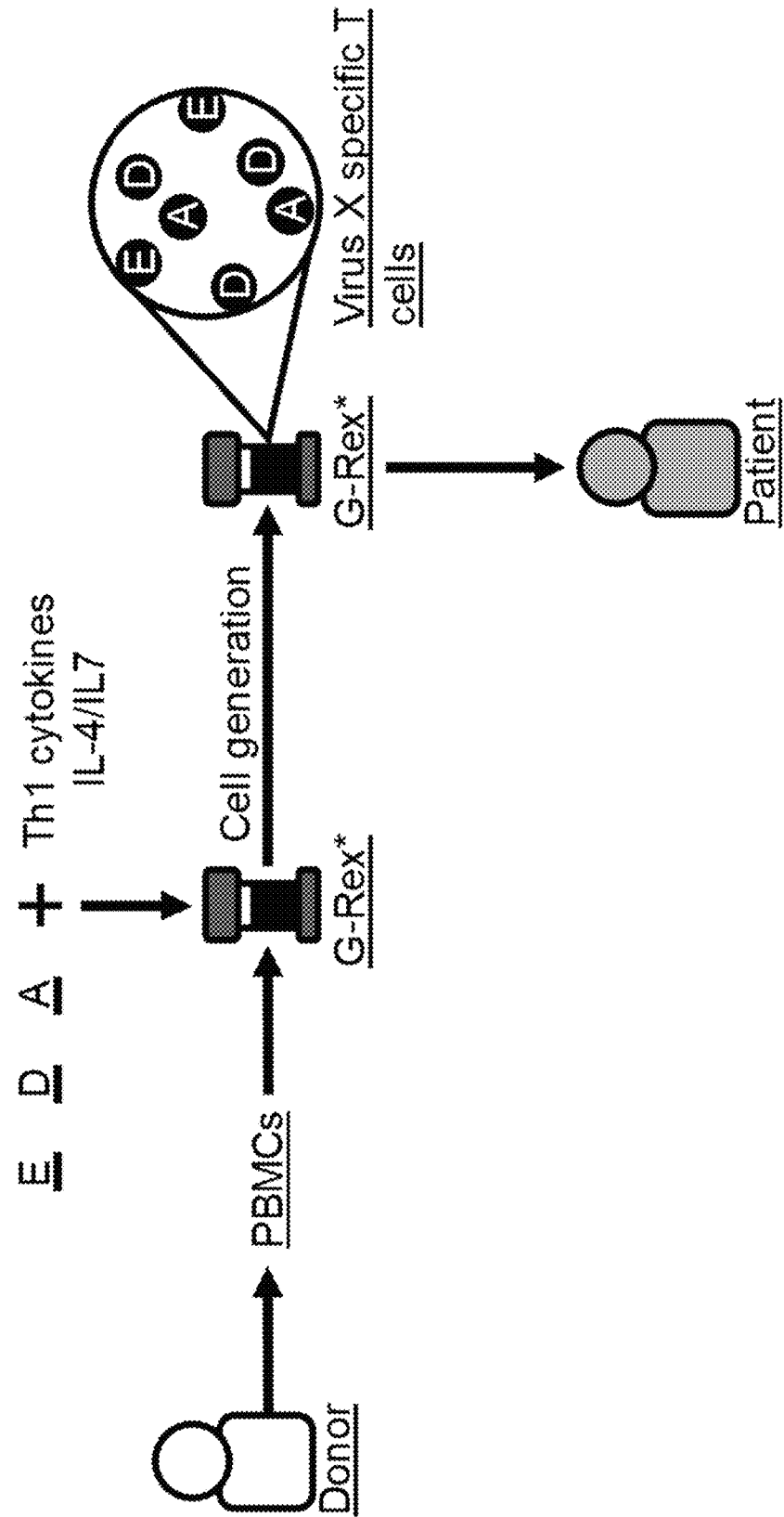
FIG. 42 illustrates administration to a patient of antigen-specific T cells generated from peripheral blood or leukapheresis product.

In this setting, antigen-specific T cells are generated from peripheral blood or leukapheresis product following steps as outlined in section 1. These cells can then be administered to the patient. This is outlined in FIG. 42.

4.2 Third-Party Setting

Figure 43:
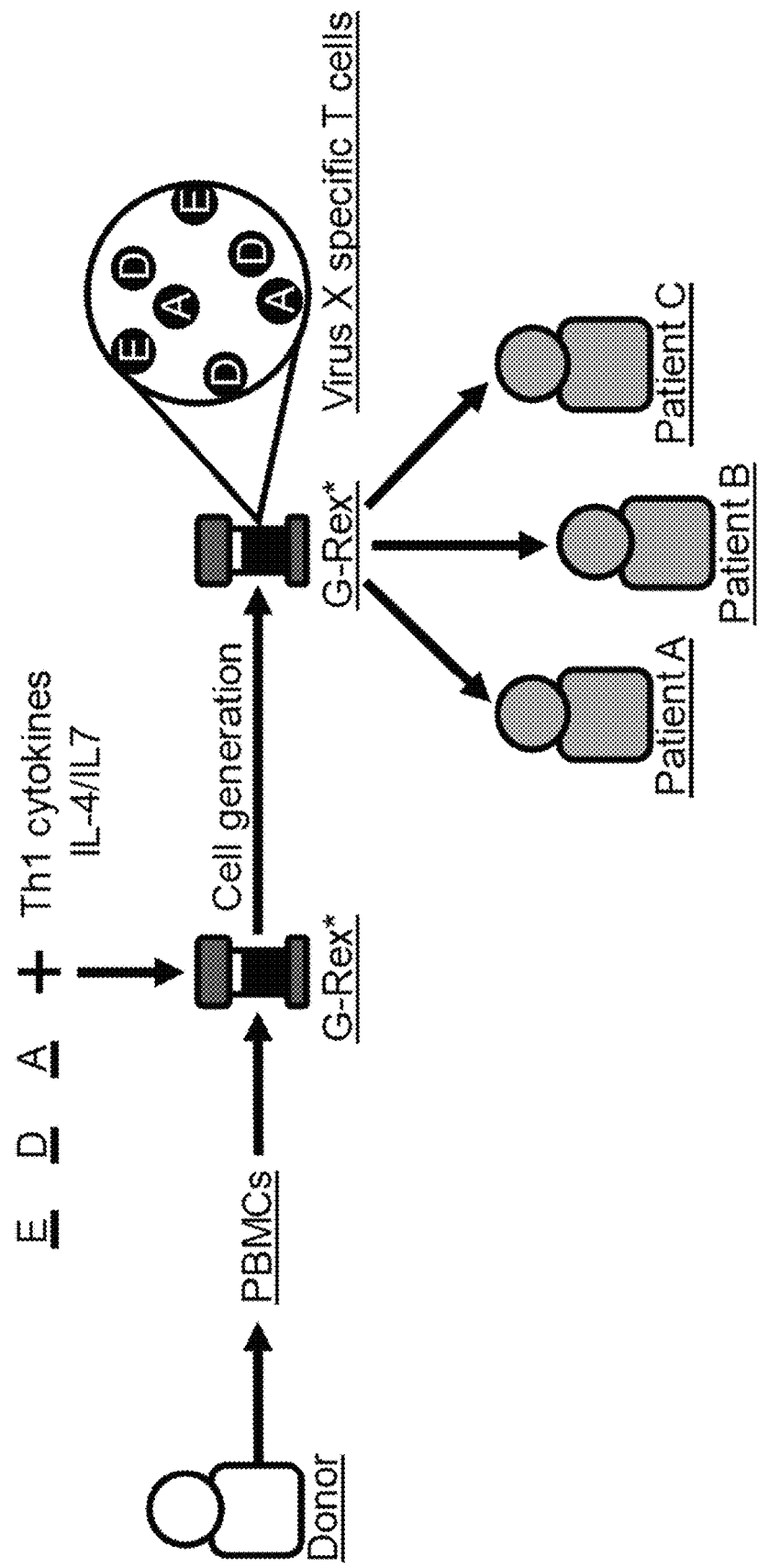
FIG. 43 illustrates off-the-shelf use of specific T cells.
Figure 44:
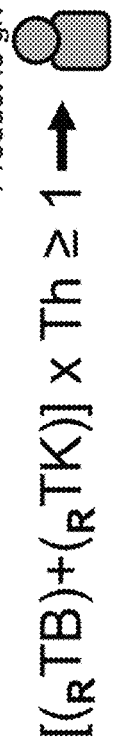
FIG. 44 provides mathematical examples of when a product of T cells is or is not given to a patient.
Figure 44:
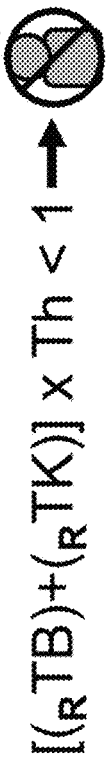

In this setting, antigen-specific T cells are generated and cryopreserved from peripheral blood or leukapheresis product following similar steps as outlined in section 1. These cells can then be administered to a number of partially HLA-matched recipients as outlined in FIG. 43.

Use of Product

The following description concerns how to determine whether or not a product is therapeutically useful. In specific embodiments, the use of the product may be defined by:

$[(_R TB)+(_R TK)] \times Th$, which when $\geq 1$ is administered to a patient and when $<1$ is not administered.

In this equation, $Th = HLA_P$ vs $HLA_{Pt}$, (the number of shared alleles) which when $\geq 1$ is equivalent to Th value of 1 and when $<1$ corresponds to a Th value of 0

$HLA_P$ = the HLA type of the product $HLA_{Pt}$ = the HLA type of the patient

Example 1 illustrates a scenario where a product will be administered to a specific patient.

Thio-P=212 SFC per $2 \times 10^5$ IL2

Tbio-U=44 SFC per $2 \times 10^5$ IL2

TSpec-P=5%

TCSpec=10%

$_R TB = [(Thio-P)+1]/[(Thio-U)+1]$ $_R TB = [(212)+1]/[(44)+1] = 4.7$

Therefore, $_R TB = 1$ $_R TK = [(TSpec-P)/(TCSpec)]$ $_R TK = [(5\%)/(10\%)] = 0.5$ Therefore, $_R TK = 0$ $HLA_P$=A(2,31), B(35,51), DR(3,4), DQ(2,4)

$HLA_{Pt}$=A(2,11), B(27,35), DR(4,8), DQ(3,4)

$HLA_P$ vs $HLA_{Pt}$=4

Therefore, Th=1

$[(_R TB)+(_R TK)] \times Th$ $[(1)+(0)] \times 1 = 1$

Therefore, this product will be administered to this particular patient.

Example 2 illustrates a scenario where a product will be administered to a specific patient.

Tbio-P=500 SFC per $2 \times 10^5$ IL2

Tbio-U=10 SFC per $2 \times 10^5$ IL2

TSpec-P=55%

TCSpec=10%

$_R TB = [(Thio-P)+1]/[(Thio-U)+1]$ $_R TB = [(500)+1]/[(10)+1] = 45.5$

Therefore, $_R TB = 1$ $_R TK = [(TSpec-P)/(TCSpec)]$ $_R TK = [(55\%)/(10\%)] = 5.5$ Therefore, $_R TK = 1$ $HLA_P$=A(2,24), B(8,14), DR(1,3), DQ(2,5)

$HLA_{Pt}$=A(2,23), B(15,44), DR(7,13), DQ(3,3)

$HLA_P$ vs $HLA_{Pt}$=1

Therefore, Th=1
[($_R$TB)+($_R$TK)]×Th
[(1)+(1)]×1=2
Therefore, this product will be administered to this particular patient.

Example 3 illustrates a scenario where a product will not be administered to a patient.
Tbio-P=1200 SFC per 2×10$^5$ IL2
Tbio-U=54 SFC per 2×10$^5$ IL2
TSpec-P=87%
TCSpec=10%
$_R$TB=[(Thio-P)+1]/[(Thio-U)+1]
$_R$TB=[(1200)+1]/[(54)+1]=21.8
Therefore,
$_R$TB=1
$_R$TK=[(TSpec-P)/(TCSpec)]
$_R$TK=[(87%)/(10%)]=8.7
Therefore,
$_R$TK=1
HLA$_P$=A(1,24), B(8,14), DR(11,8), DQ(2,5)
HLA$_{Pt}$=A(2,23), B(15,44), DR(7,13), DQ(3,3)
HLA$_P$ vs HLA$_{Pt}$=0
Therefore, Th=0
[($_R$TB)+($_R$TK)]×Th
[(1)+(1)]×0=0
Therefore, this product will not be administered to this particular patient.

Figure 45:
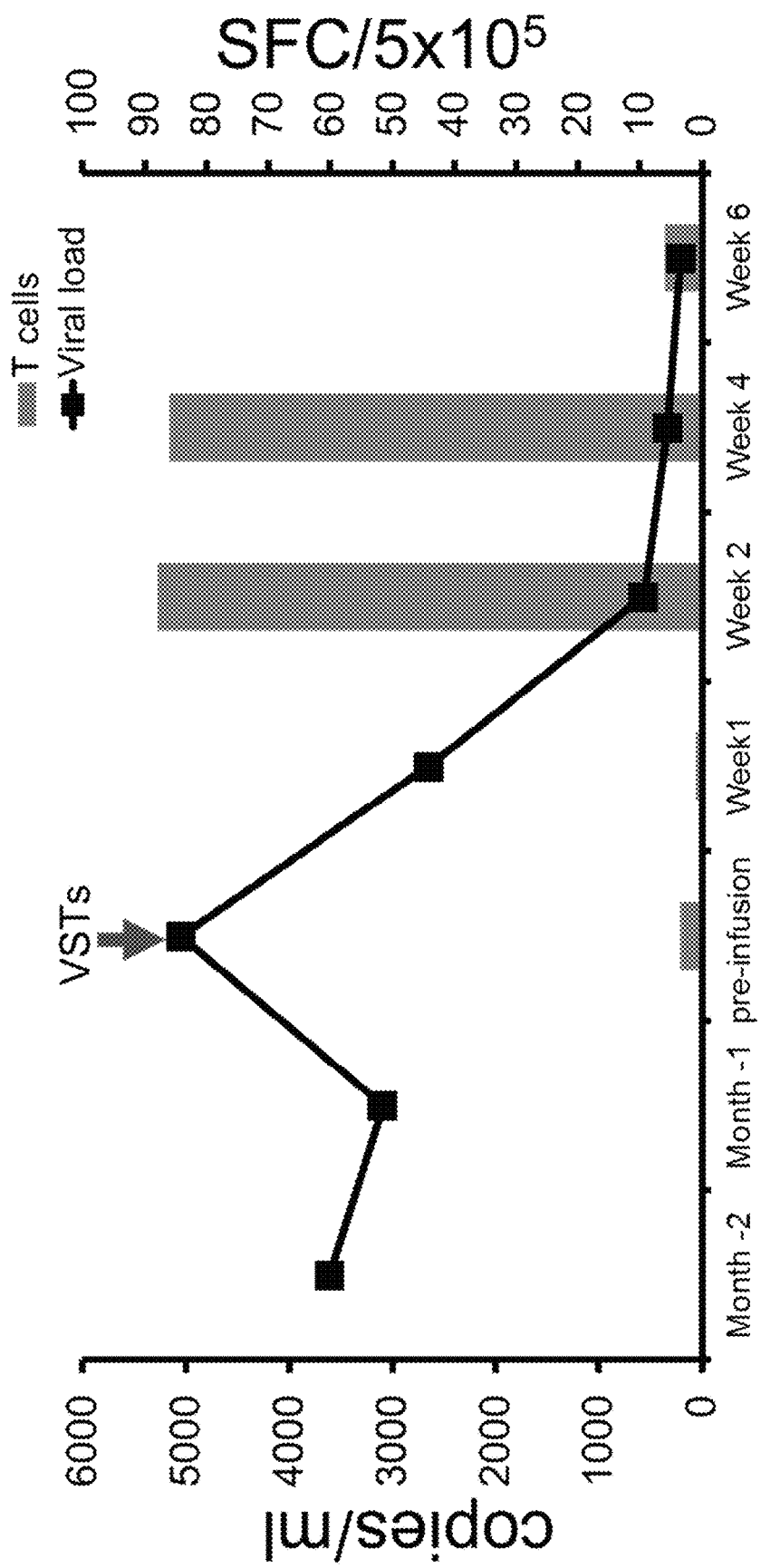
FIG. 45 shows clinical outcome of a patient with active CMV infection treated with a CMV-specific T cell product defined by the mathematical example in FIG. 44.

An example represents the clinical outcome of a patient with active CMV infection treated with a CMV-specific T cell product defined by ($_R$TB)+($_R$TK)≥1 and selected by [($_R$TB)+($_R$TK)]×Th≥1. As shown in FIG. 45, following the administration of CMV-specific T cells there was a subsequent decrease in the viral load as detected by PCR in the peripheral blood of the patient, which had an inverse correlation with the increase of CMV-specific T cells as detected by IFNγ ELIspot.

Figure 46:
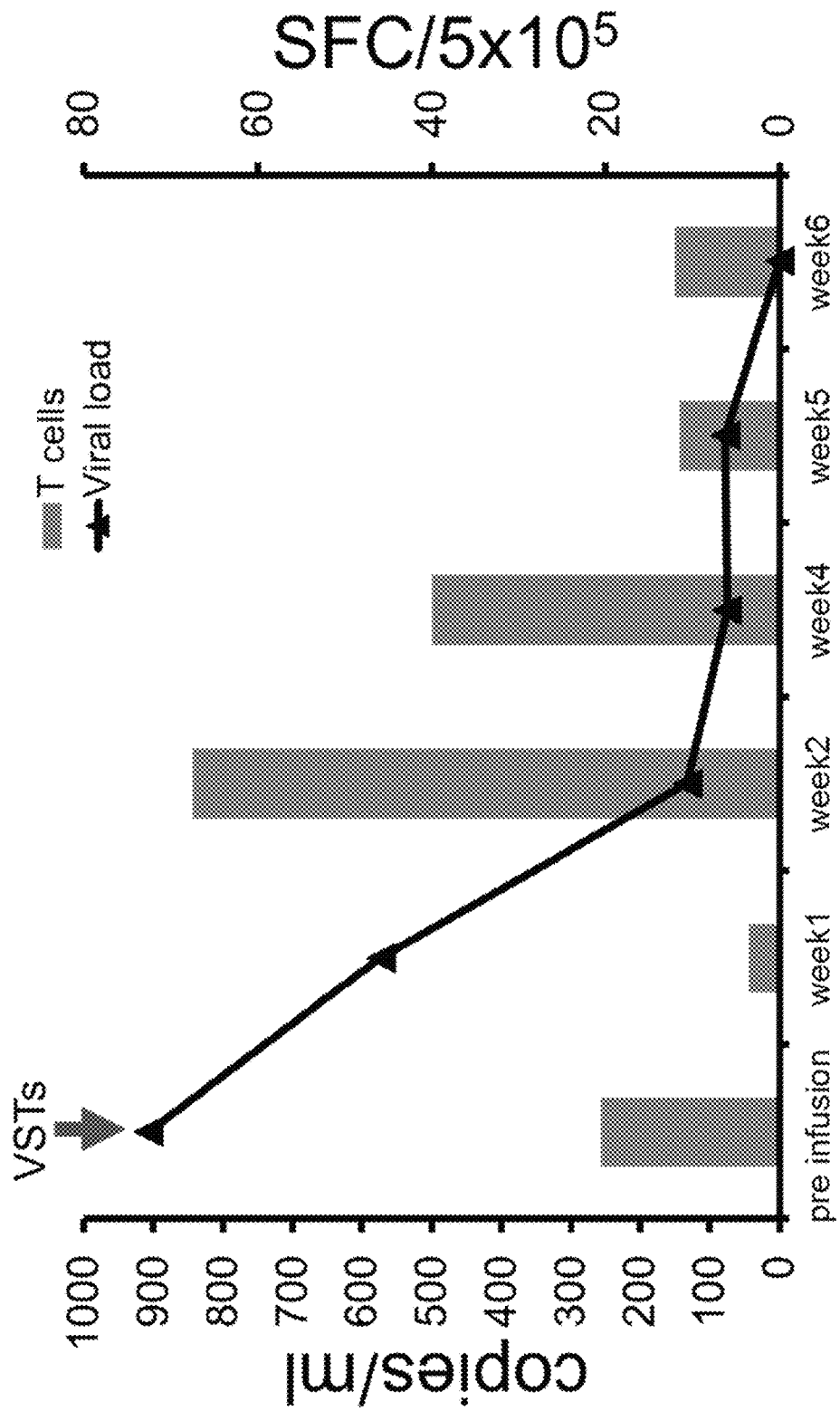
FIG. 46 shows clinical outcome of a patient with active EBV infection treated with a EBV-specific T cell product defined by the mathematical example in FIG. 44.

An example represents the clinical outcome of a patient with active viral infection treated with a EBV-specific T cell product defined by ($_R$TB)+($_R$TK)≥1 and selected by [($_R$TB)+($_R$TK)]×Th≥1. As shown in FIG. 46, following the administration of EBV-specific T cells there was a subsequent decrease in the viral load as detected by PCR in the peripheral blood of the patient, which had an inverse correlation with the increase of EBV-specific T cells as detected by IFNγ ELIspot.

Figure 47:
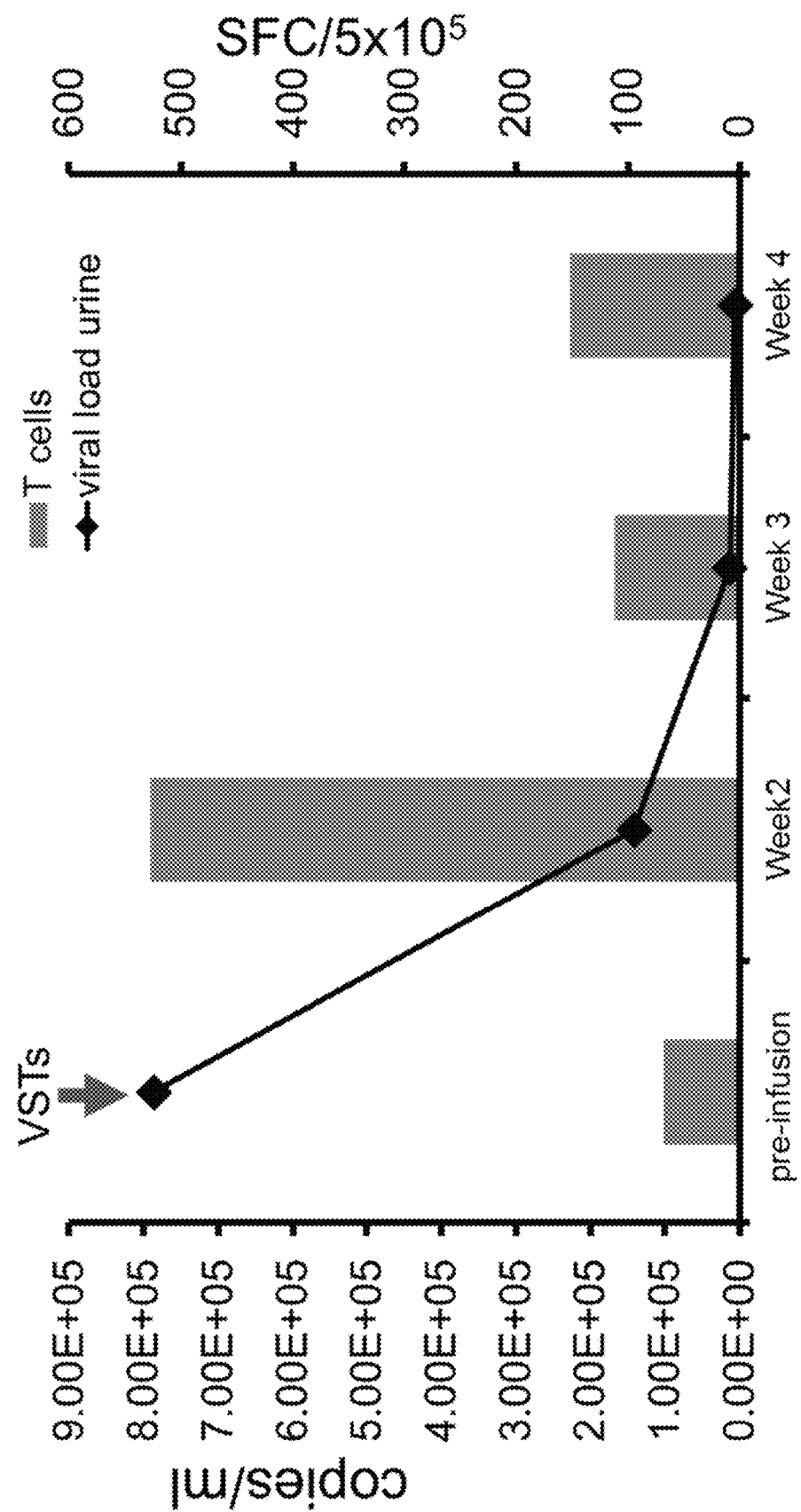
FIG. 47 shows clinical outcome of a patient with active BKV infection treated with a BKV-specific T cell product defined by the mathematical example in FIG. 44.

This example represents the clinical outcome of a patient with active viral infection treated with a BKV-specific T cell product defined by ($_R$TB)+($_R$TK)≥1 and selected by [($_R$TB)+($_R$TK)]×Th≥1. As shown in FIG. 47, following the administration of BKV-specific T cells there was a subsequent decrease in the viral load as detected by PCR in the urine of the patient, which had an inverse correlation with the increase of BKV-specific T cells as detected by IFNγ ELIspot.

Although embodiments of the present invention and its advantages have been described in detail, it should be understood that various changes, substitutions and alterations can be made herein without departing from the spirit and scope of the inventions as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present inventions. Accordingly, the appended claims are intended to include within their scope such processes, machines, manufacture, compositions of matter, means, methods, or steps.

What is claimed is:

1. A composition comprising an ex vivo expanded, donor-derived, polyclonal population of CD4+ and CD8+ virus-specific human T cells (VSTs) reactive against multiple immunodominant antigens from two or more respiratory viruses, wherein the viruses comprise human metapneumovirus (hMPV) and human parainfluenza virus type 3 (PIV3), wherein the multiple immunodominant antigens from hMPV are fusion (F), nucleoprotein (N), M2-1 protein (M2-1), and matrix protein (M), and wherein the multiple immunodominant antigens from PIV3 comprise matrix protein (M), hemagglutinin-neuraminidase (HN), and nucleoprotein (N).

2. A composition comprising an ex vivo expanded, donor-derived, polyclonal population of CD4+ and CD8+ virus-specific human T cells (VSTs) reactive against multiple immunodominant antigens from two or more respiratory viruses, wherein the viruses comprise hMPV and human PIV3, wherein the VSTs comprise T cells reactive to one or more libraries of peptides comprising peptides that overlap in sequence to span part or all of the multiple immunodominant antigens from hMPV and PIV3, wherein the multiple immunogenic antigens from hMPV are F, N, M2-1, and M, and wherein the multiple immunogenic antigens from PIV3 comprise M, HN, and N.

3. The composition of claim 2, wherein the peptides are at least 7 amino acids in length.

4. The composition of claim 3, wherein the peptides overlap by at least 3 amino acids.

5. The composition of claim 2, wherein the peptides are each 15 amino acids in length and overlap by 11 amino acids.

6. The composition of claim 2, wherein the peptides span the entire length of each of the multiple antigens.

* * * * *